(12) United States Patent
Hudson et al.

(10) Patent No.: US 12,358,931 B2
(45) Date of Patent: *Jul. 15, 2025

(54) 3-((1R,3s,5S)-3-((7-((5-METHYL-1H-PYRAZOL-3-YL)AMINO)-1,6-NAPHTHYRIDIN-5-YL)AMINO)-8-AZABICYCLO[3.2.1]OCTAN-8-YL) PROPANENITRILE AS A JAK KINASE INHIBITOR

(71) Applicant: THERAVANCE BIOPHARMA R&D IP, LLC, South San Francisco, CA (US)

(72) Inventors: Ryan Hudson, San Mateo, CA (US); Jennifer Kozak, Pacifica, CA (US); Paul R. Fatheree, San Francisco, CA (US); Dante D. Podesto, Modesto, CA (US); Gary E. L. Brandt, Alameda, CA (US); Melissa Fleury, Brisbane, CA (US); Anne-Marie Beausoleil, San Mateo, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/242,434

(22) Filed: Sep. 5, 2023

(65) Prior Publication Data
US 2024/0132520 A1 Apr. 25, 2024

Related U.S. Application Data

(60) Continuation of application No. 17/248,832, filed on Feb. 10, 2021, now Pat. No. 11,780,852, which is a continuation of application No. 16/599,434, filed on Oct. 11, 2019, now Pat. No. 10,947,254, which is a continuation of application No. 16/055,386, filed on Aug. 6, 2018, now Pat. No. 10,494,382, which is a division of application No. 15/631,220, filed on Jun. 23, 2017, now Pat. No. 10,072,026, which is a division of application No. 15/165,126, filed on May 26, 2016, now Pat. No. 9,725,470.

(60) Provisional application No. 62/312,273, filed on Mar. 23, 2016, provisional application No. 62/167,694, filed on May 28, 2015.

(51) Int. Cl.
*C07D 471/04* (2006.01)
*A61K 31/46* (2006.01)
*A61K 45/06* (2006.01)
*C07D 519/00* (2006.01)

(52) U.S. Cl.
CPC ............ *C07D 519/00* (2013.01); *A61K 31/46* (2013.01); *A61K 45/06* (2013.01); *C07B 2200/13* (2013.01)

(58) Field of Classification Search
CPC .................................................... C07D 471/04
USPC ......................................................... 544/122
See application file for complete search history.

(56) References Cited

U.S. PATENT DOCUMENTS

| 6,613,776 | B2 | 9/2003 | Kengtel et al. |
| 6,989,385 | B2 | 1/2006 | Bebbington et al. |
| 7,087,603 | B2 | 8/2006 | Bebbington et al. |
| 8,633,319 | B2 | 1/2014 | Atkinson et al. |
| 9,725,470 | B2 | 8/2017 | Hudson et al. |
| 10,028,960 | B2 | 7/2018 | Hudson et al. |
| 10,494,382 | B2 | 12/2019 | Hudson et al. |
| 2009/0281073 | A1 | 11/2009 | Bhattacharya et al. |
| 2011/0201608 | A1 | 8/2011 | Hoffmann et al. |
| 2020/0040010 | A1 | 2/2020 | Hudson et al. |

FOREIGN PATENT DOCUMENTS

| CN | 105367555 A | 3/2016 |
| WO | WO 2006067614 A2 | 6/2006 |
| WO | WO 2007071348 A1 | 6/2007 |
| WO | WO 20081197952 A1 | 10/2008 |
| WO | WO 2010002472 A1 | 1/2010 |
| WO | WO 2010038060 A1 | 4/2010 |
| WO | WO 2012160030 A1 | 11/2012 |

OTHER PUBLICATIONS

The International Search Report for PCT/US2016/034243 dated Aug. 2, 2016.
Carrion et al., "Cyclization of 2-dicyanomethylene-1,2-dihydropyridine-3-carbonitriles with amines: a mechanistic rationalization", Tetrahedron, 63: 215-223 (2007).
Hackam et al., "Translation of research evidence from animals to humans", JAMA, 296(14): 1731-1732 (Oct. 11, 2006).
Jordan, "Tamoxifen: A most unlikely pioneering medicine", Nature Reviews, Drug Discovery, (2): 205-213 (Mar. 2003).

*Primary Examiner* — Douglas M Willis
(74) *Attorney, Agent, or Firm* — Sheppard Mullin Richter & Hampton LLP

(57) ABSTRACT

Disclosed is a compound of the formula:

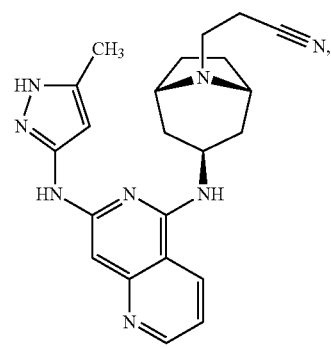

or a pharmaceutically-acceptable salt thereof. Also disclosed is a method of inhibiting a Janus kinase enzyme in a mammal using the compound.

5 Claims, 3 Drawing Sheets

3-((1R,3s,5S)-3-((7-((5-METHYL-1H-PYRAZOL-3-YL)AMINO)-1,6-NAPHTHYRIDIN-5-YL)AMINO)-8-AZABICYCLO[3.2.1]OCTAN-8-YL) PROPANENITRILE AS A JAK KINASE INHIBITOR

CROSS-REFERENCE TO RELATED APPLICATIONS

This application is a continuation of U.S. application Ser. No. 17/248,832, filed on Feb. 10, 2021; which application is a continuation of U.S. application Ser. No. 16/599,434, filed on Oct. 11, 2019 (now U.S. Pat. No. 10,947,254); which application is a continuation of U.S. application Ser. No. 16/055,386, filed on Aug. 6, 2018 (now U.S. Pat. No. 10,494,382); which application is a divisional of U.S. application Ser. No. 15/631,220, filed on Jun. 23, 2017 (now U.S. Pat. No. 10,072,026); which application is a divisional of U.S. application Ser. No. 15/165,126, filed on May 26, 2016 (now U.S. Pat. No. 9,725,470); which application claims the benefit of U.S. Provisional Application Nos. 62/167,694, filed on May 28, 2015, and 62/312,273, filed on Mar. 23, 2016, the disclosures of which are incorporated herein by reference in their entirety.

BACKGROUND OF THE INVENTION

Field of the Invention

The invention is directed to naphthyridine compounds useful as JAK kinase inhibitors. The invention is also directed to pharmaceutical compositions comprising such compounds, methods of using such compounds to treat inflammatory diseases, and processes and intermediates useful for preparing such compounds.

State of the Art

Ulcerative colitis is a chronic inflammatory disease of the colon. The disease is characterized by inflammation and ulceration of the mucosal layer of the rectum and the large intestine. Common symptoms include diarrhea, bloody stools, and abdominal pain. The clinical course is intermittent, marked by alternating periods of exacerbation and remission. Incidence seems to be greater in developed than in developing countries. An estimated 1.2 million people in major industrialized countries suffer from ulcerative colitis and the numbers are expected to increase along with population growth. Patients with ulcerative colitis are at an increased risk of developing colorectal cancer. (e.g. Danese et al. *N Engl J Med*, 2011, 365, 1713-1725).

Although there exists a variety of therapeutic options to promote and maintain remission of ulcerative colitis (UC) in patients, none is ideal. Sulfasalazine-related treatments are often effective in mild UC, but much less so in moderate to severe disease. Corticosteroids are often used to provide rapid induction of remission in patients with moderate to severe UC. However, chronic use of steroids to maintain remission is discouraged due to their association with longer term adverse effects (e.g., osteoporosis and fractures, infections, cataracts, slower wound healing and suppression of adrenal gland hormone production). Systemic immunosuppressants such as azathioprine, cyclosporine and methotrexate have a slow onset and modest efficacy in moderate to severe UC patients, but prolonged use can be problematic due to consequences of long-term systemic immunosuppression (e.g., increased risk of infections and lymphoma). Anti-TNFα antibodies (e.g., infliximab and adalimumab), while expensive and requiring subcutaneous or intravenous administration, are efficacious in approximately 60 to 70% of UC patients with moderate to severe disease. However, up to one third of patients fail to respond adequately, while another third of initial responders develop tolerance over a few weeks (Allez et al., *J Crohn's Colitis*, 2010, 4, 355-366; Rutgeerts et al., *N Engl J Med*, 2005, 353, 2462-2476). The most recently approved UC therapy, vedolizumab, an anti-$\alpha_4\beta_7$ integrin antibody, is efficacious in moderate to severe UC patients although its parenteral route is suboptimal, and the consequences of long-term immunosuppression via this mechanism remain to be determined. Despite existing therapeutic options, about 10 to 20% of UC patients still require colectomy within 10 years of diagnosis (Targownik et al., *Am J Gastroenterol*, 2012, 107, 1228-1235). It is clear there remains an unmet medical need for an effective therapy to promote and maintain remission of moderate to severe UC without the safety concerns resulting from chronic, systemic immunosuppression.

While the mechanism underlying ulcerative colitis is not completely understood, it is believed that environmental factors in genetically susceptible individuals evoke an inappropriate (excessive) reaction by the immune system to gut microbiota, resulting in colonic inflammation, tissue damage, and the associated symptoms characteristic of the disease.

Although the precise pathogenesis of UC is unclear, it is apparent that proinflammatory cytokines play a pivotal role in the immunological response (Strober et al., *Gastroenterol*, 2011, 140, 1756-1767). Many of the proinflammatory cytokines most commonly elevated in UC (e.g., IL-4, IL-6, IL-13, IL-15, IL-23, IL-24, IFNγ and leptin), rely on the JAK family of tyrosine kinases (i.e., JAK1, JAK2, JAK3 and Tyk2) for signal transduction. Ligand binding to a cytokine receptor triggers autophosphorylation of its associated JAK, which in turn results in phosphorylation of a signal transducer and activator of transduction (STAT) protein. Different STATs form hetero- or homodimers and promote transcription of their target genes in the cell nucleus to regulate functions such as cell growth, differentiation and death (Clark et al., *J Med Chem*, 2014, 57, 5023-5038).

Inhibition of the family of JAK enzymes could inhibit signaling of many key pro-inflammatory cytokines. Thus JAK inhibitors are likely to be useful in the treatment of ulcerative colitis and other inflammatory diseases such as Crohn's disease, allergic rhinitis, asthma, and chronic obstructive pulmonary disease (COPD). However, due to the modulating effect of the JAK/STAT pathway on the immune system, systemic exposure to JAK inhibitors may have an adverse systemic immunosuppressive effect. It would be desirable, therefore, to provide new JAK inhibitors which have their effect at the site of action without significant systemic effects. In particular, for the treatment of gastrointestinal inflammatory diseases, such as ulcerative colitis, it would be desirable to provide new JAK inhibitors which can be administered orally and achieve therapeutically relevant exposure in the gastrointestinal tract with minimal systemic exposure.

SUMMARY OF THE INVENTION

In one aspect, the invention provides novel compounds having activity as JAK kinase inhibitors.

Accordingly, the invention provides a compound of formula (I):

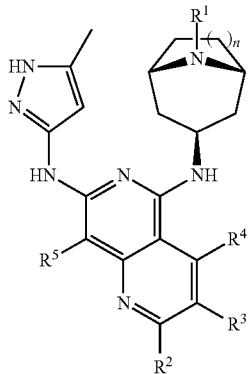 (I)

wherein
R¹ is selected from:
(a) $C_{1-4}$alkyl, wherein $C_{1-4}$alkyl is optionally substituted with one, two, or three fluoro or with a substituent selected from —CN; —$OC_{1-3}$alkyl; —C(O)$OC_{1-4}$alkyl; phenyl, wherein phenyl is optionally substituted with —OH; pyridinyl, wherein pyridinyl is optionally substituted with —CN; tetrahydropyranyl; —C(O)NR$^a$R$^b$, wherein R$^a$ and R$^b$ are independently hydrogen or $C_{1-3}$alkyl or R$^a$ is hydrogen and R$^b$ is

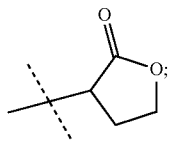

and a group selected from

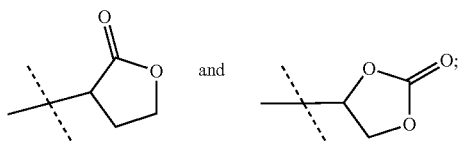 and (b) a group selected from

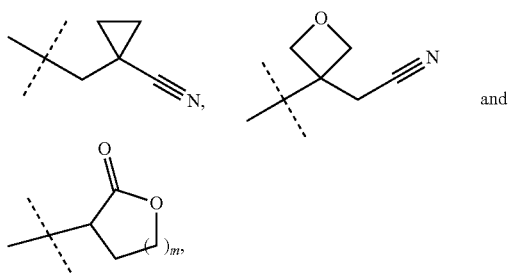

wherein m is 1 or 2;
(c) —C(O)R⁶, wherein R⁶ is selected from
$C_{1-4}$alkyl, wherein $C_{1-4}$alkyl is optionally substituted with one, two, or three fluoro or with a substituent selected from —OH, —CN, —$OC_{1-4}$alkyl, phenyl, and —NR$^e$R$^f$, wherein R$^e$ and R$^f$ are independently hydrogen or $C_{1-3}$alkyl;
$C_{3-6}$cycloalkyl, wherein $C_{3-6}$cycloalkyl is optionally substituted with $C_{1-3}$alkyl;
pyridinyl, wherein pyridinyl is optionally substituted with —CN; and

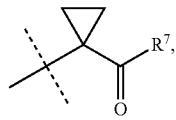

wherein R⁷ is —CN, —CF₃, or —OCH₃;
(d) —C(O)OR⁸, wherein R⁸ is selected from
$C_{1-4}$alkyl, wherein $C_{1-4}$alkyl is optionally substituted with —CN, $C_{3-6}$cycloalkyl, tetrahydrofuranyl, or —OR$^m$, wherein R$^m$ is hydrogen or $C_{1-3}$alkyl; and
$C_{1-4}$alkenyl; and
(e) —S(O)₂R⁹, wherein R⁹ is selected from
$C_{1-4}$alkyl, wherein $C_{1-4}$alkyl is optionally substituted with —CN, —$OC_{1-3}$alkyl, phenyl, pyridinyl, or $C_{3-6}$cycloalkyl,
$C_{1-4}$alkenyl,
$C_{3-6}$cycloalkyl, wherein $C_{3-6}$cycloalkyl is optionally substituted with $C_{1-3}$alkyl,
phenyl,
pyridinyl, wherein pyridinyl is optionally substituted with fluoro,
heterocycle containing 4 to 6 ring atoms including one nitrogen atom, wherein the heterocycle is optionally substituted with —CN or $C_{1-3}$alkyl, wherein $C_{1-3}$alkyl is optionally substituted with —CN or —$OC_{1-3}$alkyl; and

R² is selected from hydrogen, —$OC_{1-3}$alkyl, and —CH₂—R¹⁰, wherein R¹⁰ is selected from —OH, morpholinyl, piperidinyl, wherein piperidinyl is optionally substituted with two fluoro, and piperazinyl, wherein piperazinyl is optionally substituted with methyl;
R³ is selected from hydrogen, $C_{1-3}$alkyl, —$OC_{1-3}$alkyl, —C(O)$OC_{1-3}$alkyl, —S(O)₂$C_{1-3}$alkyl, and —CH₂S(O)₂$C_{1-3}$alkyl;
R⁴ is hydrogen or —$OC_{1-3}$alkyl;
R⁵ is hydrogen or fluoro; and
n is 1 or 2;
provided that
when R³ is —$OC_{1-3}$alkyl and R², R⁴, and R⁵ are each hydrogen, R⁹ is not phenyl;
when R⁵ is fluoro, n is 1, and R², R³, and R⁴ are each hydrogen, R⁹ is not phenyl; and
when R⁵ is fluoro, R³ is methyl, and R² and R⁴ are each hydrogen, R¹ is not —C(O)OR⁸;
or a pharmaceutically-acceptable salt or stereoisomer thereof.

As used hereinafter, the phrase "compound of formula (I)" means a compound of formula (I) or a pharmaceutically acceptable salt thereof; i.e., this phrase means a compound of formula (I) in free base form or in a pharmaceutically acceptable salt form unless otherwise indicated.

The invention also provides a pharmaceutical composition comprising a compound of the invention and a pharmaceutically-acceptable carrier.

In another aspect, the invention provides a particular compound of formula (I) in crystalline free base form. Crystalline 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile has been found to have a melting temperature in the range of about 243° C. to about 253° C., typically between about 246° C. and about 250° C., a decomposition onset at about 237° C., and to exhibit weight changes of less than about 0.15% when exposed to a range of relative humidity between about 5% and about 90% at room temperature. In yet another aspect, the invention provides a crystalline solvate of 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile.

The invention also provides a method of treating gastrointestinal inflammatory disease, in particular, ulcerative colitis in a mammal, the method comprising administering to the mammal a therapeutically effective amount of a compound or of a pharmaceutical composition of the invention. In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating gastrointestinal inflammatory disease in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
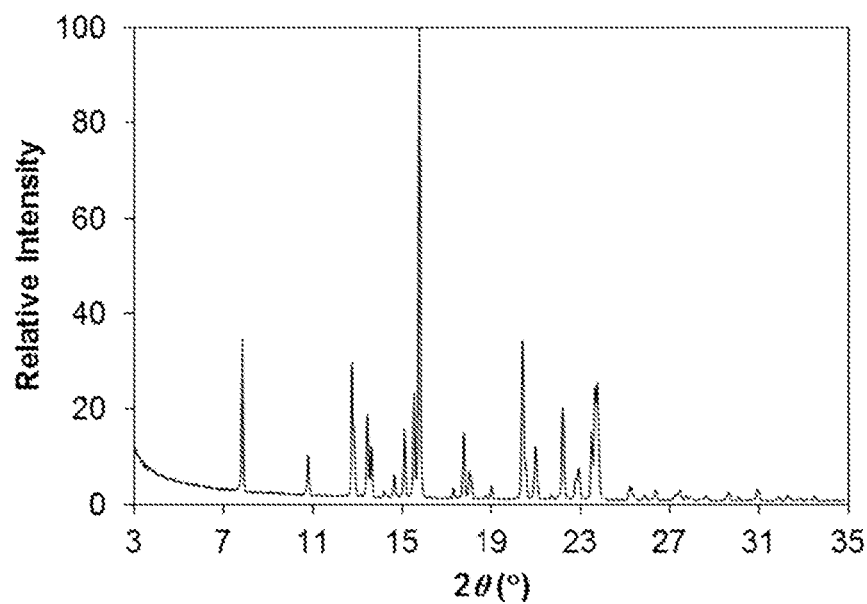
FIG. 1 shows a powder x-ray diffraction (PXRD) pattern of crystalline Form I 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile [hereinafter Form I].

Among other aspects, the invention provides JAK kinase inhibitors of formula (I), pharmaceutically-acceptable salts thereof, and intermediates for the preparation thereof. The following substituents and values are intended to provide representative examples of various aspects of this invention. These representative values are intended to further define such aspects and are not intended to exclude other values or limit the scope of the invention.

In a specific aspect, $R^1$ is $C_{1-4}$alkyl, wherein $C_{1-4}$alkyl is optionally substituted with one, two, or three fluoro or with a substituent selected from —CN; —OC$_{1-3}$alkyl; —C(O)OC$_{1-4}$alkyl; phenyl, wherein phenyl is optionally substituted with —OH; pyridinyl, wherein pyridinyl is optionally substituted with —CN; tetrahydropyranyl; —C(O)NR$^a$R$^b$, wherein R$^a$ and R$^b$ are independently hydrogen or $C_{1-3}$alkyl or R$^a$ is hydrogen and R$^b$ is

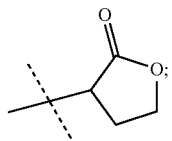

and a group selected from

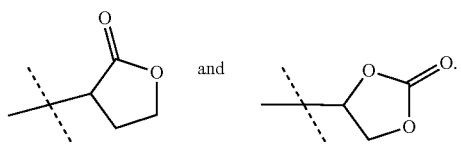

In another specific aspect, $R^1$ is $C_{1-4}$alkyl, wherein $C_{1-4}$alkyl is optionally substituted with one, two, or three fluoro or with a substituent selected from —CN; —OC$_{1-3}$alkyl; phenyl, wherein phenyl is optionally substituted with —OH; pyridinyl, wherein pyridinyl is optionally substituted with —CN; tetrahydropyranyl; —C(O)NHCH$_3$; and

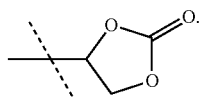

In another specific aspect, $R^1$ is $C_{1-4}$alkyl, wherein $C_{1-4}$alkyl is substituted with one, two, or three fluoro, or with —CN, or —C(O)NHCH$_3$.

In specific aspects, $R^1$ is a group selected from

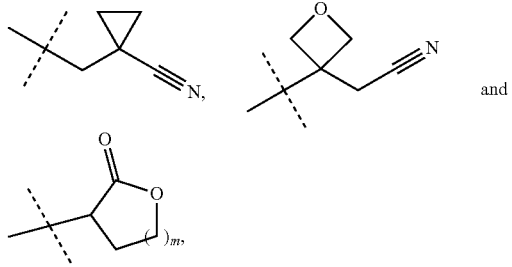

wherein m is 1 or 2, or wherein m is 1.

In a specific aspect, $R^1$ is —C(O)R$^6$, wherein R$^6$ is selected from $C_{1-4}$alkyl, wherein $C_{1-4}$alkyl is optionally substituted with one, two, or three fluoro or with a substituent selected from —OH, —CN, —OC$_{1-4}$alkyl, phenyl, and —NR$^e$R$^f$, wherein R$^e$ and R$^f$ are independently hydrogen or $C_{1-3}$alkyl; $C_{3-6}$cycloalkyl, wherein $C_{3-6}$cycloalkyl is optionally substituted with $C_{1-3}$alkyl; pyridinyl, wherein pyridinyl is optionally substituted with —CN; and

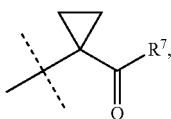

wherein $R^7$ is —CN, —$CF_3$, or —$OCH_3$.

In another specific aspect, $R^1$ is —C(O)$R^6$, wherein $R^6$ is selected from $C_{1-4}$alkyl, wherein $C_{1-4}$alkyl is optionally substituted with one, two, or three fluoro or with a substituent selected from —OH and phenyl; $C_{3-6}$cycloalkyl, wherein $C_{3-6}$cycloalkyl is optionally substituted with $C_{1-3}$alkyl; and

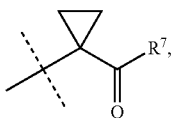

wherein $R^7$ is —CN or —$CF_3$.

In another specific aspect, $R^1$ is -C(O)$R^6$, wherein $R^6$ is $C_{1-4}$alkyl, wherein $C_{1-4}$alkyl is substituted with one, two, or three fluoro, or with —CN or —C(O)NH$CH_3$.

In a specific aspect, $R^1$ is —C(O)O$R^8$, wherein $R^8$ is selected from $C_{1-4}$alkyl, wherein $C_{1-4}$alkyl is optionally substituted with —CN, $C_{3-6}$cycloalkyl, tetrahydrofuranyl, or —O$R^m$, wherein $R^m$ is hydrogen or $C_{1-3}$alkyl; and $C_{1-4}$alkenyl.

In a specific aspect, $R^1$ is —S(O)$_2$$R^9$, wherein $R^9$ is selected from $C_{1-4}$alkyl, wherein $C_{1-4}$alkyl is optionally substituted with —CN, —O$C_{1-3}$alkyl, phenyl, pyridinyl, or $C_{3-6}$cycloalkyl; $C_{1-4}$alkenyl; $C_{3-6}$cycloalkyl, wherein $C_{3-6}$cycloalkyl is optionally substituted with $C_{1-3}$alkyl; phenyl; pyridinyl, wherein pyridinyl is optionally substituted with fluoro; heterocycle containing 4 to 6 ring atoms including one nitrogen atom, wherein the heterocycle is optionally substituted with —CN or $C_{1-3}$alkyl, wherein $C_{1-3}$alkyl is optionally substituted with —CN or —O$C_{1-3}$alkyl; and

In another specific aspect, $R^1$ is —S(O)$_2$$R^9$, wherein $R^9$ is selected from $C_{1-4}$alkyl, wherein $C_{1-4}$alkyl is optionally substituted with —CN, —O$C_{1-3}$alkyl, phenyl, pyridinyl, or $C_{3-6}$cycloalkyl; $C_{1-4}$alkenyl; $C_{3-6}$cycloalkyl, wherein $C_{3-6}$cycloalkyl is optionally substituted with $C_{1-3}$alkyl; pyridinyl, wherein pyridinyl is optionally substituted with fluoro; heterocycle containing 4 or 5 ring atoms including one nitrogen atom, wherein the heterocycle is bonded to sulfur through the nitrogen atom and the heterocycle is optionally substituted with —CN or with —$CH_2$O$CH_3$; and

In another specific aspect, $R^1$ is —S(O)$_2$$R^9$, wherein $R^9$ is pyridinyl.

In yet another aspect, $R^1$ is selected from —(CH$_2$)$_2$CN, —$CH_2$$CH_2$F, —$CH_2$C(O)NH$CH_3$, —C(O)CHF$_2$, and —S(O)$_2$-pyridin-3-yl.

In a specific aspect, $R^2$ is selected from hydrogen, —O$C_{1-3}$alkyl, and —$CH_2$—$R^{10}$, wherein $R^{10}$ is selected from —OH, morpholinyl, piperidinyl, wherein piperidinyl is optionally substituted with two fluoro, and piperazinyl, wherein piperazinyl is optionally substituted with methyl.

In another specific aspect, $R^2$ is selected from hydrogen, —O$CH_3$, and —$CH_2$—$R^{10}$, wherein $R^{10}$ is selected from —OH, morpholinyl, piperidinyl, wherein piperidinyl is substituted with 2 fluoro at the 4-position, and piperazinyl, wherein piperazinyl is substituted with methyl at the 4-position.

In yet another specific aspect, $R^2$ is hydrogen.

In a specific aspect, $R^3$ is selected from hydrogen, $C_{1-3}$alkyl, —O$C_{1-3}$alkyl, —C(O)O$C_{1-3}$alkyl, —S(O)$_2$$C_{1-3}$alkyl, and —$CH_2$S(O)$_2$$C_{1-3}$alkyl.

In another specific aspect, $R^3$ is selected from hydrogen, —$CH_3$, —O$CH_3$, and —C(O)O$CH_3$.

In yet another specific aspect, $R^3$ is hydrogen.

In specific aspects, $R^4$ is hydrogen or —O$C_{1-3}$alkyl; or $R^4$ is hydrogen or —O$CH_3$, or $R^4$ is hydrogen.

In specific aspects, $R^5$ is hydrogen or fluoro, or $R^5$ is hydrogen.

In a specific aspect n is 1. In another specific aspect n is 2.

In a specific aspect, the invention provides a compound of formula (I) wherein:

$R^1$ is selected from:

(a) $C_{1-4}$alkyl, wherein $C_{1-4}$alkyl is optionally substituted with one, two, or three fluoro or with a substituent selected from —CN; —O$C_{1-3}$alkyl; phenyl, wherein phenyl is optionally substituted with —OH; pyridinyl, wherein pyridinyl is optionally substituted with —CN; tetrahydropyranyl; —C(O)NH$CH_3$; and

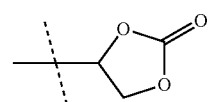

(b) a group selected from

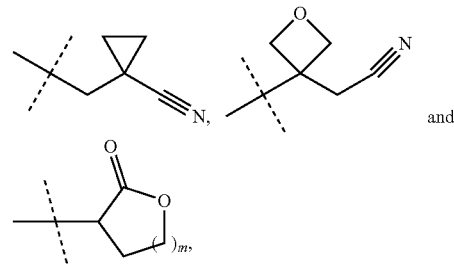

wherein m is 1;

(c) —C(O)$R^6$, wherein $R^6$ is selected from $C_{1-4}$alkyl, wherein $C_{1-4}$alkyl is optionally substituted with one, two, or three fluoro or with a substituent selected from —OH and phenyl; $C_{3-6}$cycloalkyl, wherein $C_{3-6}$cycloalkyl is optionally substituted with $C_{1-3}$alkyl; and

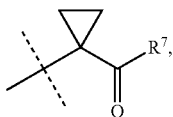

wherein $R^7$ is —CN or —CF$_3$;
(d) —C(O)OR$^8$ wherein $R^8$ is selected from C$_{1-4}$alkyl, wherein C$_{1-4}$alkyl is optionally substituted with —CN, C$_{3-6}$cycloalkyl, tetrahydrofuranyl, or —OR$^m$, wherein $R^m$ is hydrogen or C$_{1-3}$alkyl; and C$_{1-4}$alkenyl; and
(e) —S(O)$_2$R$^9$, wherein $R^9$ is selected from C$_{1-4}$alkyl, wherein C$_{1-4}$alkyl is optionally substituted with —CN, —OC$_{1-3}$alkyl, phenyl, pyridinyl, or C$_{3-6}$cycloalkyl; C$_{1-4}$alkenyl; C$_{3-6}$cycloalkyl, wherein C$_{3-6}$cycloalkyl is optionally substituted with C$_{1-3}$alkyl; pyridinyl, wherein pyridinyl is optionally substituted with fluoro; heterocycle containing 4 or 5 ring atoms including one nitrogen atom, wherein the heterocycle is bonded to sulfur through the nitrogen atom and the heterocycle is optionally substituted with —CN or —CH$_2$OCH$_3$; and

$R^2$ is selected from hydrogen, —OCH$_3$, and —CH$_2$—R$^{10}$, wherein R$^{10}$ is selected from —OH, morpholinyl, piperidinyl, wherein piperidinyl is substituted with two fluoro at the 4-position, and piperazinyl, wherein piperazinyl is substituted with methyl at the 4-position;
$R^3$ is selected from hydrogen, —CH$_3$, —OCH$_3$, and —C(O)OCH$_3$;
$R^4$ is hydrogen or —OCH$_3$;
$R^5$ is hydrogen or fluoro; and
n is 1 or 2,
provided that when $R^5$ is fluoro, $R^3$ is hydrogen.
In another specific aspect, the invention provides a compound of formula (I) wherein:
$R^1$ is selected from:
(a) C$_{1-4}$alkyl, wherein C$_{1-4}$alkyl is substituted with one, two, or three fluoro, or with —CN or —C(O)NHCH$_3$;
(c) —C(O)R$^6$, wherein R$^6$ is C$_{1-4}$alkyl, wherein C$_{1-4}$alkyl is substituted with one, two, or three fluoro; and
(e) —S(O)$_2$R$^9$ wherein R$^9$ is pyridinyl;
$R^2$, $R^3$, $R^4$, and $R^5$ are each hydrogen; and
n is 1 or 2.
In a certain aspect, the invention provides compounds of formula (II):

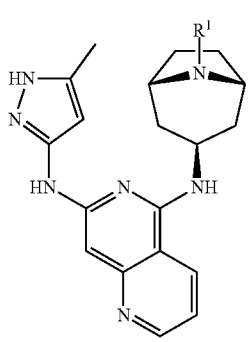

wherein the variable $R^1$ is as defined herein.

In another aspect, the invention provides compounds of formula (III):

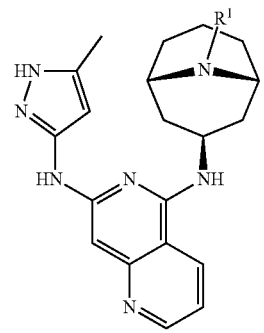

wherein the variable $R^1$ is as defined herein.

In one aspect, the invention provides the compounds of Examples 1-23 and Tables 1-8 below In another aspect, the invention provides a compound selected from the following compounds 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile, N$^5$-((1R,3s,5S)-8-(2-fluoroethyl)-8-azabicyclo[3.2.1]octan-3-yl)-N$^7$-(5-methyl-1H-pyrazol-3-yl)-1,6-naphthyridine-5,7-diamine, N$^7$-(5-methyl-1H-pyrazol-3-yl)-N$^5$-((1R,3s,5S)-8-(pyridin-3-ylsulfonyl)-8-azabicyclo[3.2.1]octan-3-yl)-1,6-naphthyridine-5,7-diamine, 2-(dimethylamino)-1-((1R,3s,5S)-3-((7-((5-methyl-1H-pyrazol-3-yl)amino)-1,6-naphthyridin-5-yl)amino)-9-azabicyclo[3.3.1]nonan-9-yl)ethan-1-one, 2,2-difluoro-1-((1R,3s,5S)-3-((7-((5-methyl-1H-pyrazol-3-yl)amino)-1,6-naphthyridin-5-yl)amino)-8-azabicyclo[3.2.1]octan-8-yl)ethan-1-one, N$^5$-((1R,3s,5S)-8-((2-methoxyethyl)sulfonyl)-8-azabicyclo[3.2.1]octan-3-yl)-N$^7$-(5-methyl-1H-pyrazol-3-yl)-1,6-naphthyridine-5,7-diamine, N$^7$-(5-methyl-1H-pyrazol-3-yl)-N-((1R,3s,5S)-9-(pyridin-3-ylsulfonyl)-9-azabicyclo[3.3.1]nonan-3-yl)-1,6-naphthyridine-5,7-diamine, isobutyl (1R,3s,5S)-3-((2-(hydroxymethyl)-7-((5-methyl-1H-pyrazol-3-yl)amino)-1,6-naphthyridin-5-yl)amino)-8-azabicyclo[3.2.1]octane-8-carboxylate, N-methyl-2-((1R,3s,5S)-3-((7-((5-methyl-1H-pyrazol-3-yl)amino)-1,6-naphthyridin-5-yl)amino)-9-azabicyclo[3.3.1]nonan-9-yl)acetamide, and pharmaceutically acceptable salts thereof.

Chemical structures are named herein according to IUPAC conventions as implemented in ChemDraw software (PerkinElmer, Inc., Cambridge, MA). For example, the compound of Example 1:

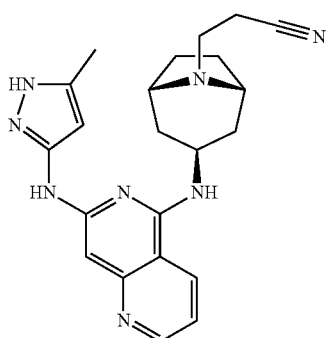

is designated as 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile. The (1R,3s,5S) notation describes the exo orientation of the naphthyridinylamino group with respect to the 8-azabicyclo-[3.2.1]octane group. All of the compounds of the invention are in the exo orientation.

Furthermore, the pyrazolyl moiety of the compounds of formula (I) exists in tautomeric form. For example, the compound of Example 1 may equivalently be represented as:

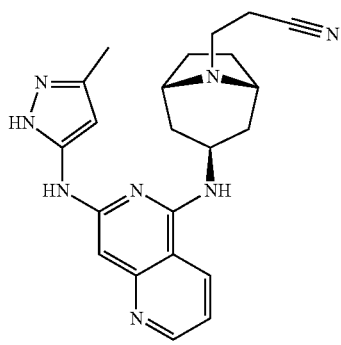 [SMILES: Cc1cc(Nc2cc3ncccc3c(N[C@@H]3C[C@H]4CC[C@@H](C3)N4CCC#N)n2)[nH]n1]

According to the IUPAC convention, these representations give rise to different numbering of the atoms of the pyrazolyl portion. The above representation is designated as 3-((1R,3s,5S)-3-((7-((3-methyl-1H-pyrazol-5-yl)amino)-1,6-naphthyridin-5-yl)amino)-8-azabicyclo[3.2.1]octan-8-yl)propanenitrile, where the underlining identifies where the name differs from that of the first representation. It will be understood that although structures are shown, or named, in a particular form, the invention also includes the tautomer thereof.

The compounds of the invention contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Compounds of formula (I) also contain several basic groups (e.g., amino groups) and therefore, such compounds can exist as the free base or in various salt forms, such a mono-protonated salt form, a di-protonated salt form, a tri-protonated salt form, or mixtures thereof. All such forms are included within the scope of this invention, unless otherwise indicated.

This invention also includes isotopically-labeled compounds of formula (I), i.e., compounds of formula (I) where an atom has been replaced or enriched with an atom having the same atomic number but an atomic mass different from the atomic mass that predominates in nature. Examples of isotopes that may be incorporated into a compound of formula (I) include, but are not limited to, $^{2}H$, $^{3}H$, $^{11}C$, $^{13}C$, $^{14}C$, $^{13}N$, $^{15}N$, $^{15}O$, $^{17}O$, $^{18}O$, $^{35}S$ $^{36}Cl$, and $^{18}F$. Of particular interest are compounds of formula (I) enriched in tritium or carbon-14, which compounds can be used, for example, in tissue distribution studies. Also of particular interest are compounds of formula (I) enriched in deuterium especially at a site of metabolism, which compounds are expected to have greater metabolic stability. Additionally of particular interest are compounds of formula (I) enriched in a positron emitting isotope, such as $^{11}C$, $^{18}F$, $^{15}O$ and $^{13}N$, which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "therapeutically effective amount" means an amount sufficient to effect treatment when administered to a patient in need of treatment.

The term "treatment" as used herein means the treatment of a disease, disorder, or medical condition (such as a gastrointestinal inflammatory disease), in a patient, such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), tert-butyldimethylsilyl (TBDMS), [2-(trimethylsilyl)ethoxy]methyl (SEM); and the like. Numerous protecting groups, and their introduction and removal, are described in T. W. Greene and G. M. Wuts, *Protecting Groups in Organic Synthesis*, Third Edition, Wiley, New York General Synthetic Procedures Compounds of this invention, and intermediates thereof, can be prepared according to the following general methods and procedures using commercially-available or routinely-prepared starting materials and reagents. The substituents and variables (e.g., $R^1$, $R^2$, $R^3$, $R^4$, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials know to those skilled in the art. In particular, it will be appreciated that compounds of the invention may be prepared by a variety of process routes in which reactants are combined in different orders to provide different intermediates en route to producing final products.

A general method of preparing final compounds of the invention utilizes a key intermediate 1 as illustrated in Scheme 1. The variables $R^1$, $R^2$, $R^3$, $R^4$, $R^5$, $R^6$, $R^8$, and $R^9$ are defined as in formula (I), $R^4$ represents an optionally substituted $C_{1-4}$alkyl, and L is a leaving group. For simplicity, the scheme shows compounds in which the variable n of formula (I) is defined as 1, i.e. the bicyclo group is 8-azabicyclo[3.2.1]octyl. An analogous process is used to prepare compounds in which the variable n is 2.

Scheme 1

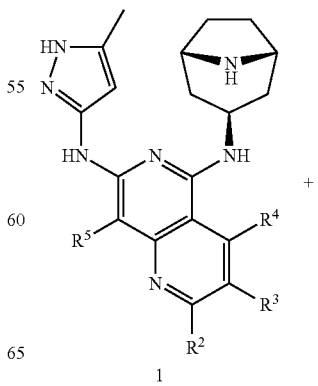

1

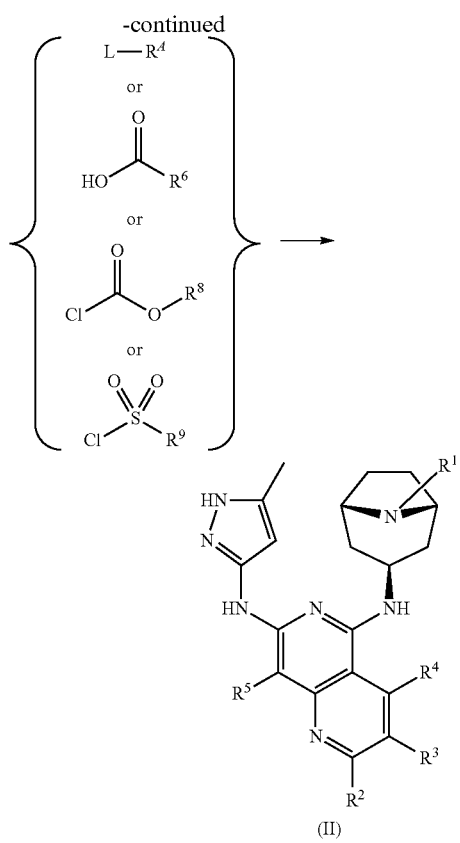

(II)

To prepare compounds in which $R^1$ is an optionally substituted alkyl group as defined in option (a), the alkylation reaction typically uses a halo leaving group L, principally bromo or iodo, although alternative leaving groups such as hydroxy or trifluoromethanesulfonate (commonly triflate) may also be employed. The reaction is typically conducted by contacting intermediate 1 with an excess of the reagent L-$R^4$ in an inert diluent in the presence of an excess of base. The reaction is typically conducted at a temperature between about 20 and about 60° C. for between about 10 and 24 hours or until the reaction is substantially complete.

Alternatively, the Michael addition reaction may be used to prepare compounds in which $R^1$ is a cyanoethyl group. For example, as described in the examples below, to prepare a compound in which $R^1$ is —$(CH_2)_2CN$, intermediate 1 is contacted with an excess, for example 1.1 to 1.5 equivalents, of acrylonitrile in the presence of an excess of base, for example diisopropylethylamine or diazobicycloundecene. The reaction is typically conducted at room temperature for between about 3 and about 24 hours or until the reaction is substantially complete. In certain cases it is useful to prepare compounds in which $R^1$ is an optionally substituted alkyl group by reductive amination with a suitably selected aldehyde.

Compounds in which $R^1$ is defined as —$C(O)R^6$ may be prepared by contacting intermediate 1 with a modest excess of carboxylic acid reagent HO—C(O)—$R^6$ under typical amide coupling conditions. The reaction is typically performed in the presence of an excess of base utilizing an activating agent such as N,N,N',N'-tetramethyl-O-(7-azabenzotriazol-1-yl)uronium hexafluorophosphate (HATU). The reaction is typically conducted at room temperature for between about 3 and about 24 hours or until the reaction is substantially complete.

A chloroformate reagent Cl—$C(O)OR^8$ may be used to prepare carbamate compounds in which $R^1$ is defined as —$C(O)OR^8$. Typically, intermediate 1 is contacted with about 1 equivalent of the chloroformate in the presence of an excess of base at a temperature on the order of 0° C. The reaction is typically conducted for between about 1 and about 3 hours or until the reaction is substantially complete.

Sulfonamide compounds in which $R^1$ is defined as —$S(O)_2R^9$ are typically prepared by contacting intermediate 1 with between about 1 and about 1.1 equivalents of a sulfonylchloride of the form Cl—$S(O)_2R^9$ in the presence of an excess of base at a temperature on the order of 0° C. The reaction is typically conducted for between about 1 and about 24 hours or until the reaction is substantially complete.

An exemplary reaction for the preparation of intermediate 1-2 in which the variables $R^2$, $R^3$, $R^4$, and $R^5$ are each hydrogen is illustrated in Scheme 2.

Scheme 2

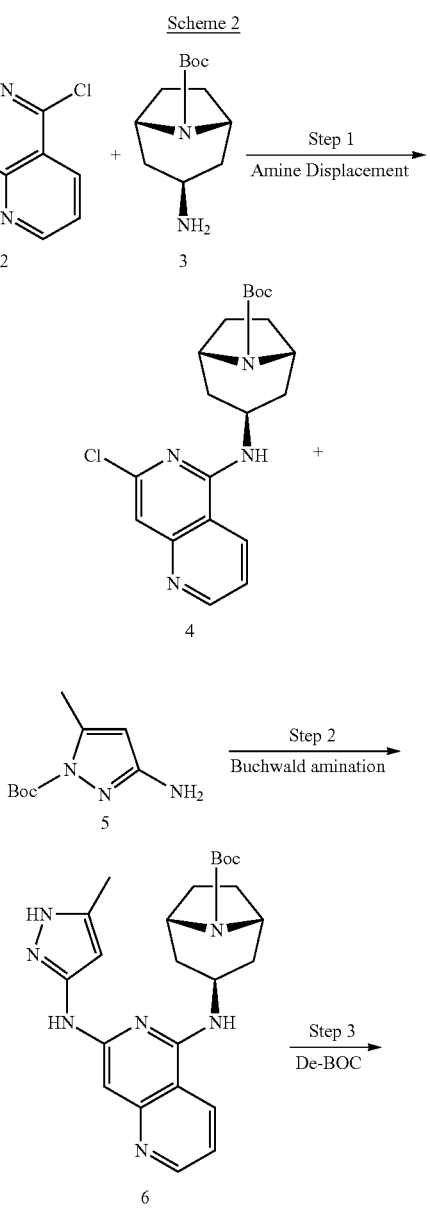

Scheme 3

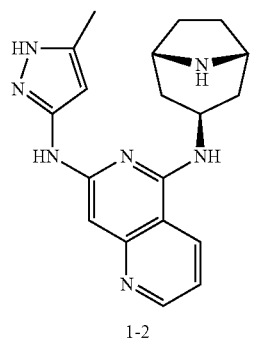

1-2

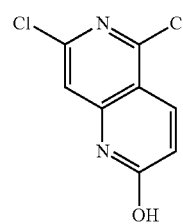

2-3

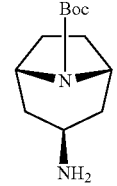

3

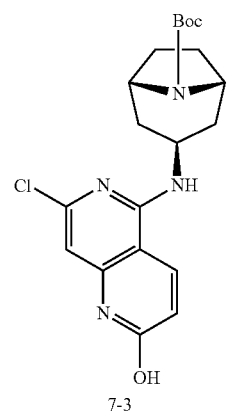

7-3

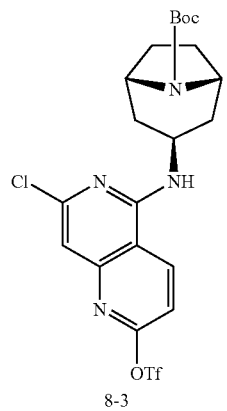

8-3

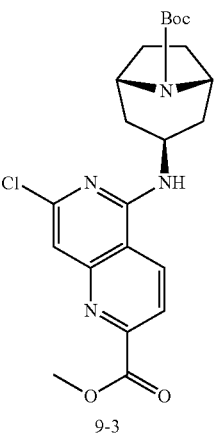

9-3

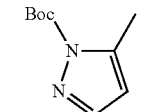

5

In the amine displacement reaction of step 1, the di-chloro-naphthyridine 2 is reacted with a slight excess of a tert-butoxycarbonyl (Boc)-protected amino-8-azabicyclo-[3.2.1]octane 3 in the presence of base to provide intermediate 4. The Boc-protected intermediate amino-methyl-pyrazole 5 is then reacted with intermediate 4 under standard Buchwald amination conditions. For example intermediate 4 is combined with between about 1 and about 1.5 equivalents of the pyrazole intermediate 5 in the presence of a base, such as cesium carbonate, and a palladium catalyst. The reaction is typically conducted at elevated temperature, between about 85° C. and about 110° C. for between about 24 and about 48 hours or until the reaction is substantially complete. The Boc protecting group may be removed from the methylpyrazole during the course of the Buchwald reaction, as shown in Scheme 2, or the Boc protecting group may remain on the methylpyrazole and be removed along with the protecting group on the 8-azabicylooctyl group in the final step. In the last step, the Boc group or groups may be removed by standard treatment with an acid, typically trifluoroacetic acid or hydrochloric acid in dioxane.

As described in the appended examples, the preparation of intermediate 1 in which one or more of $R^2$, $R^3$, $R^4$, and $R^5$ is other than hydrogen may follow the sequence of steps shown in Scheme 2, starting with a substituted di-chloro-naphthyridine reagent analogous to intermediate 2. The substituted intermediate 2 may be commercially available or easily prepared from commercial reagents by standard procedures.

It will be appreciated that compounds of the invention may be prepared by a variety of process routes in which reactants are combined in different orders to provide different intermediates en route to producing final products. For certain substituents, $R^2$, $R^3$, $R^4$, or $R^5$ it is preferable to start with a naphthyridine intermediate substituted with a precursor of the desired substituent, perform the amine displacement reaction to add the protected amino-8-azabicylooctyl group, and transform the precursor to the desired substituent or one step away from a desired substituent before adding the pyrazole group. One specific example, the process to form intermediate 6-3, the Boc-protected precursor to substituted intermediate 2 where $R^2$ is —CH$_2$OH and $R^3$, $R^4$, and $R^5$ are each hydrogen, is sketched in Scheme 3 below and described explicitly in Preparations 5 and 6.

-continued

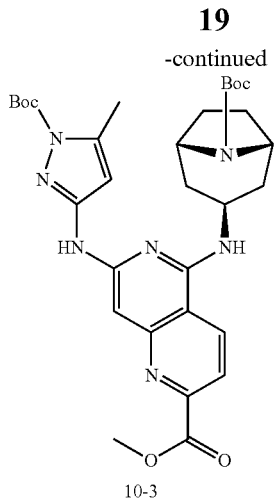

10-3

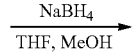

NaBH₄
THF, MeOH

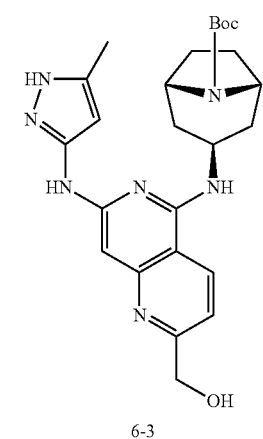

6-3

The protected amino-8-azabicylooctyl group 3 is added to a hydroxyl substituted di-chloro-naphthyridine 2-3 to form intermediate 7-3. With the 8-azabicylooctyl group installed, the hydroxyl substituent is successively transformed to the triflate, 8-3, and then to the methyl ester, 9-3, before adding the protected aminopyrazole 5 to form intermediate 10-3, which is hydrogenated to form the protected intermediate 6-3 bearing the $R^2$ substituent —CH₂OH.

Additional synthetic processes for preparation of compounds of the invention in which the substituents $R^2$, $R^3$, $R^4$ or $R^5$ are other than hydrogen and processes for the preparation of compounds in which the variable n is 2, are described in the examples below.

Accordingly, in a method aspect, the invention provides a method of preparing a compound of formula (I) or a pharmaceutically acceptable salt thereof, the method comprising reacting a compound of formula (IV):

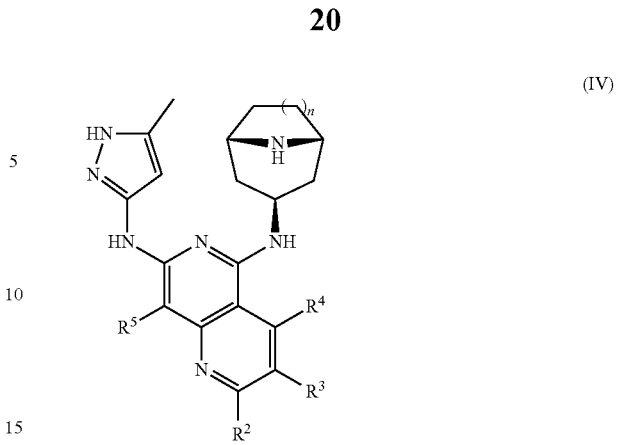

(IV)

with (i) a compound of formula L-$R^4$ wherein L is a leaving group and $R^4$ is an optionally substituted alkyl as defined for $R^1$ option (a) or a substituent of option (b), or (ii) HO—C(O)$R^6$, or (iii) Cl—C(O)O$R^8$, or (iv) Cl—S(O)₂$R^9$ to form a compound of formula (I) or a pharmaceutically acceptable salt thereof.

In separate and distinct aspects, the invention provides a compound of formula (IV) wherein the variables take any of the values described above and a compound of formula (IV) wherein $R^2$, $R^3$, $R^4$, and $R^5$ are each hydrogen.

Crystalline Forms

In another aspect, the invention provides 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile (Example 1) in crystalline freebase form or a solvate thereof.

Crystalline Form I of the invention is a crystalline freebase of the compound of Example 1. In one aspect, Form I is characterized by a powder X-ray diffraction (PXRD) pattern having significant diffraction peaks, among other peaks, at 2θ values of 7.87±0.20, 12.78±0.20, 15.78±0.20, and 20.41±0.20. Form I may be further characterized by a PXRD pattern having two or more additional diffraction peaks, including three or more and four or more additional diffraction peaks at 2θ values selected from 10.80±0.20, 13.47±0.20, 13.64±0.20, 14.66±0.20, 15.11±0.20, 15.54±0.20, 17.75±0.20, 21.00±0.20, 22.22±0.20, 22.93±0.20, and 23.65±0.20. In another aspect, Form I is characterized by a PXRD pattern having diffraction peaks at 2θ values of 7.87±0.20, 10.80±0.20, 12.78±0.20, 13.47±0.20, 13.64±0.20, 14.66±0.20, 15.11±0.20, 15.54±0.20, 15.78±0.20, 17.75±0.20, 20.41±0.20, 21.00±0.20, 22.22±0.20, 22.93±0.20, and 23.65±0.20.

As is well known in the field of powder X-ray diffraction, peak positions of PXRD spectra are relatively less sensitive to experimental details, such as details of sample preparation and instrument geometry, than are the relative peak heights. Thus, in one aspect, the crystalline Form I is characterized by a powder x-ray diffraction pattern in which the peak positions are substantially in accordance with those shown in FIG. 1.

The structure of crystalline Form I has been further characterized by single crystal x-ray diffraction analysis. The crystals belong to a monoclinic crystal system and P2₁/n space group. The unit cell dimensions are: a=8.8240(10) Å, b=22.4866(3) Å, c=10.2464(2) Å, α=90°, β=93.2360(10°), γ=90°, volume=2029.87(5) Å³. The calculated density is 1.317 g/cm³. The crystals contain four molecules per unit cell. The structure confirms that the crystals do not contain water or other solvent molecules and the molecular structure is consistent with the structure of the compound of Example 1 as depicted herein. Powder X-ray diffraction peaks predicted from the derived atomic positions are in excellent agreement with observed results.

Figure 2:
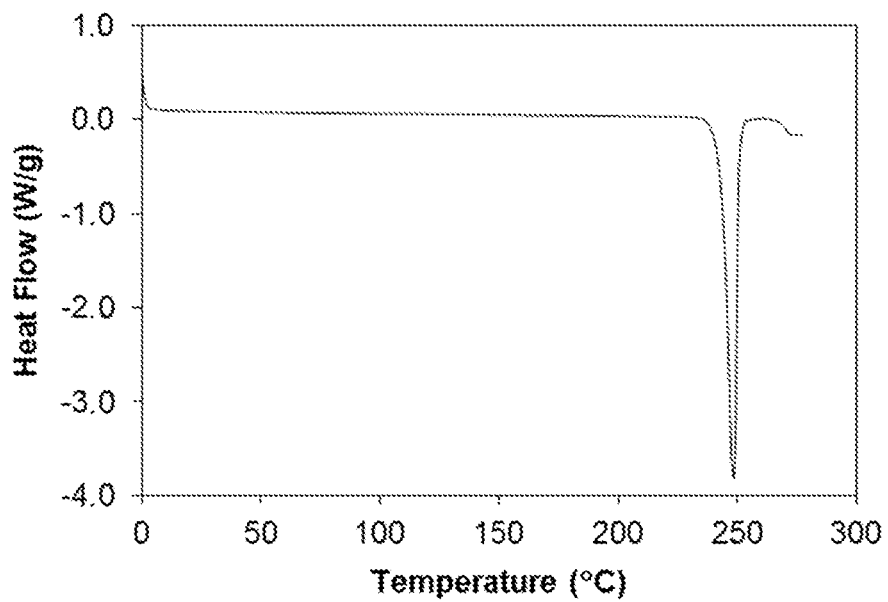
FIG. 2 shows a differential scanning calorimetry (DSC) thermogram of crystalline Form I.
Figure 3:
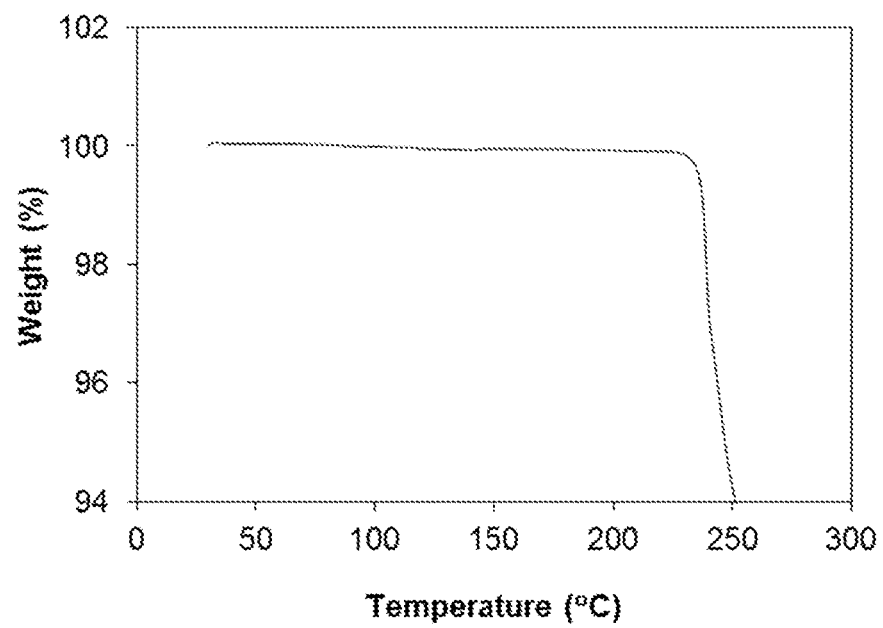
FIG. 3 shows a thermal gravimetric analysis (TGA) plot of crystalline Form I.

In another aspect, crystalline Form I is characterized by its behavior when exposed to high temperature. As demonstrated in FIG. 2, the differential scanning calorimetry (DSC) trace recorded at a heating rate of 10° C. per minute exhibits a peak in endothermic heat flow, identified as a melt transition, in the range of about 243° C. to about 253° C., including between about 246° C. and about 250° C. The thermal gravimetric analysis (TGA) trace of FIG. 3 shows no significant weight loss at temperatures below the onset of decomposition at about 237° C.

Figure 4:
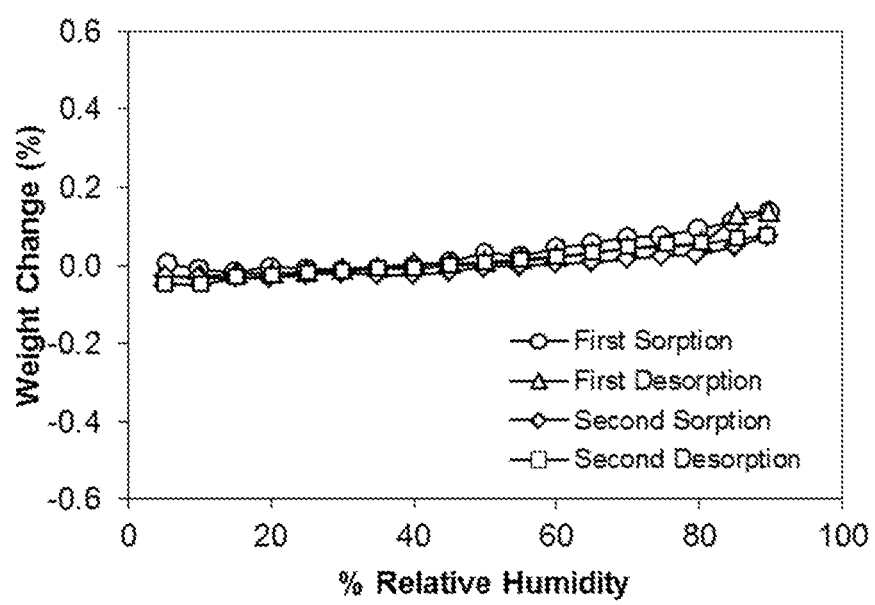
FIG. 4 shows a dynamic moisture sorption (DMS) isotherm of crystalline Form I observed at a temperature of about 25° C.

Crystalline Form I has been demonstrated to have a reversible sorption/desorption profile with an exceptionally small propensity for hygroscopicity. Form I demonstrated less than about 0.14% weight gain in the humidity range of 5% to 90% relative humidity and less than about 0.07% weight gain in the humidity range of 5% to 90% relative humidity at room temperature, as shown in FIG. 4. No hysteresis was observed in two cycles of sorption and desorption. Form I is considered to be non-hygroscopic.

Crystalline Form I has been shown to be stable upon exposure to elevated temperature and humidity. After 3 months at accelerated conditions of 40° C. and 75% relative humidity, no statistically significant changes in chemical content nor in impurity profile were observed.

Figure 5:
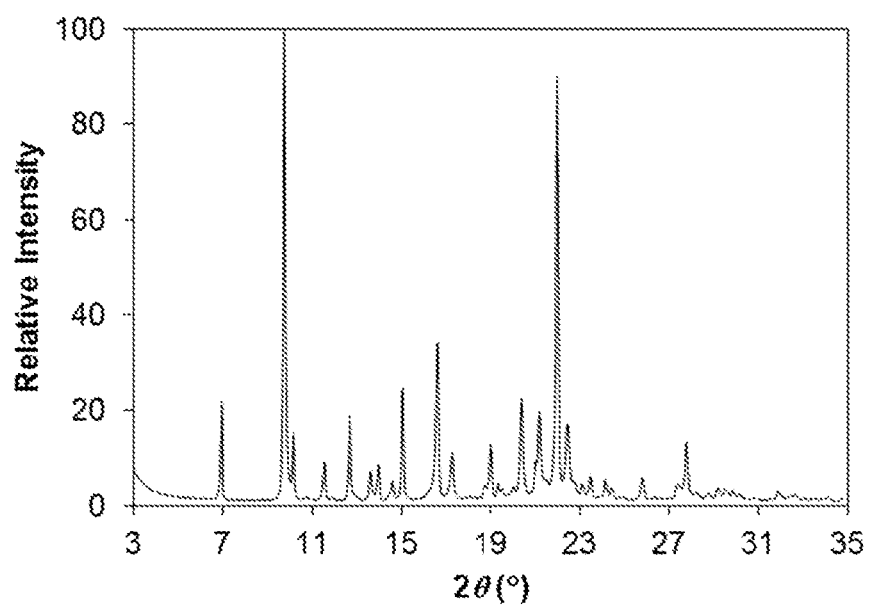
FIG. 5 shows a powder X-ray diffraction (PXRD) pattern of the crystalline Form II solvate 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile.

Crystalline Form II is a crystalline solvate of the compound of Example 1, characterized by the powder x-ray diffraction pattern of FIG. 5 with significant diffraction peaks, among other peaks, at 2θ values of 9.76±0.20, 15.06±0.20, 16.61±0.20, 20.40±0.20, and 21.99±0.20. As described in Example 18 below, the Form II solvate contains between about 6% and about 7% methanol, between about 2% and about 2.5% N,N-dimethylformamide, and between about 1 and about 1.5% water.

The solvate of Form II may be prepared by adding a mixture of methanol and water, typically a ratio of methanol to water between about 1.5:1 and about 3:1, to the product of the reaction of $N^5$-((1R,3s,5S)-8-azabicyclo[3.2.1]octan-3-yl)-$N^7$-(5-methyl-1H-pyrazol-3-yl)-1,6-naphthyridine-5,7-diamine (compound 1-2 in Scheme 2) with acrylonitrile or with bromopropionitrile, which is typically conducted in dimethylformamide. The resulting reaction mixture is stirred at a temperature of between about 20° C. and about 25° C. for between about 4 hours and about 24 hours, filtered, and washed with methanol or a mixture of methanol and water, such as a 1:1, 2:1, or 3:1 mixture of methanol and water to provide the Form II solvate. An ethanol solvate may be prepared by slurrying the Form II solvate in ethanol.

The non-solvated crystalline Form I is conveniently prepared from a solvate form of the compound of Example 1, preferably the solvate of Form II. In a typical process, the Form II solvate is typically combined with a non-protonating solvent to provide a slurry. Useful solvents include, but are not limited, to dioxane, toluene, butyl acetate, and acetone. The slurry is typically formed at a concentration of between about 50 mg solvate to milliliter of solvent and about 85 mg/mL. The slurry may be heated to a temperature of between about 40° C. and about 110° C. for between about 4 hours and about 3 days, filtered, and washed to provide the Form I crystalline solid. As described in Examples 19 and 20 below, acetone has been found to be a particularly useful solvent.

In another aspect, the invention provides a method of preparing crystalline Form I, the method comprising (a) forming a slurry of a crystalline solvate of 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile in a solvent selected from dioxane, toluene, butyl acetate, and acetone, (b) heating the slurry at a temperature between about 40° C. and about 110° C. for between about 4 hours and about 3 days, and (c) isolating crystalline Form I from the slurry.

Pharmaceutical Compositions

The compounds of the invention and pharmaceutically-acceptable salts thereof are typically used in the form of a pharmaceutical composition or formulation. Such pharmaceutical compositions may be administered to a patient by any acceptable route of administration including, but not limited to, oral, rectal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a compound of formula (I), where, as defined above, "compound of formula (I)" means a compound of formula (I) or a pharmaceutically-acceptable salt thereof. Optionally, such pharmaceutical compositions may contain other therapeutic and/or formulating agents if desired. When discussing compositions and uses thereof, the "compound of the invention" may also be referred to herein as the "active agent". As used herein, the term "compound of the invention" is intended to include all compounds encompassed by formula (I) as well as the species embodied in formulas (II) and (III) and pharmaceutically-acceptable salts thereof.

The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Maryland (2000); and H. C. Ansel et al., Pharmaceutical Dosage Forms and Drug Delivery Systems, 7th Edition, Lippincott Williams & White, Baltimore, Maryland (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, dicalcium phosphate, sucrose, glucose, mannitol, and/or silicic acid; binders, such as carboxymethylcellulose, hydroxypropylmethyl cellulose, alginates, gelatin, polyvinyl pyrrolidone, sucrose and/or acacia; humectants, such as glycerol; disintegrating agents, such as crosscarmellose sodium, crospovidone, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof, coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Alternatively, compounds of the invention may be administered in the form of suppositories. A typical suppository formulation will generally consist of active agent with a binding and/or lubricating agent such as a gelatin or cocoa butter or other low melting vegetable or synthetic wax or fat.

The following non-limiting examples illustrate representative pharmaceutical compositions of the present invention.

Tablet Oral Solid Dosage Form

A compound of the invention or a pharmaceutically-acceptable salt thereof is dry blended with microcrystalline cellulose, polyvinyl pyrrolidone, and croscarmellose sodium in a ratio of 4:5:1:1 and compressed into tablets to provide a unit dosage of, for example, 5 mg, 20 mg or 40 mg active agent per tablet.

Capsule Oral Solid Dosage Form

A compound of the invention or a pharmaceutically-acceptable salt thereof is combined with microcrystalline cellulose, polyvinyl pyrrolidone, and crosscarmellose sodium in a ratio of 4:5:1:1 by wet granulation and loaded into gelatin or hydroxypropyl methylcellulose capsules to provide a unit dosage of, for example, 5 mg, 20 mg or 40 mg active agent per capsule.

Tablet Oral Solid Dosage Form

A compound of the invention or a pharmaceutically-acceptable salt thereof is dry or wet granulated with microcrystalline cellulose, lactose, hydroxypropylmethyl cellulose, crospovidone, and magnesium stearate. The formulation composition in % wt/wt is compound of the invention (4%), microcrystalline cellulose (45%) lactose (36%), hydroxypropylmethyl cellulose (10%), crospovidone (3%), and magnesium stearate (2%). The dry or wet granulated blends are compressed into tablets to provide a unit dosage of 10 mg active agent per 250 mg tablet.

Tablet Oral Solid Dosage Form

A compound of the invention or a pharmaceutically-acceptable salt thereof is dry or wet granulated with microcrystalline cellulose, hydroxypropylmethyl cellulose, crospovidone, and magnesium stearate. The formulation composition in % wt/wt is compound of the invention (40%), microcrystalline cellulose (45%), hydroxypropylmethyl cellulose (10%), crospovidone (3%), and magnesium stearate (2%). The dry or wet granulated blends are compressed into tablets to provide a unit dosage of 100 mg active agent per 250 mg tablet.

Liquid Formulation

A liquid formulation comprising a compound of the invention (0.1%), water (98.9%) and ascorbic acid (1.0%) is formed by adding a compound of the invention to a mixture of water and ascorbic acid.

Enteric Coated Oral Dosage Form

A compound of the invention is dissolved in an aqueous solution containing polyvinyl pyrrolidone and spray coated onto microcrystalline cellulose or sugar beads in a ratio of 1:5 w/w active agent:beads and then an approximately 5% weight gain of an enteric coating comprising an acrylic copolymer, for example a combination of acrylic copolymers available under the trade names Eudragit-L® and Eudragit-S®, or hydroxypropyl methylcellulose acetate succinate is applied. The enteric coated beads are loaded into gelatin or hydroxypropyl methylcellulose capsules to provide a unit dosage of, for example, 30 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Utility

The compounds of the invention have been shown to be potent inhibitors of the JAK family of enzymes: JAK1, JAK2, JAK3, and TYK2. Inhibition of the family of JAK enzymes could inhibit signaling of many key pro-inflammatory cytokines. Thus the JAK inhibitors of the invention are expected to be useful in the treatment of inflammatory diseases such as ulcerative colitis, Crohn's disease, allergic rhinitis, asthma, and chronic obstructive pulmonary disease (COPD).

Compounds of the invention are designed to be poorly absorbed to minimize systemic exposure. As described in the experimental section below, the absorption and distribution of typical compounds has been extensively profiled in preclinical assays. Selected compounds tested in cannulated rats showed low absorption into plasma at the portal vein. In addition, the compounds are designed to have their effect at the site of action in the gastrointestinal tract. Selected compounds exhibited a ratio of exposure in the colon to exposure in plasma in rat greater than about 450. In particular, the compound of Example 1 has demonstrated significantly higher exposure throughout the gastrointestinal tract than exposure in plasma upon oral dosing in preclinical species. Furthermore, the compound of Example 1 has been evaluated in healthy human subjects and was found to exhibit high drug concentration in stool samples suggesting significant exposure in the gastrointestinal tract.

Oxazolone-induced colitis is an experimental model that has a histological resemblance to human ulcerative colitis. As described below, the compound of Example 1, among other compounds of the invention, demonstrated activity in the oxazolone-induced colitis model in mice. Further, when tested in an immunosuppression model in mice, which probes systemic functional activity, the compound demonstrated minimal effect of immunosuppression at the same dose required to demonstrate efficacy in the oxazolone model. Thus the compound demonstrated anti-colitic activity without exhibiting systemic effects in preclinical models.

It is expected that the high colon to plasma ratio achieved with these compounds will provide robust, luminally-driven anti-inflammatory activity without associated, systemically-driven, adverse effects. The compounds are expected to be useful for a variety of gastrointestinal inflammatory indications that include, but are not limited to, ulcerative colitis (proctosigmoiditis, pancolitis, ulcerative proctitis and left-sided colitis), Crohn's disease, collagenous colitis, lymphocytic colitis, Behcet's disease, celiac disease, checkpoint cancer treatment-induced colitis, (e.g. CTLA-4 inhibitor-induced colitis), ileitis, eosinophilic esophagitis, graft versus host disease-related colitis, and infectious colitis. Ulcerative colitis (Reimund et al., *J Clin Immunology,* 1996, 16, 144-150), Crohn's disease (Woywodt et al., *Eur J Gastroenterology Hepatology,* 1999, 11, 267-276), collagenous colitis (Kumawat et al., *Mol Immunology,* 2013, 55, 355-364), lymphocytic colitis (Kumawat et al., 2013), eosinophilic esophagitis (Weinbrand-Goichberg et al., *Immunol Res,* 2013, 56, 249-260), graft versus host disease-related colitis (Coghill et al., *Blood,* 2001, 117, 3268-3276), infectious colitis (Stallmach et al., *Int J Colorectal Dis,* 2004, 19, 308-315), Behcet's disease (Zhou et al., *Autoimmun Rev,* 2012, 11, 699-704), celiac disease (deNitto et al., *World J Gastroenterol,* 2009, 15, 4609-4614), checkpoint cancer treatment-induced colitis (e.g., CTLA-4 inhibitor-induced colitis; (Yano et al., *J Translation Med,* 2014, 12, 191), and ileitis (Yamamoto et al., *Dig Liver Dis,* 2008, 40, 253-259) are characterized by elevation of certain pro-inflammatory cytokine levels. As many pro-inflammatory cytokines signal via JAK activation, compounds described in this application may be able to alleviate the inflammation and provide symptom relief.

In particular, the compounds of the invention are expected to be useful for the induction and maintenance of remission of ulcerative colitis, and for the treatment of Crohn's disease, CTLA-4 inhibitor-induced colitis, and the gastrointestinal adverse effects in graft versus host disease.

In one aspect, therefore, the invention provides a method of treating a gastrointestinal inflammatory disease in a mammal (e.g., a human), the method comprising administering to the mammal a therapeutically-effective amount of a compound of the invention or of a pharmaceutical composition comprising a pharmaceutically-acceptable carrier and a compound of the invention.

The invention further provides a method of treating ulcerative colitis in a mammal, the method comprising administering to the mammal a therapeutically-effective amount of a compound of the invention or of a pharmaceutical composition comprising a pharmaceutically-acceptable carrier and a compound of the invention.

When used to treat gastrointestinal inflammatory disease, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating ulcerative colitis and other gastrointestinal inflammatory disorders are expected to range from about 1 to about 400 mg/day of active agent, including from about 5 to about 300 mg/day and from about 20 to about 70 mg per day of active agent for an average 70 kg human.

Combination Therapy

Compounds of the invention may also be used in combination with one or more agents which act by the same mechanism or by different mechanisms to effect treatment of gastrointestinal inflammatory disorders. Useful classes of agents for combination therapy include, but are not limited to, aminosalicylates, steroids, systemic immunosuppressants, anti-TNFα antibodies, anti-VLA-4 antibodies, anti-integrin α4β7 antibodies, anti-bacterial agents, and anti-diarrheal medicines.

Aminosalicylates that may be used in combination with the present JAK inhibitor compounds include, but are not limited to, mesalamine, osalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin α4β7 antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, *Gut,* 2012, 61, 918-932; Lam et al., *Immunotherapy,* 2014, 6, 963-971.)

In another aspect, therefore, the invention provides a therapeutic combination for use in the treatment of gastrointestinal inflammatory disorders, the combination comprising a compound of the invention and one or more other therapeutic agents useful for treating gastrointestinal inflammatory disorders. For example, the invention provides a combination comprising a compound of the invention and one or more agents selected from aminosalicylates, steroids, systemic immunosuppressants, anti-TNFα antibodies, anti-VLA-4 antibodies, anti-integrin α4β7 antibodies, anti-bacterial agents, and anti-diarrheal medicines. Secondary agent(s), when included, are present in a therapeutically effective amount, i.e. in any amount that produces a therapeutically beneficial effect when co-administered with a compound of the invention.

Also provided, therefore, is a pharmaceutical composition comprising a compound of the invention and one or more other therapeutic agents useful for treating gastrointestinal inflammatory disorders.

Further, in a method aspect, the invention provides a method of treating gastrointestinal inflammatory disorders, the method comprising administering to the mammal a compound of the invention and one or more other therapeutic agents useful for treating gastrointestinal inflammatory disorders.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

Compounds of the invention have been demonstrated to be potent inhibitors of the JAK1, JAK2, JAK3, and TYK2 enzymes in enzyme binding assays and to have potent functional activity without cytotoxicity in cellular assays, as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
DCM=dichloromethane
DIPEA=N,N-diisopropylethylamine
DMF=N,N-dimethylformamide
DMSO=dimethyl sulfoxide
EtOAc=ethyl acetate
h=hour(s)
HATU=N,N,N',N'-tetramethyl-O-(7-azabenzotriazol-1-yl)uronium hexafluorophosphate
min=minute(s)
NMP=N-methyl-2-pyrrolidone
Pd(dppf)Cl$_2$=dichloro(1,1'-bis(diphenylphosphino)-ferrocene)dipalladium(II)
Pd$_2$(dba)$_3$=tris(dibenzylideneacetone)dipalladium(0)
PdXPhos=chloro(2-dicyclohexylphosphino-2',4',6'-triisopropyl-1,1'-biphenyl)[2-(2'-amino-1,1'-biphenyl)]palladium(II)
RT=room temperature
Selectfluor=1-chloromethyl-4-fluoro-1,4-diazoniabicyclo[2.2.2]octane bis(tetrafluoroborate)
TEA=triethylamine
TFA=trifluoroacetic acid
THF=tetrahydrofuran
bis(pinacolato)diboron=4,4,5,5,4',4',5',5'-octamethyl-[2,2']bi[[1,3,2]dioxaborolanyl]
Xantphos=4,5-bis(diphenylphosphino)-9,9-dimethylxanthene
Xphos=dicyclohexylphosphino-2',4',6'-triisopropylbiphenyl Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as CD$_3$OD, CDCl$_3$, or d$_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, CA) model API 150 EX instrument or a Waters (Milford, MA) 3100 instrument, coupled to autopurification systems.

Preparative HPLC Conditions
Method 1
  Column: C18, 5 μm 21.2×150 mm or C18, 5 μm 21×250 mm or C14 5 μm 21×150 mm
  Column temperature: Room Temperature
  Flow rate: 20.0 mL/min
  Mobile Phases: A=Water+0.05% TFA
    B=ACN+0.05% TFA,
  Injection volume: (100-1500 μL)
  Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 μL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Preparative HPLC Conditions
Method 2
  Column: Synergi 200×50 mm 10 μm
  Column temperature: Room Temperature
  Flow rate: 80 mL/min
  Mobile Phases: A=Water+0.1% TFA
    B=ACN
  Injection volume: 8 mL
  Detector wavelength: 220 nm and 254 nm
  Gradient: 25% to 45% B Analytic HPLC Conditions
Method 3
  Column: LUNA C18 (2), 150×4.60 mm, 3 μm
  Column temperature: 37° C.
  Flow rate: 1.0 mL/min
  Injection volume: 5 μL
  Sample preparation: Dissolve in 1:1 ACN:water
  Mobile Phases: A=Water:ACN:TFA (98:2:0.05)
    B=Water:ACN:TFA (2:98:0.05)
  Detector wavelength: 254 nm
  Gradient: 30 min total (time (min)/% B): 0/2, 10/20, 24/90, 26/90, 27/2, 30/2

Preparation 1: tert-butyl (1R,3s,5S)-3-((7-chloro-1,6-naphthyridin-5-yl)amino)-8-azabicyclo[3.2.1]octane-8-carboxylate

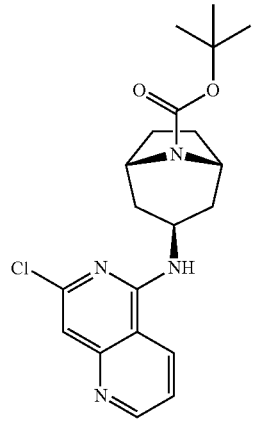 [SMILES: CC(C)(C)OC(=O)N1[C@@H]2CC[C@H]1C[C@H](Nc1nc(Cl)cc3ncccc13)C2]

To a 20 mL vial was added 5,7-dichloro-1,6-naphthyridine, (289.1 mg, 1.45 mmol), tert-butyl (1R,3s,5S)-3-amino-8-azabicyclo[3.2.1]octane-8-carboxylate (362 mg, 1.60 mmol), DIPEA (0.76 mL, 4.36 mmol), and DMSO (7.26 mL). The vial was capped and the reaction mixture was heated to 110° C. and stirred for 16 h. The reaction mixture was diluted with water and extracted with EtOAc (3×20 mL). The combined organic fractions were dried over sodium sulfate, filtered, and concentrated to afford a brown oil, which was purified by column chromatography (24 g column; 0-80% EtOAc in hexanes) to afford the title product as a pale yellow solid (455.2 mg, 69% yield; 85% purity). (m/z): [M+H]$^+$ calcd for $C_{20}H_{25}ClN_4O_2$ 389.17, 391.16. found 391.5.

Preparation 2: $N^5$-((1R,3s,5S)-8-azabicyclo[3.2.1]
octan-3-yl)-$N^7$-(5-methyl-1H-pyrazol-3-yl)-1,6-
naphthyridine-5,7-diamine

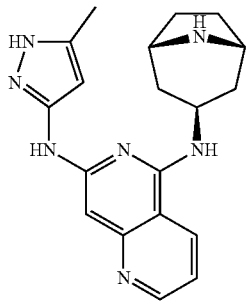 [SMILES: Cc1cc(Nc2cc3ncccc3c(N[C@@H]3C[C@H]4CC[C@@H](C3)N4)n2)n[nH]1]

(a) tert-butyl (1R,3s,5S)-3-((7-((1-(tert-butoxycarbonyl)-5-methyl-1H-pyrazol-3-yl)amino)-1,6-naphthyridin-5-yl)amino)-8-azabicyclo[3.2.1]octane-8-carboxylate To a 20 mL vial was added tert-butyl (1R,3s,5S)-3-((7-chloro-1,6-naphthyridin-5-yl)amino)-8-azabicyclo[3.2.1]octane-8-carboxylate (474.6 mg, 1.22 mmol), tert-butyl 3-amino-5-methyl-1H-pyrazole-1-carboxylate (289 mg, 1.46 mmol), chloro[2-(dicyclohexylphosphino)-3,6-dimethoxy-2'-4'-6'-tri- (58 mg, 0.073 mmol), and cesium carbonate (517 mg, 1.59 mmol). The vial was sealed with a rubber septum and the atmosphere was flushed with nitrogen. Dioxane (6.10 mL) was then added via syringe, and the septum was quickly replaced with a white cap. The reaction mixture was heated to 110° C. and stirred for 26 h and cooled to RT. The suspension was diluted with water and brine and extracted with EtOAc (4×20 mL). The combined organic fractions were dried over sodium sulfate, filtered, and concentrated to afford a brown foamy solid which was used directly in the next step. (m/z): [M+H]$^+$ calcd for $C_{29}H_{39}N_7O_4$ 550.31. found 550.8.

(b) $N^5$-((1R,3s,5S)-8-azabicyclo[3.2.1]octan-3-yl)-
$N^7$-(5-methyl-1H-pyrazol-3-yl)-1,6-naphthyridine-5,
7-diamine To the product of the previous step (671 mg, 1.22 mmol) was added DCM (3.05 mL) followed by TFA (3.05 mL) and the reaction mixture was stirred at RT for 4 h and concentrated to afford a thick, red oil. The crude oil was dissolved in a 15% solution of acetic acid in water including 0.1 mL ACN (10 mL) and purified by preparative HPLC (method 1) to afford the di-TFA salt of the title product as a red/orange solid (705 mg, 73% yield; 97% purity). (m/z): [M+H]$^+$ calcd for $C_{19}H_{23}N_7$ 350.20. found 350.5.

Preparation 3: tert-butyl (1R,3s,5S)-3-((7-chloro-1,
6-naphthyridin-5-yl)amino)-9-azabicyclo[3.3.1]
nonane-9-carboxylate

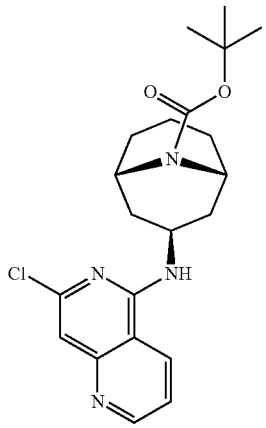 [SMILES: CC(C)(C)OC(=O)N1[C@@H]2CCC[C@H]1C[C@H](Nc1nc(Cl)cc3ncccc13)C2]

To a 40 mL vial was added 5,7-dichloro-1,6-naphthyridine, (510 mg, 2.56 mmol), tert-butyl (1R,3s,5S)-3-amino-9-azabicyclo[3.3.1]nonane-9-carboxylate (677 mg, 2.82 mmol), DIPEA (1.34 mL, 7.69 mmol), and DMSO (8.54 mL). The vial was capped and the reaction mixture was heated to 110° C. and stirred for 16 h. The reaction mixture was diluted with water and brine and extracted with EtOAc (4×30 mL). The combined organic fractions were dried over sodium sulfate, filtered, and concentrated to afford the desired product as a brown solid which was dissolved in a minimal amount of DCM and adsorbed onto Celite®, purified by column chromatography (40 g column; 0-100% EtOAc in hexanes) to afford the title product as a yellow solid (901.6 mg, 86% yield; 99% purity). (m/z): [M+H]$^+$ calcd for $C_{21}H_{27}ClN_4O_2$ 403.18. found 403.3.

Preparation 4: $N_5$-((1R,3s,5S)-9-azabicyclo[3.3.1]
nonan-3-yl)-$N^7$-(5-methyl-1H-pyrazol-3-yl)-1,6-
naphthyridine-5,7-diamine

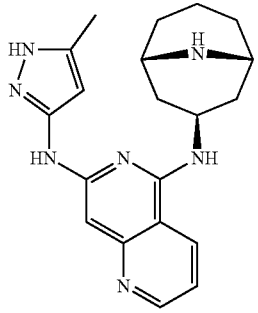 [SMILES: Cc1cc(Nc2cc3ncccc3c(N[C@@H]3C[C@H]4CCC[C@@H](C3)N4)n2)n[nH]1]

(a) tert-butyl (1R,3s,5S)-3-((7-((1-(tert-butoxycarbonyl)-5-methyl-1H-pyrazol-3-yl)amino)-1,6-naphthyridin-5-yl)amino)-9-azabicyclo[3.3.1]nonane-9-carboxylate To a 100 mL round bottom flask was added the product of Preparation 3 (876.4 mg, 2.18 mmol), tert-butyl 3-amino- 5-methyl-1H-pyrazole-1-carboxylate (515 mg, 2.61 mmol), chloro[2-(dicyclohexylphosphino)-3,6-dimethoxy-2'-4'-6'-tri-iso-propyl-1,1'-biphenyl][2-(2-aminoethyl)phenyl]palladium(II) methyl tert-butylether adduct (104 mg, 0.131 mmol), and cesium carbonate (921 mg, 2.83 mmol). The flask was sealed with a rubber septum and the atmosphere was flushed with nitrogen. Dioxane (21.75 mL) was added via syringe. A condenser with an attached nitrogen balloon was added to the flask, and the reaction mixture was heated to 110° C. and stirred for 20 h. The reaction mixture was cooled to RT, diluted with brine, and extracted with EtOAc (4×30 mL). The combined organic fractions were dried over sodium sulfate, filtered, and concentrated to afford a crude brown solid, which was used in the next step without further purification.

(b) $N^5$-((1R,3s,5S)-9-azabicyclo[3.3.1]nonan-3-yl)-$N^7$-(5-methyl-1H-pyrazol-3-yl)-1,6-naphthyridine-5,7-diamine To the product of the previous step (1.226 g, 2.175 mmol) was added DCM (5.44 mL) and TFA (5.44 mL). The flask was covered with a rubber septum pierced with a needle. The solution was stirred at RT for 4 h and concentrated to afford a dark, red oil. The crude material was dissolved in a 3:1:0.25 water:acetic acid:acetonitrile solution (18 mL), filtered, and purified in two batches by preparative HPLC to afford the 2TFA salt of the title product as a red solid (991.1 mg, 75% yield; 97% purity). (m/z): $[M+H]^+$ calcd for $C_{20}H_{25}N_7$ 364.22. found 364.1.

Preparation 5: 5,7-dichloro-1,6-naphthyridin-2-ol

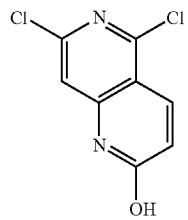 [SMILES: Oc1ccc2c(Cl)nc(Cl)cc2n1]

(a) N-(2,6-dichloropyridin-4-yl)pivalamide

To a mixture of 2,6-dichloropyridin-4-amine (80.0 g, 491 mmol) and TEA (99.8 g, 982 mmol) in DCM (800 mL) was added pivaloyl chloride (118.0 g, 982 mmol) at 0° C., and the mixture was stirred at 20° C. for 13 h, filtered, extracted with DCM, washed with brine, dried over $Na_2SO_4$, filtered, concentrated in vacuo, and then purified by recrystallization from DCM to afford the title intermediate as a white solid (90 g, 70% yield).

(b) N-(2,6-dichloro-3-formylpyridin-4-yl)pivalamide

To a mixture of the product of the previous step (24.0 g, 97.1 mmol) in THF (250 mL) was added tert-butyl lithium (224 mL, 291.3 mmol) at −78° C., and the reaction mixture was stirred at −78° C. for 1.5 h. DMF (22.7 g, 291.3 mmol) was added, the reaction mixture was stirred at −78° C. for 3 h and 6 M HCl was added. The reaction mixture was extracted with EtOAc, washed with brine, dried, concentrated, and purified by column chromatography. The products of three identical reactions were combined to afford the title intermediate (36 g, 45% yield).

(c) tert-butyl 3-(2,6-dichloro-4-pivalamidopyridin-3-yl)-3-hydroxypropanoate

Diisopropylamine (17.2 g, 170.8 mmol) was dissolved in THF (100 mL) and cooled to −78° C., and then n-butyl lithium (68.3 mL, 170.8 mmol) was added dropwise at −78° C. The mixture was stirred at −78° C. for 0.5 h and then tert-butyl acetate (19.8 g, 170.8 mmol) dissolved in THF (100 mL) was added dropwise at −78° C. The reaction mixture was stirred at −78° C. for 0.5 h and then the product of the previous step (18 g, 65.7 mmol) dissolved in THF (150 mL) was added dropwise at −78° C. and the mixture was stirred at −78° C. for 1.0 h. Aqueous ammonium chloride was added and the reaction mixture was extracted with EtOAc (2×800 mL). The organic layer was dried and evaporated and the residue was purified by column chromatography. The products of two identical reactions were combined to provide the title intermediate as a white solid (58 g).

(d) 5,7-dichloro-1,6-naphthyridin-2-ol

Aqueous HCl (400 mL) was added to tert-butyl 3-(2,6-dichloro-4-pivalamidopyridin-3-yl)-3-hydroxypropanoate (64 g, 164 mmol) dissolved in dioxane (400 mL) and the reaction mixture was stirred at 100° C. for 12 h. Water was added and the reaction mixture was filtered to give the title intermediate as a white solid (33 g, 94% yield).

Preparation 6: tert-butyl (1R,3s,5S)-3-((2-(hydroxymethyl)-7-((5-methyl-1H-pyrazol-3-yl)amino)-1,6-naphthyridin-5-yl)amino)-8-azabicyclo[3.2.1]octane-8-carboxylate

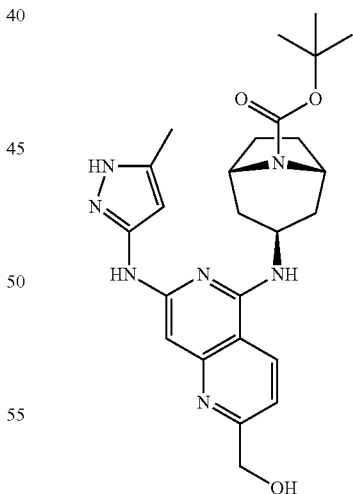

(a) tert-butyl (1R,3s,5S)-3-((7-chloro-2-hydroxy-1,6-naphthyridin-5-yl)amino)-8-azabicyclo[3.2.1]octane-8-carboxylate To a mixture of 5,7-dichloro-1,6-naphthyridin-2-ol (7.0 g, 32.5 mmol) and tert-butyl (1R,3s,5S)-3-amino-8-azabicyclo[3.2.1]octane-8-carboxylate (8.1 g, 35.8 mmol) in DMSO (70 mL) was added DIPEA (8.4 g, 65.0 mmol), The reaction mixture was heated to 110° C. for 8 h, poured into water, filtered, and washed with EtOAc (200 mL) to give the title intermediate as a yellow solid (10 g, 75% yield).

(b) tert-butyl (1R,3s,5S)-3-((7-chloro-2-(((trifluoromethyl)sulfonyl)oxy)-1,6-naphthyridin-5-yl)amino)-8-azabicyclo[3.2.1]octane-8-carboxylate To a solution of the product of the previous step (10 g, 24 mmol) and cesium carbonate (15.6 g, 48 mmol) in DMF (100 mL) was added dropwise a solution of N-phenyl-bis(trifluoromethanesulfonimide) (17.0 g, 48 mmol) in DMF (100 mL) at 0° C., and the reaction mixture was stirred at 20° C. for 2 h. Water (200 mL) was added and the reaction mixture was extracted with EtOAc (400 mL), washed with brine (100 mL), dried over sodium sulfate, and concentrated to provide the crude title intermediate (14 g), which was used directly in the next step.

(c) Methyl 5-(((1R,3s,5S)-8-(tert-butoxycarbonyl)-8-azabicyclo[3.2.1]octan-3-yl)amino)-7-chloro-1,6-naphthyridine-2-carboxylate To a solution of the product of the previous step (14 g, 26 mmol) in MeOH (280 mL) were added Pd(dppf)Cl$_2$ (2.0 g, 2.6 mmol) and TEA (5.3 g, 52 mmol) and the reaction mixture was heated to 50° C. for 12 h under CO atmosphere (50 psi). The reaction mixture was filtered, diluted with water (100 mL), extracted with EtOAc (300 mL), washed with brine (50 mL), dried over sodium sulfate, concentrated and purified by column chromatography to provide the title intermediate (8.0 g, 70% yield).
(m/z): [M+H]$^+$ calcd for C$_{22}$H$_{27}$ClN$_4$O$_4$ 447.17. found 447.1.

(d) Methyl 7-((1-(tert-butoxycarbonyl)-5-methyl-1H-pyrazol-3-yl)amino)-5-(((1R,3s,5S)-8-(tert-butoxycarbonyl)-8-azabicyclo[3.2.1]octan-3-yl)amino)-1,6-naphthyridine-2-carboxylate To a mixture of the product of the previous step (8.0 g, 17.8 mmol), tert-butyl 3-amino-5-methyl-1H-pyrazole-1-carboxylate (4.5 g, 21.5 mmol) and cesium carbonate (7.1 g, 21.5 mmol) in dioxane (80 mL) was added PdXPhos (2.8 g, 3.56 mmol) under nitrogen. The reaction mixture was stirred at 100° C. for 12 h, diluted with EtOAc (150 mL), washed with water (50 mL) and brine (30 mL), dried over anhydrous sodium sulfate, concentrated, and purified by column chromatography to provide the title intermediate (3.0 g, 72% yield). (m/z): [M+H]$^+$ calcd for C$_{31}$H$_{41}$N$_7$O$_6$ 608.31. found 608.3.

(e) tert-butyl (1R,3s,5S)-3-((2-(hydroxymethyl)-7-((5-methyl-1H-pyrazol-3-yl)amino)-1,6-naphthyridin-5-yl)amino)-8-azabicyclo[3.2.1]octane-8-carboxylate To a solution of sodium borohydride (225 mg, 5.91 mmol) in MeOH (565 mg, 17.6 mmol) and THF (10 mL) was added a solution of the product of the previous step (500 mg, 0.98 mmol) in THF (40 mL) at 0° C., and the reaction mixture was stirred at 50° C. for 2 h. Water (15 mL) was added, followed by EtOAc (150 mL). The reaction mixture was washed with brine (30 mL), dried over anhydrous sodium sulfate, concentrated and purified by preparative HPLC (method 2) to afford the title product (840 mg, 46% yield). (m/z): [M+H]$^+$ calcd for C$_{25}$H$_{33}$N$_7$O$_3$ 480.26. found 480.2.

Preparation 7:
2-(Bromomethyl)-5,7-dichloro-1,6-naphthyridine

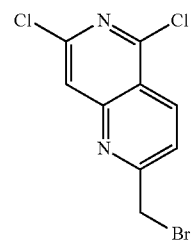 [SMILES: Clc1cc2nc(CBr)ccc2c(Cl)n1]

(a) 2-(2-ethoxy-2-oxoethyl)-6-methylnicotinic Acid

To a mixture of potassium tert-butoxide (90.2 g, 804 mmol) in isopropyl alcohol (600 mL) was added ethyl acetoacetate (69.8 g, 536 mmol). The reaction mixture was stirred at RT for 1 h, then copper acetate (4.8 g, 26.8 mmol) was added, followed by 2-chloro-6-methylnicotinic acid (46.0 g, 268 mmol) and the reaction mixture was stirred at 80° C. for 5 h, dilute HCl was added to adjust the pH to 2 and the solution was extracted with EtOAc (3×500 mL). The combined organic layers were washed with brine, dried, and concentrated to give crude product, which was recrystallized with 5:1 petroleum ether:toluene to give the title intermediate as a brown solid (47 g, 79% yield).

(b) 2-Methyl-1,6-naphthyridine-5,7(6H,8H)-dione

To a solution of the product of the previous step (25 g, 105.5 mmol) in THF (250 mL) was added TEA (15.9 g, 158.2 mmol). The mixture was cooled to −10° C. and ethyl chloroformate (17.2 g, 158.2 mmol) was added, and the reaction mixture was stirred for 1 h at −10-5° C. Ammonium hydroxide (200 mL) was added dropwise at 0-5° C. and the reaction mixture was stirred for 2 h at RT. The products of two identical reactions were combined and the reaction mixture was adjusted to pH 6.5-7.5 with 3 M HCl, concentrated under vacuum, stirred for 1 h at −10-5° C., filtered, and dried under vacuum to give the title intermediate as a brown solid (30 g crude). (m/z): [M+H]$^+$ calcd for C$_9$H$_8$N$_2$O$_2$ 177.07. found 177.1.

(c) 5,7-dichloro-2-methyl-1,6-naphthyridine

The product of the previous step (10.0 g, 56.7 mmol) was dissolved in phosphoryl chloride (40 mL) and stirred for 6 h at 160° C. in a 100 mL sealed tube. The phosphoryl chloride was removed by reduced pressure distillation and the reaction mixture was poured into ice/water (400 mL) and extracted with DCM (3×400 mL), The organic layers were combined, washed with brine, dried over Na$_2$SO$_4$, concentrated, and the residue was purified by flash chromatography to give the title intermediate product as a red solid (3.4 g, 28% yield).

(d) 2-(Bromomethyl)-5,7-dichloro-1,6-naphthyridine

To a solution of 5,7-dichloro-2-methyl-1,6-naphthyridine (5.0 g, 23.4 mmol) in carbon tetrachloride (100 mL) was added N-bromosuccinimide (4.17 g, 23.4 mmol) and benzoyl peroxide (0.28 g, 1.2 mmol) and the reaction mixture was heated at reflux for 12 h and concentrated to give the crude product which was purified by silica gel chromatography to provide the title compound as a red solid (3.8 g, 55% yield).

(m/z): [M+H]$^+$ calcd for $C_9H_5BrCl_2N_2$ 290.90. found 290.9.

Preparation 8: tert-butyl (1R,3s,5S)-3-((7-chloro-2-(morpholinomethyl)-1,6-naphthyridin-5-yl)amino)-8-azabicyclo[3.2.1]octane-8-carboxylate

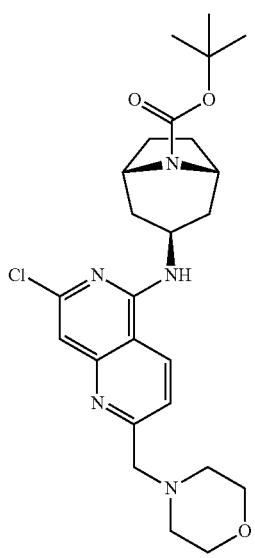 [SMILES: CC(C)(C)OC(=O)N1[C@@H]2CC[C@H]1C[C@H](Nc1nc(Cl)cc3nc(CN4CCOCC4)ccc13)C2]

(a) 4-((5,7-dichloro-1,6-naphthyridin-2-yl)methyl)morpholine

To a solution of 2-(bromomethyl)-5,7-dichloro-1,6-naphthyridine (1.0 g, 3.43 mmol) in ACN (34.3 mL) was added DIPEA (1.79 mL, 10.28 mmol) followed by morpholine (0.31 mL, 3.60 mmol) at 0° C. The mixture was stirred at 0° C. to RT overnight, filtered through a pad of Celite®, which was washed with EtOAc. The combined organic fractions were concentrated by rotary evaporation to give crude title product, which was used in the next step without purification. (m/z): [M+H]$^+$ calcd for $C_{13}H_{13}Cl_2N_3O_2$ 298.04. found 298.0.

(b) tert-butyl (1R,3s,5S)-3-((7-chloro-2-(morpholinomethyl)-1,6-naphthyridin-5-yl)amino)-8-azabicyclo[3.2.1]octane-8-carboxylate To a mixture of the product of the previous step (1020 mg, 3.42 mmol) and tert-butyl (1R,3s,5S)-3-amino-8-azabicyclo[3.2.1]octane-8-carboxylate (774 mg, 3.42 mmol) in DMSO (34.3 mL) was added DIPEA (1.787 mL, 10.26 mmol) at RT. The resulting mixture was stirred at 120° C. for 19 h. Solvent was removed by rotary evaporation to give crude product, which was purified by column chromatography to give the title compound as a brown solid (513 mg, 30.7% yield). (m/z): [M+H]$^+$ calcd for $C_{25}H_{34}ClN_5O_3$ 488.24. found 488.2.

Preparation 9: 5,7-dichloro-2-((4,4-difluoropiperidin-1-yl)methyl)-1,6-naphthyridine

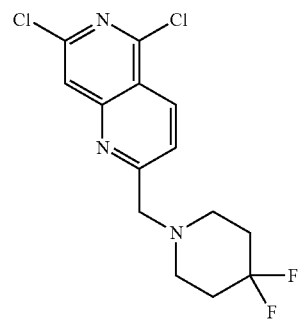 [SMILES: FC1(F)CCN(Cc2ccc3c(Cl)nc(Cl)cc3n2)CC1]

Following the general procedure of Preparation 8(a), substituting 4,4-difluoropiperidine for morpholine, the title intermediate was obtained. (m/z): [M+H]$^+$ calcd for $C_{14}H_{13}Cl_2F_2N_3$ 332.05. found 332.0.

Preparation 10: 5,7-dichloro-2-((4-methylpiperazin-1-yl)methyl)-1,6-naphthyridine

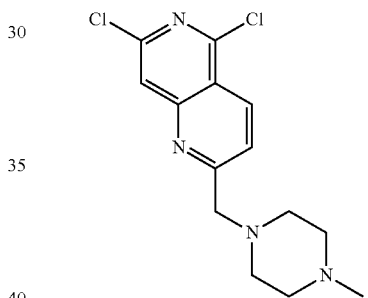

Following the general procedure of Preparation 8(a), substituting 1-methylpiperazine for morpholine, the title intermediate was obtained. (m/z): [M+H]$^+$ calcd for $C_{14}H_{16}Cl_2N_4$ 311.08. found 311.0.

Preparation 11: 5,7-dichloro-3-methoxy-1,6-naphthyridine

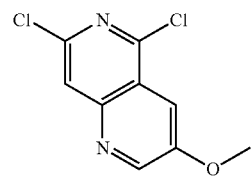

(a) 5,7-Dichloro-3-iodo-1,6-naphthyridine

A mixture of 5,7-dichloro-1,6-naphthyridine (4.0 g, 20 mmol) and N-iodosuccinimide (9.0 g, 37 mmol) in acetic acid (100 mL) was heated at reflux for 12 h. The reaction mixture was concentrated under vacuum, and the residue was purified by column chromatography 20:1 petroleum ether:EtOAc to provide the title intermediate as a yellow solid (2.4 g, 37% yield).

(b) (5,7-Dichloro-1,6-naphthyridin-3-yl)boronic Acid

To a solution of 5,7-dichloro-3-iodo-1,6-naphthyridine (6.0 g, 18.5 mmol), bis(pinacolato)diborane (5.2 g, 20.4 mmol) and potassium acetate (3.6 g, 37.0 mmol) in dioxane (50 mL) was added Pd(dppf)$_2$Cl$_2$ (0.6 g) under nitrogen. The reaction mixture was heated at 90° C. overnight and filtered. The filtrate was concentrated to provide the title intermediate as a yellow oil (6 g, crude).

(c) 5,7-Dichloro-1,6-naphthyridin-3-ol

The product of the previous step (6 g, crude) was dissolved in DCM (20 mL), and hydrogen peroxide (6 mL) was added at 0° C. The reaction mixture was stirred at RT overnight and then an aqueous solution of sodium thiosulfate (20 mL) was added to the mixture at 0° C. The mixture was extracted with DCM; the combined organic layers were washed with brine, dried with Na$_2$SO$_4$, and concentrated, to provide the title intermediate as a yellow solid (6.0 g, crude).

(d) 5,7-Dichloro-3-methoxy-1,6-naphthyridine

To a mixture of the product of the previous step (6.0 g, 27.9 mmol) and potassium carbonate (30.6 g, 83.7 mmol) in DMF (50 mL) was added methyliodide (14.4 g, 101 mmol) at RT. The reaction mixture was stirred at RT for 2 h, diluted with water (50 mL), extracted with EtOAc (3×100 mL), washed with brine (2×30 mL), dried over Na$_2$SO$_4$, filtered and concentrated under vacuum. The residue was purified by column chromatography to provide the title compound as a yellow solid (3.0 g, 46% yield).

Preparation 12: Methyl 5-(((1R,3s,5S)-8-azabicyclo[3.2.1]octan-3-yl)amino)-7-((5-methyl-1H-pyrazol-3-yl)amino)-1,6-naphthyridine-3-carboxylate

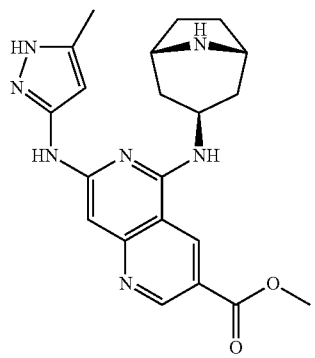 [SMILES: COC(=O)c1cnc2cc(Nc3cc(C)[nH]n3)nc(N[C@@H]3C[C@H]4CC[C@@H](C3)N4)c2c1]

(a) tert-Butyl(1R,3s,5S)-3-((7-chloro-3-iodo-1,6-naphthyridin-5-yl)amino)-8-azabicyclo[3.2.1]octane-8-carboxylate A solution of 5,7-dichloro-3-iodo-1,6-naphthyridine (7.0 g, 21.6 mol), DIPEA (5.6 g, 43.2 mmol) and tert-butyl (1R,3s,5S)-3-amino-8-azabicyclo[3.2.1]octane-8-carboxylate (5.8 g, 25.9 mmol) dissolved in NMP (70 mL) was heated at 110° C. for 3 h. The reaction mixture was purified by column chromatography (eluted with EtOAc:petroleum ether 0-20%) to give the title intermediate as a yellow solid (10.2 g, 91.8% yield).

(b) Methyl 5-(((1R,3s,5S)-8-(tert-butoxycarbonyl)-8-azabicyclo[3.2.1]octan-3-yl)amino)-7-chloro-1,6-naphthyridine-3-carboxylate The product of the previous step (10.1 g, 19.7 mmol), PdCl$_2$(dppf) (2.87 g, 3.94 mmol) and TEA (5.97 g, 59.2 mmol) was dissolved in methanol (200 mL) and the reaction mixture was stirred at 60° C. under CO atmosphere for 4 h, filtered, and evaporated. The residue was purified by column chromatography (eluted with EtOAc:petroleum ether 0-25%) to give the title intermediate as a yellow solid (7.5 g, 85.6% yield).

(c) Methyl 5-(((1R,3s,5S)-8-(tert-butoxycarbonyl)-8-azabicyclo[3.2.1]octan-3-yl)amino)-7-((5-methyl-1H-pyrazol-3-yl)amino)-1,6-naphthyridine-3-carboxylate The product of the previous step (6.6 g, 14.8 mmol), tert-butyl 3-amino-5-methyl-1H-pyrazole-1-carboxylate (3.5 g, 17.7 mmol), cesium carbonate (9.61 g, 29.6 mmol) and Pd Xphos (2.32 g, 2.95 mmol) were dissolved in dioxane (130 mL) and purged with nitrogen. The reaction mixture was stirred at 110° C. for 12 h. The product was combined with the product of a similar reaction, extracted with EtOAc (600 mL) and washed with brine (3×300 mL). The organic layer was evaporated. The residue was crystalized to provide the title intermediate (5 g, 58% yield) and 2 g of crude product which was purified by preparative HPLC (method 2).

(d) Methyl 5-(((1R,3s,5S)-8-azabicyclo[3.2.1]octan-3-yl)amino)-7-((5-methyl-1H-pyrazol-3-yl)amino)-1,6-naphthyridine-3-carboxylate The product of the previous step (5.5 g, 10.85 mmol) was dissolved in HCl-methanol (50 mL) and the reaction mixture was stirred at RT for 4 h and evaporated under reduced pressure to give the 2HCl salt of the title compound as an orange solid (5.2 g, 100% yield). (m/z): [M+H]$^+$ calcd for C$_{21}$H$_{25}$N$_7$O$_2$ 408.21. found 408.1.

Preparation 13: 5,7-Dichloro-4-methoxy-1,6-naphthyridine

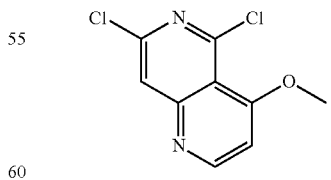

A mixture of 5,7-dichloro-1,6-naphthyridin-4-ol (7 g, 32.6 mmol), methyliodide (41.22 g, 290.4 mmol) and silver carbonate (17.9 g, 65.2 mmol) in toluene (140 mL) was stirred at 100° C. for 2 h. The reaction mixture was filtered and concentrated in vacuo and purified by column chromatography to obtain the title compound as a yellow solid (2.1 g, 28.1% yield). (m/z): [M+H]+ calcd for $C_9H_6Cl_2N_2O$, 228.99, 230.98. found 229.1, 230.0.

Preparation 14:
5,7-dichloro-8-fluoro-1,6-naphthyridine

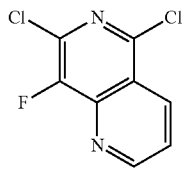 [SMILES: Fc1c(Cl)nc(Cl)c2cccnc12]

(a) 2,6-dichloro-3-fluoropyridin-4-amine

To a mixture of 2,6-dichloropyridin-4-amine (3.0 g, 18.4 mmol) in DMF (30 mL) and ACN (30 mL) was added SelectFluor (7.8 g, 22.1 mmol). The reaction mixture was stirred at 80° C. for 0.5 h, concentrated, and purified by preparative HPLC (method 2) to give the title intermediate as a white solid (1.5 g, 45% yield). (m/z): [M+H]+ calcd for $C_5H_3Cl_2FN_2$ 180.97. found 180.9.

(b) N-(2,6-dichloro-3-fluoropyridin-4-yl)pivalamide

To a mixture of the product of the previous step (1.5 g, 8.29 mmol) in THF (50 mL) was added sodium hydride (662 mg, 16.57 mmol) and pivaloyl chloride (1.12 mL, 9.12 mmol) at 0° C. The reaction mixture was stirred at 25° C. for 2 h, diluted with water, extracted with EtOAc (3×100 mL), dried and concentrated to give the title intermediate as a white solid (2.0 g, 90% yield).

(c) 5,7-dichloro-8-fluoro-1,6-naphthyridine

To a solution of the product of the previous step (2.0 g, 7.55) in THF (25 mL) at −70° C. was added a solution of n-butyl lithium (2.5 M, 7.5 mL, 18.9 mmol) and the reaction mixture was stirred for 60 min at −10° C. A solution of (E)-3-(dimethylamino)acrylaldehyde (1.12 g, 11.3 mmol) in THF (5 mL) was added over 15 min at −70° C., the reaction mixture was stirred at −65° C. for 20 min, HCl (5 M, 12 mL) was added and the reaction mixture was stirred at −65° C. for 12 h. The reaction mixture was adjusted to pH 9 with aqueous $Na_2CO_3$, extracted with EtOAc (3×200 mL), dried, and concentrated to give the residue as a brown oil, which was purified by column chromatography (eluted with 0-30% EtOAc in petroleum ether) to give the title compound as a slightly yellow solid (1.0 g, 99% yield). (m/z): [M+H]+ calcd for $C_8H_3Cl_2FN_2$ 216.97, 218.96. found 217.0, 219.0.

Preparation 15:
5,7-dichloro-8-fluoro-3-methyl-1,6-naphthyridine

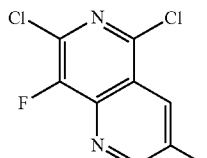

Following the general procedure of Preparation 14 (c) substituting (E)-3-(dimethylamino)-2-methylacrylaldehyde for (E)-3-(dimethylamino)acrylaldehyde, the title intermediate was obtained. (m/z): [M+H]+ calcd for $C_9H_5Cl_2FN_2$ 230.98, 232.98. found 231.0, 233.0.

Preparation 16: tert-Butyl (1R,3s,5S)-3-((7-((5-methyl-1H-pyrazol-3-yl)amino)-3-(methylsulfonyl)-1,6-naphthyridin-5-yl)amino)-8-azabicyclo[3.2.1]octane-8-carboxylate

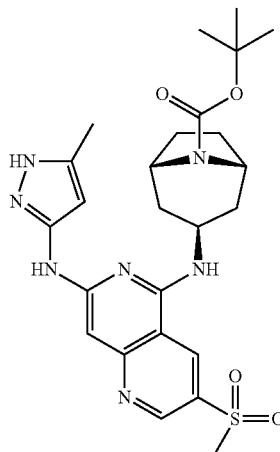

(a) tert-Butyl (1R,3s,5S)-3-((7-chloro-3-(methyl-thio)-1,6-naphthyridin-5-yl)amino)-8-azabicyclo[3.2.1]octane-8-carboxylate A mixture of tert-butyl(1R,3s,5S)-3-((7-chloro-3-iodo-1,6-naphthyridin-5-yl)amino)-8-azabicyclo[3.2.1]octane-8-carboxylate (6.5 g, 12.6 mmol), sodium thiomethoxide (3.0 g, 42.8 mmol), $Pd_2(dba)_3$ (1.1 g, 1.26 mmol), and Xantphos (728 mg, 1.26 mmol) in 3:70 water:toluene (73 mL) was stirred at 90° C. for 12 h and concentrated under vacuum. The residue was purified by column chromatography (1:3 EtOAc:petroleum ether) to afford the title intermediate as a yellow solid (5 g, 90% yield).

(b) tert-Butyl (1R,3s,5S)-3-((7-chloro-3-(methyl-sulfonyl)-1,6-naphthyridin-5-yl)amino)-8-azabicyclo[3.2.1]octane-8-carboxylate To a solution of the product of the previous step (4.5 g, 10 mmol) in DCM (1000 mL) was added meta-chloroperoxybenzoic acid (5.2 g, 30 mmol) at 0° C. and the reaction mixture was stirred at 0° C. for 3 h, washed with 10% NaOH (3×200 mL), dried over $Na_2SO_4$, and filtered. The filtrate was concentrated under vacuum to afford the title intermediate as a yellow solid (4.2 g, 90% yield).

(c) tert-Butyl (1R,3s,5S)-3-((7-((5-methyl-1H-pyrazol-3-yl)amino)-3-(methylsulfonyl)-1,6-naphthyridin-5-yl)amino)-8-azabicyclo[3.2.1]octane-8-carboxylate A mixture of the product of the previous step (4.2 g, 9.0 mmol), tert-butyl 3-amino-5-methyl-1H-pyrazole-1-carboxylate (2.7 g, 13.5 mmol), PdXphos (1.4 g, 1.8 mmol), and cesium carbonate (5.9 g, 18.0 mmol) in dioxane (120 mL) was stirred under nitrogen at 110° C. for 12 h, and concentrated under vacuum. The residue was purified by column chromatography (1:50 methanol:DCM) to afford the title product as a yellow solid (4.0 g, 85% yield). (m/z): [M+H]$^+$ calcd for $C_{25}H_{33}N_7O_4S$, 528.23. found 528.1.

Preparation 17: tert-Butyl (1R,3s,5S)-3-((7-((5-methyl-1H-pyrazol-3-yl)amino)-3-(methylsulfonyl)-1,6-naphthyridin-5-yl)amino)-9-azabicyclo[3.3.1]nonane-9-carboxylate

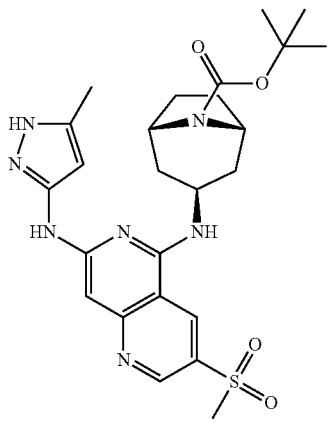 [SMILES: Cc1cc(Nc2cc3ncc(S(C)(=O)=O)cc3c(N[C@@H]3C[C@H]4CC[C@@H](C3)N4C(=O)OC(C)(C)C)n2)n[nH]1]

Following the general procedure of Preparation 16 substituting tert-butyl (1R,3s,5S)-3-((7-chloro-3-iodo-1,6-naphthyridin-5-yl)amino)-9-azabicyclo[3.3.1]nonane-9-carboxylate for tert-butyl (1R,3s,5S)-3-((7-chloro-3-iodo-1,6-naphthyridin-5-yl)amino)-8-azabicyclo[3.2.1]octane-8-carboxylate in step (a), the title intermediate was prepared as a yellow solid. (m/z): [M+H]$^+$ calcd for $C_{26}H_{35}N_7O_4S$, 542.25. found 542.1.

Preparation 18: 5,7-dichloro-2-((methylsulfonyl)methyl)-1,6-naphthyridine

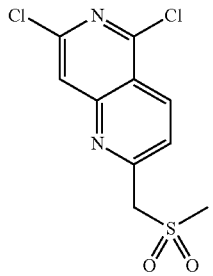 [SMILES: CS(=O)(=O)Cc1ccc2c(Cl)nc(Cl)cc2n1]

To a 20 mL vial was added 2-(bromomethyl)-5,7-dichloro-1,6-naphthyridine (307 mg, 1.052 mmol), sodium methanesulfinate 85% (107 mg, 1.052 mmol), and DMF (5.26 mL). The vial was capped and the reaction mixture was heated to 45° C. and stirred for 1.5 h, cooled to RT, and concentrated by rotary evaporation. The solution was diluted with water; a white precipitate formed, which was removed by filtration, and washed with water and hexanes to afford the title intermediate as a tan solid (259 mg, 85% yield). (m/z): [M+H]$^+$ calcd for $C_{10}H_8Cl_2N_2O_2S$, 290.97. found 290.9.

Example 1: 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile

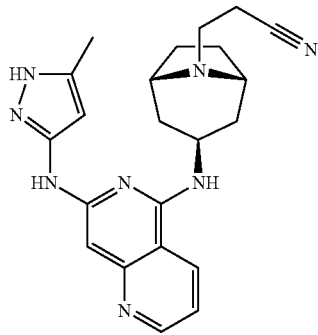 [SMILES: Cc1cc(Nc2cc3ncccc3c(N[C@@H]3C[C@H]4CC[C@@H](C3)N4CCC#N)n2)n[nH]1]

To a 20 mL vial was added N$^5$-((1R,3s,5S)-8-azabicyclo[3.2.1]octan-3-yl)-N$^7$-(5-methyl-1H-pyrazol-3-yl)-1,6-naphthyridine-5,7-diamine, 2TFA (462.4 mg, 0.80 mmol), methanol (4 mL), and DIPEA (0.70 mL, 4.00 mmol). The reaction mixture was stirred at RT for 5 min, and then acrylonitrile (0.058 mL, 0.88 mmol, 100 mL) was slowly added.

The vial was capped and the reaction mixture was stirred at RT for 20 h, concentrated, dissolved in a 15% solution of acetic acid in water, and purified by preparative HPLC (method 1). Fractions were combined, lyophilized, dissolved in 15% acetic acid in water, and purified by reverse-phase HPLC. Fractions were combined and lyophilized to provide the title compound as a bright red solid (505 mg, 52% yield; 98% purity).

(m/z): [M+H]$^+$ calcd for $C_{22}H_{26}N_8$ 403.23. found 403.7.

Example 2: N$^5$-((1R,3s,5S)-8-(2-fluoroethyl)-8-azabicyclo[3.2.1]octan-3-yl)-N$^7$-(5-methyl-1H-pyrazol-3-yl)-1,6-naphthyridine-5,7-diamine

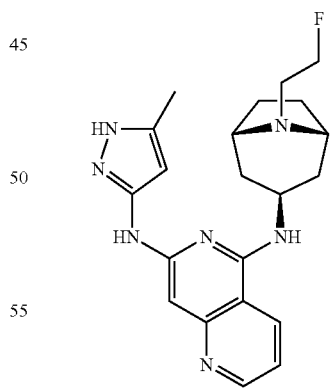

To a 250 mL flask was added N$^5$-((1R,3s,5S)-8-azabicyclo[3.2.1]octan-3-yl)-N$^7$-(5-methyl-1H-pyrazol-3-yl)-1,6-naphthyridine-5,7-diamine, 2 HCl (5.027 g, 11.90 mmol), potassium carbonate (9.87 g, 71.4 mmol), and DMF (59.5 mL). The reaction mixture was stirred at RT for 10 min and then 1-bromo-2-fluoroethane (1.064 mL, 14.28 mmol) was added in one portion. The flask was fitted with an air condenser and the reaction mixture was heated to 40° C. and stirred overnight. Another portion of 1-bromo-2-fluoroethane was added and the reaction mixture was heated to 60° C. and stirred for 24 h. Another portion of 1-bromo-2-fluoroethane was added, and the reaction mixture was stirred at RT for another 24 h. The suspension was divided into four vials and concentrated by rotary evaporation to afford the crude product as a red solid. The material in each vial was dissolved in ~1:1 water:acetic acid, filtered, and purified by preparative HPLC (method 1) to afford the desired product (2.31 g total, 48% yield, 97% purity). (m/z): [M+H]$^+$ calcd for $C_{21}H_{26}FN_7$ 396.22. found 396.2.

Example 3: $N^7$-(5-methyl-1H-pyrazol-3-yl)-$N^5$-((1R,3s,5S)-8-(pyridin-3-ylsulfonyl)-8-azabicyclo[3.2.1]octan-3-yl)-1,6-naphthyridine-5,7-diamine

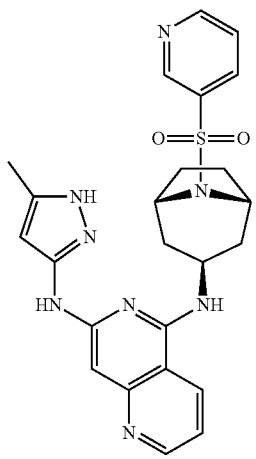 [SMILES: Cc1cc(Nc2cc3ncccc3c(N[C@@H]3C[C@H]4CC[C@@H](C3)N4S(=O)(=O)c3cccnc3)n2)n[nH]1]

A mixture of DIPEA (0.815 mL, 4.66 mmol) and $N^5$-((1R,3s,5S)-8-azabicyclo[3.2.1]octan-3-yl)-$N^7$-(5-methyl-1H-pyrazol-3-yl)-1,6-naphthyridine-5,7-diamine, 1TFA (300 mg, 0.78 mmol) in DMF (6 mL) was cooled to 0° C. and then pyridine-3-sulfonyl chloride (0.093 mL, 0.39 mmol) was added and the solution was stirred for 20 min. The solvent was removed under vacuum and the crude residue was dissolved in 1:1 acetic acid:water (1 mL) and purified by reverse phase HPLC to afford the 1TFA salt of the title compound as an orange solid (156.5 mg, 33% yield)

(m/z): [M+H]$^+$ calcd for $C_{24}H_{26}N_8O_2S$, 491.19. found 491.

Example 4: 2-(Dimethylamino)-1-((1R,3s,5S)-3-((7-((5-methyl-1H-pyrazol-3-yl)amino)-1,6-naphthyridin-5-yl)amino)-9-azabicyclo[3.3.1]nonan-9-yl)ethan-1-one

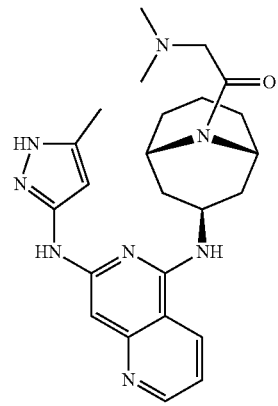 [SMILES: Cc1cc(Nc2cc3ncccc3c(N[C@@H]3C[C@H]4CCC[C@@H](C3)N4C(=O)CN(C)C)n2)n[nH]1]

To a 20 mL vial was added dimethylglycine hydrochloride (31 mg, 0.22 mmol), HATU (85 mg, 0.22 mmol), and DMF (1 mL). The clear solution was stirred at RT for 15 min, followed by the addition of $N^5$-((1R,3s,5S)-9-azabicyclo[3.3.1]nonan-3-yl)-$N^7$-(5-methyl-1H-pyrazol-3-yl)-1,6-naphthyridine-5,7-diamine 2TFA (120 mg, 0.20 mmol). The reaction mixture was stirred at RT for 30 min and then DIPEA (0.18 mL, 1.01 mmol) was added. The resulting reaction mixture was stirred at RT for 2 days, and concentrated by rotary evaporation to provide a thick, dark brown oil. The crude oil was dissolved in 2:1 water:acetic acid, filtered, and purified by reverse-phase HPLC. Fractions were combined and lyophilized to afford the 2TFA salt of the title compound as a red solid (23 mg, 25% yield. 100% purity). (m/z): [M+H]$^+$ calcd for $C_{24}H_{32}N_8O$, 449.27. found 449.2.

Example 5: 2,2-difluoro-1-((1R,3s,5S)-3-((7-((5-methyl-1H-pyrazol-3-yl)amino)-1,6-naphthyridin-5-yl)amino)-8-azabicyclo[3.2.1]octan-8-yl)ethan-1-one

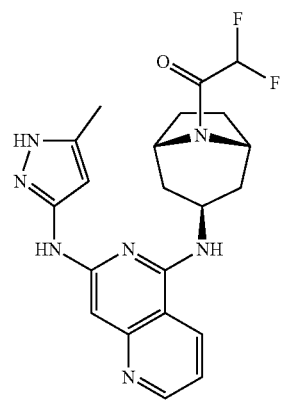 [SMILES: Cc1cc(Nc2cc3ncccc3c(N[C@@H]3C[C@H]4CC[C@@H](C3)N4C(=O)C(F)F)n2)n[nH]1]

To a 20 mL vial was added difluoroacetic acid (0.026 mL, 0.42 mmol), HATU (159 mg, 0.42 mmol), and DMF (1.91 mL). The clear solution was stirred at RT for 10 min, then $N^5$-((1R,3s,5S)-8-azabicyclo[3.2.1]octan-3-yl)-$N^7$-(5-methyl-1H-pyrazol-3-yl)-1,6-naphthyridine-5,7-diamine, 2

TFA (220 mg, 0.38 mmol) was added in one portion. The resulting red solution was stirred at RT for 20 min, and DIPEA (0.33 mL, 1.91 mmol) was added. The vial was capped and the reaction mixture was stirred at RT overnight, and concentrated by rotary evaporation to afford a thick, red oil. The crude oil was dissolved in ~3:1 water:acetic acid, filtered, and purified by preparative HPLC (method 1) to afford the desired product as a red solid. Fractions were combined, dissolved in 2:1 water:acetic acid and purified by preparative HPLC (method 1) to afford the 1TFA salt of the title product as a red solid (77 mg, 36% yield; 96% purity).

(m/z): [M+H]$^+$ calcd for $C_{21}H_{23}F_2N_7O$, 428.19. found 428.1.

Example 6: $N^5$-((1R,3s,5S)-8-((2-methoxyethyl)sulfonyl)-8-azabicyclo[3.2.1]octan-3-yl)-$N^7$-(5-methyl-1H-pyrazol-3-yl)-1,6-naphthyridine-5,7-diamine

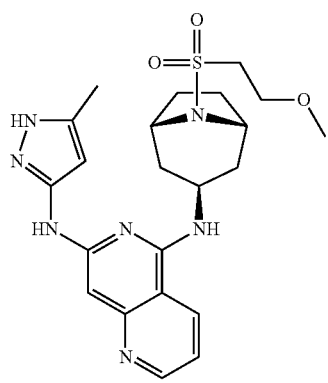 [SMILES: COCCS(=O)(=O)N1[C@@H]2CC[C@H]1C[C@H](Nc1nc(Nc3cc(C)[nH]n3)cc3ncccc13)C2]

To a 4 mL vial was added $N^5$-((1R,3s,5S)-8-azabicyclo[3.2.1]octan-3-yl)-$N^7$-(5-methyl-1H-pyrazol-3-yl)-1,6-naphthyridine-5,7-diamine, 2TFA (30 mg, 0.052 mmol), DIPEA (0.045 mL, 0.26 mmol), and DMF (1.15 mL). The solution was cooled to 0° C. and a solution of 2-methoxy-1-ethanesulfonyl chloride (12 mg, 0.078 mmol) in DMF (1.15 mL) was added slowly to the cold reaction mixture. The vial containing the sulfonyl chloride was rinsed with DMF (1.15 mL) and the rinse was added to the vial containing the reaction solution, which was capped and stirred at 0° C. for 30 min, warmed to RT, and stirred for 6 h. The solution was concentrated by rotary evaporation to afford a red oil which was dissolved in 3:1 water:acetic acid, filtered, and purified by reverse-phase HPLC to afford the 1TFA salt of the title compound (12.3 mg, 100% purity). (m/z): [M+H]$^+$ calcd for $C_{22}H_{29}N_7O_3S$, 472.21. found 472.2.

Example 7: $N^5$-((1R,3s,5S)-8-(ethylsulfonyl)-8-azabicyclo[3.2.1]octan-3-yl)-$N^7$-(5-methyl-1H-pyrazol-3-yl)-1,6-naphthyridine-5,7-diamine

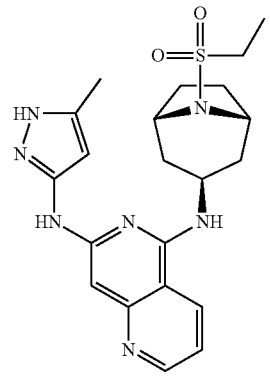 [SMILES: CCS(=O)(=O)N1[C@@H]2CC[C@H]1C[C@H](Nc1nc(Nc3cc(C)[nH]n3)cc3ncccc13)C2]

Following the procedure of Example 6, using ethylsulfonyl chloride (0.007 mL, 0.078 mmol) in place of 2-methoxy-1-ethanesulfonyl chloride, the 1TFA salt of the title compound (10.1 mg, 100% purity) was prepared. (m/z): [M+H]$^+$ calcd for $C_{21}H_{27}N_7O_2S$, 442.20. found 442.2.

Example 8: $N^7$-(5-methyl-1H-pyrazol-3-yl)-$N^5$-((1R,3s,5S)-9-(pyridin-3-ylsulfonyl)-9-azabicyclo[3.3.1]nonan-3-yl)-1,6-naphthyridine-5,7-diamine

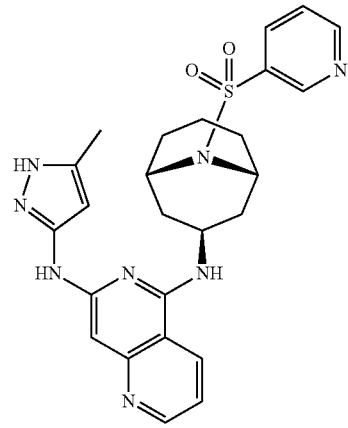 [SMILES: Cc1cc(Nc2cc3ncccc3c(N[C@@H]3C[C@H]4CCC[C@@H](C3)N4S(=O)(=O)c3cccnc3)n2)n[nH]1]

A mixture of $N^5$-((1R,3s,5S)-9-azabicyclo[3.3.1]nonan-3-yl)-$N^7$-(5-methyl-1H-pyrazol-3-yl)-1,6-naphthyridine-5,7-diamine 2 HCl (43.6 mg, 0.10 mmol) and DIPEA (0.105 mL, 0.60 mmol) in DMF (1 mL) was cooled to 0° C. and pyridine-3-sulfonyl chloride (17.8 mg, 0.10 mmol) was added. The solution was stirred overnight, allowed to gradually warm to RT, concentrated to dryness in vacuo, dissolved in 2:1 water:acetic acid (1.5 mL), syringe filtered (0.2 micron), and purified by reverse phase HPLC to provide the 1TFA salt of the title compound (24 mg, 94.4% purity). (m/z): [M+H]$^+$ calcd for $C_{25}H_{28}N_8O_2S$, 505.21. found 505.2.

Example 9: N⁷-(5-methyl-1H-pyrazol-3-yl)-N⁵-((1R,3s,5S)-9-(phenylsulfonyl)-9-azabicyclo[3.3.1]nonan-3-yl)-1,6-naphthyridine-5,7-diamine

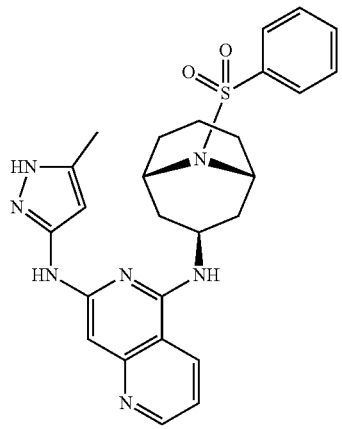 [SMILES: Cc1cc(Nc2cc3ncccc3c(N[C@@H]3C[C@H]4CCC[C@@H](C3)N4S(=O)(=O)c3ccccc3)n2)n[nH]1]

Following the exact procedure of Example 8, substituting benzenesulfonyl chloride (17.7 mg, 0.10 mmol) for pyridine-3-sulfonyl chloride (17.8 mg, 0.10 mmol), the 1TFA salt of the title compound was obtained (7 mg, 94.4% purity). (m/z): [M+H]⁺ calcd for $C_{25}H_{28}N_8O_2S$, 504.21. found 504.1.

Example 10: N⁵-((1R,3s,5S)-9-(ethylsulfonyl)-9-azabicyclo[3.3.1]nonan-3-yl)-N⁷-(5-methyl-1H-pyrazol-3-yl)-1,6-naphthyridine-5,7-diamine

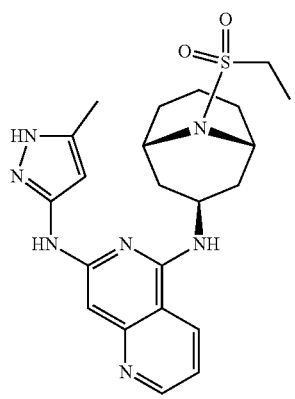 [SMILES: CCS(=O)(=O)N1[C@@H]2CCC[C@H]1C[C@H](Nc1nc(Nc3cc(C)[nH]n3)cc3ncccc13)C2]

To a 20 mL vial was added N⁵-((1R,3s,5S)-9-azabicyclo[3.3.1]nonan-3-yl)-N⁷-(5-methyl-1H-pyrazol-3-yl)-1,6-naphthyridine-5,7-diamine 2TFA (100 mg, 0.17 mmol), DIPEA (0.148 mL, 0.85 mmol), and DMF (0.85 mL). The solution was cooled to 0° C. and a solution of ethylsulfonyl chloride (26 mg, 0.20 mmol) in DMF (0.85 mL) was added to the cold reaction mixture dropwise. The vial containing the sulfonyl chloride was rinsed with DMF (0.85 mL) and the rinse was added to the vial containing the reaction solution, which was stirred at 0° C. for 15 min, warmed to RT, and stirred for 20 h. The solution was concentrated by rotary evaporation to afford a dark red oil which was dissolved in a 3:1 water:acetic acid mixture (3 mL), filtered, and purified by preparative HPLC (method 1) to provide the 1TFA salt of the title compound (13 mg, 93% purity). (m/z): [M+H]⁺ calcd for $C_{22}H_{29}N_7O_2S$, 456.21. found 456.1.

Example 11: 1-(((1R,3s,5S)-3-((7-((5-methyl-1H-pyrazol-3-yl)amino)-1,6-naphthyridin-5-yl)amino)-9-azabicyclo[3.3.1]nonan-9-yl)sulfonyl)azetidine-3-carbonitrile

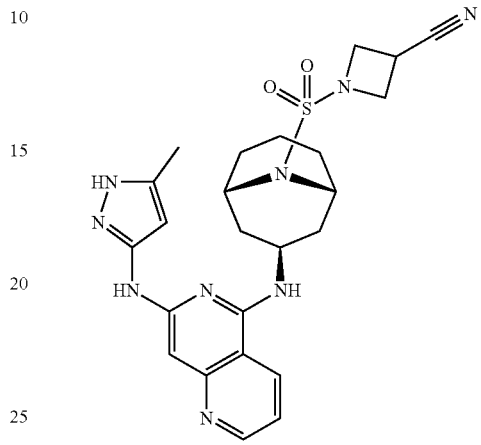

A mixture of N⁵-((1R,3s,5S)-9-azabicyclo[3.3.1]nonan-3-yl)-N⁷-(5-methyl-1H-pyrazol-3-yl)-1,6-naphthyridine-5,7-diamine 2HCl (58 mg, 0.067 mmol) and DIPEA (0.584 mL, 0.335 mmol) in DMF (1 mL) was cooled to 0° C. and 3-cyano-1-azetidinesulfonyl chloride (24 mg, 0.067 mmol) was added. The solution was stirred overnight, allowed to gradually warm to RT, concentrated to dryness in vacuo, dissolved in 1:1 water:acetic acid (1.5 mL), syringe filtered (0.2 micron), and purified by reverse phase HPLC to afford the 1TFA salt of the title compound (7.8 mg, 100% purity). (m/z): [M+H]⁺ calcd for $C_{24}H_{29}N_9O_2S$, 508.22. found 508.6.

Example 12: Isobutyl (1R,3s,5S)-3-((2-(hydroxymethyl)-7-((5-methyl-1H-pyrazol-3-yl)amino)-1,6-naphthyridin-5-yl)amino)-8-azabicyclo[3.2.1]octane-8-carboxylate

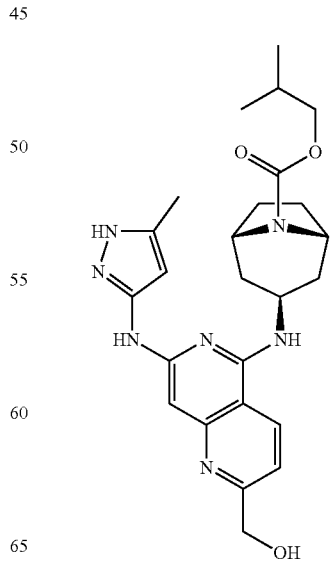

(a) (5-(((1R,3s,5S)-8-azabicyclo[3.2.1]octan-3-yl)amino)-7-((5-methyl-1H-pyrazol-3-yl)amino)-1,6-naphthyridin-2-yl)methanol To a 40 mL vial was added tert-butyl (1R,3s,5S)-3-((2-(hydroxymethyl)-7-((5-methyl-1H-pyrazol-3-yl)amino)-1,6-naphthyridin-5-yl)amino)-8-azabicyclo[3.2.1]octane-8-carboxylate (146.6 mg, 0.31 mmol), 4M HCl in dioxane (1.53 mL, 6.11 mmol), and dioxane (1.53 mL). The vial was capped and the reaction mixture was stirred at RT for 6 h, frozen at −78° C. and lyophilized to afford the 2HCl salt of the title intermediate as a tan solid that was used in next reaction without purification. (m/z): [M+H]$^+$ calcd for $C_{20}H_{25}N_7O$, 380.21. found 380.1.

(b) Isobutyl (1R,3s,5S)-3-((2-(hydroxymethyl)-7-((5-methyl-1H-pyrazol-3-yl)amino)-1,6-naphthyridin-5-yl)amino)-8-azabicyclo[3.2.1]octane-8-carboxylate To the product of the previous step (138 mg, 0.31 mmol)) was added DMF (1.53 mL), and DIPEA (0.32 mL, 1.83 mmol). The solution was cooled to 0° C. and then isobutyl chloroformate (0.04 mL, 0.31 mmol) was added dropwise. The vial was capped and the reaction mixture was stirred at 0° C. for 30 min, then warmed to RT, stirred for 1 h, and concentrated by rotary evaporation to afford a red solid. The solid was dissolved in 2:1 acetic acid:water, filtered, and purified by preparative HPLC (method 1) to afford the 1TFA salt of the title compound as an orange/red solid (104.2 mg, 57% yield; 99% purity). (m/z): [M+H]$^+$ calcd for $C_{25}H_{33}N_7O_3$ 480.26. found 480.2.

Example 13: 1-(((1R,3s,5S)-3-((7-((5-methyl-1H-pyrazol-3-yl)amino)-1,6-naphthyridin-5-yl)amino)-8-azabicyclo[3.2.1]octan-8-yl)sulfonyl)azetidine-3-carbonitrile

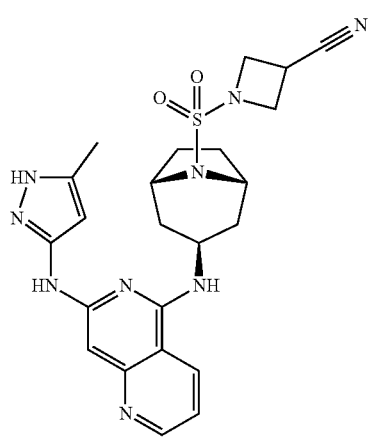 [SMILES: Cc1cc(Nc2cc3ncccc3c(N[C@@H]3C[C@H]4CC[C@@H](C3)N4S(=O)(=O)N3CC(C#N)C3)n2)n[nH]1]

A mixture of N$^5$-((1R,3s,5S)-8-azabicyclo[3.2.1]octan-3-yl)-N$^7$-(5-methyl-1H-pyrazol-3-yl)-1,6-naphthyridine-5,7-diamine 2TFA (77 mg, 0.067 mmol) and DIPEA (0.584 mL, 0.335 mmol) in DMF (1 mL) was cooled to 0° C. and 3-cyano-1-azetidinesulfonyl chloride (24 mg, 0.067 mmol) was added. The solution was stirred overnight, allowed to gradually warm to RT, concentrated to dryness in vacuo, dissolved in 1:1 water:acetic acid (1.5 mL), syringe filtered (0.2 micron), and purified by reverse phase HPLC to afford the 1TFA salt of the title compound (5.3 mg, 100% purity). (m/z): [M+H]$^+$ calcd for $C_{23}H_{27}N_9O_2S$, 494.20. found 494.6.

Example 14: N$^5$-((1R,3s,5S)-9-((5-fluoropyridin-3-yl)sulfonyl)-9-azabicyclo[3.3.1]nonan-3-yl)-N$^7$-(5-methyl-1H-pyrazol-3-yl)-1,6-naphthyridine-5,7-diamine

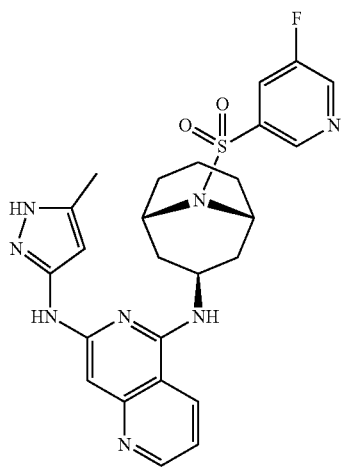 [SMILES: Cc1cc(Nc2cc3ncccc3c(N[C@@H]3C[C@H]4CCC[C@@H](C3)N4S(=O)(=O)c3cncc(F)c3)n2)n[nH]1]

A mixture of N$^5$-((1R,3s,5S)-9-azabicyclo[3.3.1]nonan-3-yl)-N$^7$-(5-methyl-1H-pyrazol-3-yl)-1,6-naphthyridine-5,7-diamine 2 HCl (30.2 mg, 0.069 mmol) and DIPEA (0.072 mL, 0.41 mmol) in DMF (1 mL) was cooled to 0° C. and 5-fluoropyridine-3-sulfonyl chloride (13.5 mg, 0.069 mmol) was added. The solution was stirred overnight, allowed to gradually warm to RT, concentrated to dryness in vacuo, dissolved in 2:1 water:acetic acid (1.5 mL), syringe filtered (0.2 micron), and purified by reverse phase HPLC to provide the 1TFA salt of the title compound (20 mg, 100% purity).

(m/z): [M+H]$^+$ calcd for $C_{25}H_{27}FN_8O_2S$, 523.20. found 523.2.

Example 15: N$^7$-(5-methyl-1H-pyrazol-3-yl)-2-(morpholinomethyl)-N$^5$-((1R,3s,5S)-8-(2,2,2-trifluoroethyl)-8-azabicyclo[3.2.1]octan-3-yl)-1,6-naphthyridine-5,7-diamine

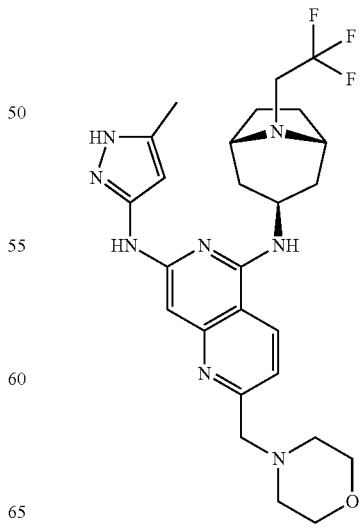

To a solution of $N^5$-(((1R,3s,5S)-8-azabicyclo[3.2.1]octan-3-yl)-$N^7$-(5-methyl-1H-pyrazol-3-yl)-2-(morpholinomethyl)-1,6-naphthyridine-5,7-diamine (81 mg, 0.181 mmol) and DIPEA (0.126 mL, 0.722 mmol) in DMF (3.62 mL) was added 2,2,2-trifluoroethyltrifluoromethane-sulfonate (0.030 mL, 0.217 mmol) at 20° C. The mixture was stirred at 20° C. for 3 days, concentrated by rotary evaporation, and purified by preparative HPLC (method 1) to give the title compound as a red solid (22.1 mg, 19% yield). (m/z): [M+H]$^+$ calcd for $C_{26}H_{33}F_3N_8O$, 531.27. found 531.2.

Example 16: Methyl 7-((5-methyl-1H-pyrazol-3-yl)amino)-5-(((1R,3s,5S)-8-(2-oxotetrahydro-2H-pyran-3-yl)-8-azabicyclo[3.2.1]octan-3-yl)amino)-1,6-naphthyridine-3-carboxylate

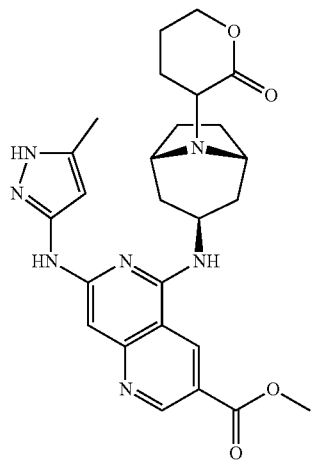 [SMILES: COC(=O)c1cnc2cc(Nc3cc(C)[nH]n3)nc(N[C@@H]3C[C@H]4CC[C@@H](C3)N4C3CCCOC3=O)c2c1]

To a solution of methyl 5-(((1R,3s,5S)-8-azabicyclo[3.2.1]octan-3-yl)amino)-7-((5-methyl-1H-pyrazol-3-yl)amino)-1,6-naphthyridine-3-carboxylate 2HCl in methanol (4 mL) was added tetraalkylammonium carbonate, polymer-bound (0.231 mmol) and the suspension was stirred at RT for 30 min, filtered, and concentrated to afford the free-based carboxylate compound.

To a 20 mL vial was added 3-hydroxytetrahydro-2H-pyran-2-one (0.042 mL, 0.46 mmol) and DCM (0.46 mL). The solution was cooled to −40° C., and DIPEA (0.161 mL, 0.92 mmol) was added, followed by trifluoromethanesulfonic anhydride (0.080 mL, 0.47 mmol). The vial was capped and stirred at −40° C. for 1 h. After 1 h, a solution of the free based carboxylate compound (0.094 g, 0.23 mmol) dissolved in DMF (200 μL) was added to the cold reaction mixture. The vial was capped and the solution was stirred at −40° C. and slowly warmed to RT over 2 h, stirred at RT over the weekend, and concentrated by rotary evaporation to afford a thick, brown oil. The crude oil was dissolved in 1:1 water:acetic acid, filtered, and purified by reverse-phase HPLC to provide the title compound as a bright red solid (45 mg, 27% yield; 100% purity).

(m/z): [M+H]$^+$ calcd for $C_{26}H_{31}N_7O_4$ 506.24. found 506.1.

Example 17: N-methyl-2-((1R,3s,5S)-3-((7-((5-methyl-1H-pyrazol-3-yl)amino)-1,6-naphthyridin-5-yl)amino)-9-azabicyclo[3.3.1]nonan-9-yl)acetamide

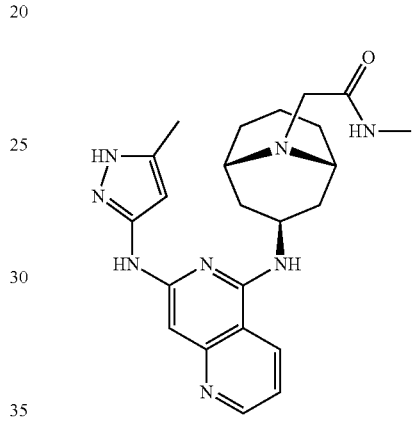

A solution of $N^5$-((1R,3s,5S)-9-azabicyclo[3.3.1]nonan-3-yl)-$N^7$-(5-methyl-1H-pyrazol-3-yl)-1,6-naphthyridine-5,7-diamine TFA (100 mg, 0.209 mmol), 2-bromo-n-methylacetamide (33.4 mg, 0.220 mmol), and DIPEA (146 uL) in DMF (2 mL) was stirred overnight, concentrated, and purified by reverse-phase HPLC to provide the title compound (50 mg, 55% yield). (m/z): [M+H]$^+$ calcd for $C_{23}H_{30}N_8O$, 435.25. found 435.6.

Using similar synthetic methods, the compounds of Tables 1-8 were prepared.

TABLE 1

| Ex No. | n | R$^1$ | Formula | Calc [M + H]$^+$ | Found [M + H]$^+$ |
|---|---|---|---|---|---|
| 1-1 | 1 | —CH$_2$C(O)OCH$_3$ | $C_{22}H_{27}N_7O_2$ | 422.22 | 422.2 |
| 1-2 | 1 | —(CH$_2$)$_2$C(O)OCH$_3$ | $C_{23}H_{29}N_7O_2$ | 436.24 | 436.2 |

TABLE 1-continued

| Ex No. | n | R¹ | Formula | Calc [M + H]⁺ | Found [M + H]⁺ |
|---|---|---|---|---|---|
| 1-3 | 1 | —(CH₂)₃C(O)OCH₃ | C₂₄H₃₁N₇O₂ | 450.25 | 450.2 |
| 1-4 | 1 | —CH₂C(O)O—iPr | C₂₄H₃₁N₇O₂ | 450.25 | 450.2 |
| 1-5 | 1 | —CH₂C(O)O—tBu | C₂₅H₃₃N₇O₂ | 464.27 | 464.2 |
| 1-6 | 1 | —CH₂C(O)NH₂ | C₂₁H₂₆N₈O | 407.22 | 407.2 |
| 1-7 | 1 | —CH₂C(O)NHCH₃ | C₂₂H₂₈N₈O | 421.24 | 421.1 |
| 1-8 | 1 | —CH₂C(O)N(CH₃)₂ | C₂₃H₃₀N₈O | 435.25 | 435.2 |
| 1-9 | 1 | —(CH₂)₂CH₂F | C₂₂H₂₈FN₇ | 410.24 | 410.2 |
| 1-10 | 1 | —(CH₂)₂CF₃ | C₂₂H₂₆F₃N₇ | 446.22 | 446.2 |
| 1-11 | 1 | (R)-3-oxotetrahydrofuran-3-yl amide | C₂₅H₃₀N₈O₃ | 491.24 | 491.1 |
| 1-12 | 1 | (S)-3-oxotetrahydrofuran-3-yl amide | C₂₅H₃₀N₈O₃ | 491.24 | 492.2 |
| 1-13 | 1 | —CH₂—iPr | C₂₃H₃₁N₇ | 406.26 | 406.2 |
| 1-14 | 1 | —CH₂CF₃ | C₂₁H₂₄F₃N₇ | 432.20 | 432.1 |
| 1-15 | 1 | —(CH₂)₃OCH₃ | C₂₃H₃₁N₇O | 422.26 | 422.1 |
| 1-16 | 1 | —CH₂-pyridin-3-yl | C₂₅H₂₈N₈ | 441.24 | 441.2 |
| 1-17 | 1 | —CH₂-pyridin-4-yl | C₂₅H₂₈N₈ | 441.24 | 441.2 |
| 1-18 | 1 | —CH₂-(4-hydroxyphenyl) | C₂₆H₂₉N₇O | 456.24 | 456.3 |
| 1-19 | 1 | —CH₂-(3-hydroxyphenyl) | C₂₆H₂₉N₇O | 456.24 | 456.1 |
| 1-20 | 1 | —CH₂-tetrahydropyran-4-yl | C₂₅H₃₃N₇O | 448.27 | 448.2 |
| 1-21 | 1 | —CH(CH₃)CH₂CN | C₂₃H₂₈N₈ | 417.24 | 417.2 |
| 1-22 | 1 | —CH(C₂H₅)CH₂CN | C₂₄H₃₀N₈ | 431.26 | 431.2 |
| 1-23 | 1 | —CH₂CH(CH₃)CN | C₂₃H₂₈N₈ | 417.24 | 417.2 |
| 1-24 | 1 | —CH₂-(1-cyanocyclopropyl) | C₂₄H₂₈N₈ | 429.24 | 429.2 |
| 1-25 | 1 | —CH₂-(3-cyanooxetan-3-yl) | C₂₄H₂₈N₈O | 445.24 | 445.1 |

TABLE 1-continued

| Ex No. | n | R¹ | Formula | Calc [M + H]⁺ | Found [M + H]⁺ |
|---|---|---|---|---|---|
| 1-26 | 1 | (γ-butyrolactone, 3-subst) | $C_{23}H_{27}N_7O_2$ | 434.22 | 434.2 |
| 1-27 | 1 | (γ-butyrolactone, 3-subst) (a) | $C_{23}H_{27}N_7O_2$ | 434.22 | 434.2 |
| 1-28 | 1 | (δ-valerolactone, 3-subst) | $C_{24}H_{29}N_7O_2$ | 448.24 | 448.2 |
| 1-29 | 1 | (R)-γ-butyrolactone, 5-subst via CH₂ | $C_{24}H_{29}N_7O_2$ | 448.24 | 448.2 |
| 1-30 | 1 | (1,3-dioxolan-2-one, 4-subst via CH₂) | $C_{23}H_{27}N_7O_3$ | 450.22 | 450.2 |
| 1-31 | 2 | —(CH₂)₂CN | $C_{23}H_{28}N_8$ | 417.24 | 417.2 |
| 1-32 | 2 | —CH₂C(O)OCH₃ | $C_{23}H_{29}N_7O_2$ | 436.24 | 436.2 |
| 1-33 | 2 | —(CH₂)₂C(O)OCH₃ | $C_{24}H_{31}N_7O_2$ | 450.25 | 450.2 |
| 1-34 | 2 | —(CH₂)₃C(O)OCH₃ | $C_{25}H_{33}N_7O_2$ | 464.27 | 464.2 |
| 1-35 | 2 | —CH₂C(O)O—iPr | $C_{25}H_{33}N_7O_2$ | 464.27 | 464.2 |
| 1-36 | 2 | —CH₂C(O)O—tBu | $C_{26}H_{35}N_7O_2$ | 478.29 | 478.2 |
| 1-37 | 2 | —CH₂C(O)NH₂ | $C_{22}H_{28}N_8O$ | 421.24 | 421.2 |
| 1-38 | 2 | —CH₂C(O)N(CH₃)₂ | $C_{24}H_{32}N_8O$ | 449.27 | 449.2 |
| 1-39 | 2 | —CH₂CH₂F | $C_{22}H_{28}FN_7$ | 410.24 | 410.2 |
| 1-40 | 2 | —(CH₂)₂CH₂F | $C_{23}H_{30}FN_7$ | 424.25 | 424.2 |
| 1-41 | 2 | (R)-homoserine lactone amide | $C_{26}H_{32}N_8O_3$ | 505.26 | 505.2 |
| 1-42 | 2 | (S)-homoserine lactone amide | $C_{26}H_{32}N_8O_3$ | 505.26 | 505.2 |
| 1-43 | 2 | —CH₂—iPr | $C_{24}H_{33}N_7$ | 420.28 | 420.2 |
| 1-44 | 2 | —(CH₂)₂CF₃ | $C_{23}H_{28}F_3N_7$ | 460.24 | 460.2 |

TABLE 1-continued

| Ex No. | n | R¹ | Formula | Calc [M + H]⁺ | Found [M + H]⁺ |
|---|---|---|---|---|---|
| 1-45 | 2 | —CH₂CF₃ | $C_{22}H_{26}F_3N_7$ | 446.22 | 446.1 |
| 1-46 | 2 | —(CH₂)₃OCH₃ | $C_{24}H_{33}N_7O$ | 436.27 | 436.2 |
| 1-47 | 2 | —CH₂-pyridin-3-yl | $C_{26}H_{30}N_8$ | 455.26 | 455.2 |
| 1-48 | 2 | —CH₂-pyridin-4-yl | $C_{26}H_{30}N_8$ | 455.26 | 455.2 |
| 1-49 | 2 | (3-hydroxybenzyl) | $C_{27}H_{31}N_7O$ | 470.26 | 470.1 |
| 1-50 | 2 | (4-hydroxybenzyl) | $C_{27}H_{31}N_7O$ | 470.26 | 470.3 |
| 1-51 | 2 | (γ-butyrolactone-3-ylmethyl) | $C_{24}H_{29}N_7O_2$ | 448.24 | 448.2 |
| 1-52 | 2 | (γ-butyrolactone-3-ylmethyl) (a) | $C_{24}H_{29}N_7O_2$ | 448.24 | 448.2 |
| 1-53 | 2 | (δ-valerolactone-3-ylmethyl) | $C_{25}H_{31}N_7O_2$ | 462.25 | 462.2 |
| 1-54 | 2 | (5-cyanopyridin-3-yl)methyl | $C_{27}H_{29}N_9$ | 480.25 | 480.2 |
| 1-55 | 2 | (2-cyanopyridin-4-yl)methyl | $C_{27}H_{29}N_9$ | 480.25 | 480.2 |

TABLE 1-continued

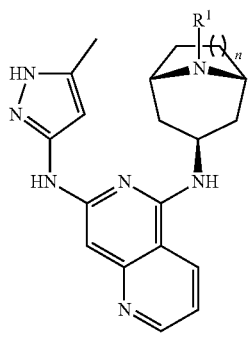

| Ex No. | n | R¹ | Formula | Calc [M + H]⁺ | Found [M + H]⁺ |
|---|---|---|---|---|---|
| 1-56 | 2 | (3-cyano-pyridin-4-yl)methyl | $C_{27}H_{29}N_9$ | 480.25 | 480.2 |
| 1-57 | 2 | (R)-(5-oxotetrahydrofuran-2-yl)methyl | $C_{25}H_{31}N_7O_2$ | 462.25 | 462.2 |
| 1-58 | 2 | (2-oxo-1,3-dioxolan-4-yl)methyl | $C_{24}H_{29}N_7O_3$ | 464.23 | 464.2 |

(a) Stereoisomers separated but not identified

TABLE 2

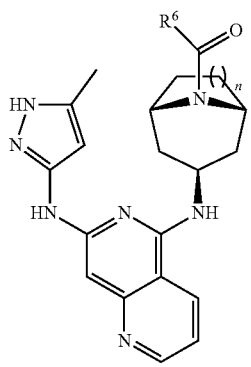

| Ex No. | n | R⁶ | Formula | Calc [M + H]⁺ | Found [M + H]⁺ |
|---|---|---|---|---|---|
| 2-1 | 1 | —C₂H₅ | $C_{22}H_{27}N_7O$ | 406.23 | 406.2 |
| 2-2 | 1 | —CH₂F | $C_{21}H_{24}FN_7O$ | 410.20 | 410.1 |
| 2-3 | 1 | —CH(CH₃)F | $C_{22}H_{26}FN_7O$ | 424.22 | 424.1 |
| 2-4 | 1 | —CH₂OC₂H₅ | $C_{23}H_{29}N_7O_2$ | 436.24 | 436.2 |
| 2-5 | 1 | —CH₂N(CH₃)₂ | $C_{23}H_{30}N_8O$ | 435.25 | 435.2 |
| 2-6 | 1 | —CH((S)CH₃)C₂H₅ | $C_{24}H_{31}N_7O$ | 434.26 | 434.2 |
| 2-7 | 1 | 1-methyl-1-(1-(trifluoroacetyl)cyclopropyl)ethyl | $C_{24}H_{26}F_3N_7O$ | 486.22 | 486.2 |

TABLE 2-continued

| Ex No. | n | R⁶ | Formula | Calc [M + H]⁺ | Found [M + H]⁺ |
|---|---|---|---|---|---|
| 2-8 | 1 | (1-cyano-cyclopropyl with methyl, C(O)) | $C_{24}H_{26}N_8O$ | 443.22 | 443.2 |
| 2-9 | 1 | (cyclopropyl methyl ester with methyl, C(O)OMe) | $C_{25}H_{29}N_7O_3$ | 476.23 | 476.2 |
| 2-10 | 1 | (1-methyl-cyclopentyl) | $C_{26}H_{33}N_7O$ | 460.27 | 460.6 |
| 2-11 | 1 | —CH₂-phenyl | $C_{27}H_{29}N_7O$ | 468.24 | 468.1 |
| 2-12 | 1 | phenyl | $C_{26}H_{27}N_7O$ | 454.23 | 454.2 |
| 2-13 | 1 | pyridin-4-yl | $C_{25}H_{26}N_8O$ | 455.22 | 455.1 |
| 2-14 | 1 | pyridin-3-yl | $C_{25}H_{26}N_8O$ | 455.22 | 455.5 |
| 2-15 | 2 | —C₂H₅ | $C_{23}H_{29}N_7O$ | 420.24 | 420.2 |
| 2-16 | 2 | —CH((S)OH)CH₃ | $C_{23}H_{29}N_7O_2$ | 436.24 | 436.2 |
| 2-17 | 2 | —CH₂OC₂H₅ | $C_{24}H_{31}N_7O_2$ | 450.25 | 450.2 |
| 2-18 | 2 | —CH((S)CH₃)C₂H₅ | $C_{25}H_{33}N_7O$ | 448.27 | 448.2 |
| 2-19 | 2 | (1-trifluoroacetyl-cyclopropyl with methyl) | $C_{25}H_{28}F_3N_7O$ | 500.23 | 500.2 |
| 2-20 | 2 | (1-cyano-cyclopropyl with methyl, C(O)) | $C_{25}H_{28}N_8O$ | 457.24 | 457.2 |
| 2-21 | 2 | (cyclopropyl methyl ester with methyl, C(O)OMe) | $C_{26}H_{31}N_7O_3$ | 490.25 | 490.2 |
| 2-22 | 2 | —C(CH₃)₂CH₂OH | $C_{25}H_{33}N_7O_2$ | 464.27 | 464.2 |
| 2-23 | 2 | (1-methyl-cyclopentyl) | $C_{27}H_{35}N_7O$ | 474.29 | 474.6 |
| 2-24 | 2 | —CH₂-phenyl | $C_{28}H_{31}N_7O$ | 482.26 | 482.1 |
| 2-25 | 2 | phenyl | $C_{27}H_{29}N_7O$ | 468.24 | 468.1 |

TABLE 2-continued
| Ex No. | n | R⁶ | Formula | Calc [M + H]⁺ | Found [M + H]⁺ |
|---|---|---|---|---|---|
| 2-26 | 2 | (5-cyanopyridin-3-yl, attached at 3-position) | $C_{27}H_{27}N_9O$ | 494.23 | 494.2 |
| 2-27 | 2 | —(CH$_2$)$_3$CN | $C_{25}H_{30}N_8O$ | 459.25 | 459.2 |
| 2-28 | 2 | (6-cyanopyridin-3-yl) | $C_{27}H_{27}N_9O$ | 494.23 | 494.2 |
| 2-29 | 2 | —CH(CH$_3$)CH$_2$CN | $C_{25}H_{30}N_8O$ | 459.25 | 459.2 |
| 2-30 | 2 | (2-cyanopyridin-4-yl) | $C_{27}H_{27}N_9O$ | 494.23 | 494.2 |
| 2-31 | 2 | —(CH$_2$)$_2$—iPr | $C_{26}H_{35}N_7O$ | 462.29 | 462.2 |
TABLE 3
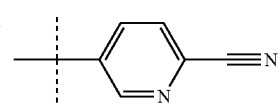
| Ex No. | n | R⁸ | Formula | Calc [M + H]⁺ | Found [M + H]⁺ |
|---|---|---|---|---|---|
| 3-1 | 1 | —C$_2$H$_5$ | $C_{22}H_{27}N_7O_2$ | 422.22 | 422.2 |
| 3-2 | 1 | —iPr | $C_{23}H_{29}N_7O_2$ | 436.24 | 436.2 |
| 3-3 | 1 | —CH$_2$—iPr | $C_{24}H_{31}N_7O_2$ | 450.25 | 450.2 |
| 3-4 | 1 | —CH$_2$CH=CH$_2$ | $C_{23}H_{27}N_7O_2$ | 434.22 | 434.2 |
| 3-5 | 1 | —(CH$_2$)$_2$OCH$_3$ | $C_{23}H_{29}N_7O_3$ | 452.23 | 452.1 |
| 3-6 | 2 | —C$_2$H$_5$ | $C_{23}H_{29}N_7O_2$ | 436.24 | 436.2 |

TABLE 3-continued

| Ex No. | n | R⁸ | Formula | Calc [M + H]⁺ | Found [M + H]⁺ |
|---|---|---|---|---|---|
| 3-7 | 2 | —CH₂—iPr | C₂₅H₃₃N₇O₂ | 464.27 | 464.2 |
| 3-8 | 2 | —CH₂CH=CH₂ | C₂₄H₂₉N₇O₂ | 448.24 | 448.2 |
| 3-9 | 2 | —(CH₂)₂OCH₃ | C₂₄H₃₁N₇O₃ | 466.25 | 466.2 |
| 3-10 | 2 | —CH₂-cpropyl | C₂₅H₃₁N₇O₂ | 462.25 | 462.2 |
| 3-11 | 2 | —CH₂CN | C₂₄H₂₇N₇O₂ | 446.22 | 446.2 |
| 3-12 | 2 | —CH(CH₃)C₂H₅ | C₂₅H₃₃N₇O₂ | 464.27 | 464.2 |
| 3-13 | 2 | —CH₂-tetrahydrofuran-2-yl | C₂₆H₃₃N₇O₃ | 492.26 | 492.2 |
| 3-14 | 2 | —(CH₂)₂CN | C₂₅H₂₉N₇O₂ | 460.24 | 460.2 |

TABLE 4

| Ex No. | n | R⁹ | Formula | Calc [M + H]⁺ | Found [M + H]⁺ |
|---|---|---|---|---|---|
| 4-1 | 1 | —CH₃ | C₂₀H₂₅N₇O₂S | 428.18 | 428.2 |
| 4-2 | 1 | —iPr | C₂₂H₂₉N₇O₂S | 456.21 | 456.2 |
| 4-3 | 1 | —CH₂—iPr | C₂₃H₃₁N₇O₂S | 470.23 | 470.2 |
| 4-4 | 1 | cyclopropyl | C₂₂H₂₇N₇O₂S | 454.20 | 454.2 |
| 4-5 | 1 | cyclopentyl | C₂₄H₃₁N₇O₂S | 482.23 | 482.2 |
| 4-6 | 1 | azetidin-1-yl | C₂₂H₂₈N₈O₂S | 469.21 | 469.2 |
| 4-7 | 1 | (1-ethylcyclopropyl) | C₂₄H₃₁N₇O₂S | 482.23 | 482.2 |
| 4-8 | 1 | (1-methylcyclopropyl) | C₂₃H₂₉N₇O₂S | 468.21 | 468.2 |
| 4-9 | 1 | azetidin-3-yl | C₂₂H₂₈N₈O₂S | 469.21 | 469.2 |

TABLE 4-continued

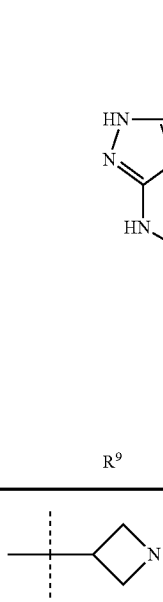

| Ex No. | n | R⁹ | Formula | Calc [M + H]⁺ | Found [M + H]⁺ |
|---|---|---|---|---|---|
| 4-10 | 1 | 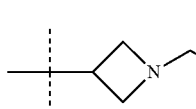 | $C_{24}H_{32}N_8O_2S$ | 497.24 | 497.2 |
| 4-11 | 1 | 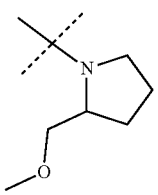 | $C_{25}H_{31}N_9O_2S$ | 522.23 | 522.2 |
| 4-12 | 1 | 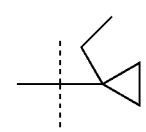 | $C_{25}H_{34}N_8O_3S$ | 527.25 | 527.6 |
| 4-13 | 1 | —CH₂-phenyl | $C_{26}H_{29}N_7O_2S$ | 504.21 | 504.1 |
| 4-14 | 1 | pyridin-2-yl | $C_{24}H_{26}N_8O_2S$ | 491.19 | 491.1 |
| 4-15 | 1 | 5-fluoropyridin-3-yl | $C_{24}H_{25}FN_8O_2S$ | 509.18 | 509.1 |
| 4-16 | 2 | —CH₃ | $C_{21}H_{27}N_7O_2S$ | 442.20 | 442.2 |
| 4-17 | 2 | —CH₂—iPr | $C_{24}H_{33}N_7O_2S$ | 484.24 | 484.2 |
| 4-18 | 2 | cyclopropyl | $C_{23}H_{29}N_7O_2S$ | 468.21 | 468.2 |
| 4-19 | 2 | —(CH₂)₂OCH₃ | $C_{23}H_{31}N_7O_3S$ | 486.22 | 486.2 |
| 4-20 | 2 | 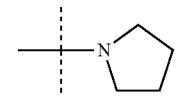 | $C_{25}H_{33}N_7O_2S$ | 496.24 | 496.2 |
| 4-21 | 2 | azetidin-3-yl | $C_{23}H_{30}N_8O_2S$ | 483.22 | 483.2 |
| 4-22 | 2 | —CH₂CH=CH₂ | $C_{23}H_{29}N_7O_2S$ | 468.21 | 468.6 |
| 4-23 | 2 | —CH₂-cyclopropyl | $C_{24}H_{31}N_7O_2S$ | 482.23 | 482.6 |
| 4-24 | 2 | —CH₂-phenyl | $C_{27}H_{31}N_7O_2S$ | 518.23 | 518.1 |
| 4-25 | 2 | 4-methylpyridin-3-yl | $C_{26}H_{30}N_8O_2S$ | 519.22 | 519.2 |
| 4-26 | 2 | —CH₂—pyridin-3-yl | $C_{26}H_{30}N_8O_2S$ | 519.22 | 519.2 |
| 4-27 | 2 |  | $C_{24}H_{32}N_8O_2S$ | 497.24 | 497.6 |

TABLE 4-continued

[Structure: pyrazole-naphthyridine with bicyclic amine bearing SO2-R9 substituent]

| Ex No. | n | R⁹ | Formula | Calc [M + H]⁺ | Found [M + H]⁺ |
|---|---|---|---|---|---|
| 4-28 | 2 | 2-(methoxymethyl)pyrrolidin-1-yl (via gem-dimethyl linker) | $C_{26}H_{36}N_8O_3S$ | 541.26 | 541.8 |
| 4-29 | 2 | azetidin-1-yl | $C_{23}H_{30}N_8O_2S$ | 483.22 | 483.2 |

TABLE 5

[Structure: pyrazole-naphthyridine with bicyclic amine bearing R¹, and R² on naphthyridine]

| Ex No. | n | R² | R¹ | Formula | Calc [M + H]⁺ | Found [M + H]⁺ |
|---|---|---|---|---|---|---|
| 5-1 | 1 | —OCH₃ | —CH₂CF₃ | $C_{22}H_{26}F_3N_7O$ | 462.22 | 462.1 |
| 5-2 | 1 | —OCH₃ | —(CH₂)₃CN | $C_{24}H_{30}N_8O$ | 447.25 | 447.2 |
| 5-3 | 1 | —OCH₃ | —CH₂CH₂F | $C_{22}H_{28}FN_7O$ | 426.23 | 426.2 |
| 5-4 | 1 | —OCH₃ | —CH₂-iPr | $C_{24}H_{33}N_7O$ | 436.27 | 436.2 |
| 5-5 | 1 | —OCH₃ | —(CH₂)₂CH₂F | $C_{23}H_{30}FN_7O$ | 440.25 | 440.1 |
| 5-6 | 1 | —OCH₃ | 2-methyl-1-(1-(trifluoromethyl)cyclopropyl)propan-1-one-yl | $C_{25}H_{28}F_3N_7O_2$ | 516.23 | 516 |
| 5-7 | 1 | —OCH₃ | —C(O)OCH₂CH=CH₂ | $C_{24}H_{29}N_7O_3$ | 464.23 | 464 |
| 5-8 | 1 | —OCH₃ | —(CH₂)₂CN | $C_{23}H_{28}N_8O$ | 433.24 | 433.1 |
| 5-9 | 1 | —OCH₃ | —S(O)₂CH₃ | $C_{24}H_{27}N_7O_3S$ | 458.19 | 458 |
| 5-10 | 2 | —OCH₃ | —(CH₂)₂CN | $C_{24}H_{30}N_8O$ | 447.25 | 447.1 |
| 5-11 | 1 | —CH₂OH | —(CH₂)₂CN | $C_{23}H_{28}N_8O$ | 433.24 | 433.2 |
| 5-12 | 1 | —CH₂OH | —S(O)₂CH₃ | $C_{21}H_{27}N_7O_3S$ | 458.19 | 458.1 |
| 5-13 | 1 | —CH₂OH | —S(O)₂C₂H₅ | $C_{22}H_{29}N_7O_3S$ | 472.21 | 472.1 |

TABLE 5-continued

| Ex No. | n | R² | R¹ | Formula | Calc [M + H]⁺ | Found [M + H]⁺ |
|---|---|---|---|---|---|---|
| 5-14 | 1 | —CH₂OH | —(CH₂)₂CH₂F | C₂₂H₂₈FN₇O | 426.23 | 426.2 |
| 5-15 | 1 | morpholinomethyl | —S(O)₂CH₃ | C₂₅H₃₄N₈O₃S | 527.25 | 527.6 |
| 5-16 | 1 | morpholinomethyl | —S(O)₂C₂H₅ | C₂₆H₃₆N₈O₃S | 541.26 | 541.8 |
| 5-17 | 1 | morpholinomethyl | —C(O)OCH₂CH=CH₂ | C₂₈H₃₆N₈O₃ | 533.29 | 533.8 |
| 5-18 | 1 | morpholinomethyl | —(CH₂)₂CN | C₂₇H₃₅N₉O | 502.30 | 502.8 |
| 5-19 | 1 | morpholinomethyl | —CH₂—iPr | C₂₈H₄₀N₈O | 505.33 | 505.3 |
| 5-20 | 1 | morpholinomethyl | (5-fluoropyridin-3-yl)sulfonyl | C₂₉H₃₄FN₉O₃S | 608.25 | 608 |
| 5-21 | 1 | morpholinomethyl | azetidin-1-ylsulfonyl | C₂₇H₃₇N₉O₃S | 568.27 | 568.2 |
| 5-22 | 2 | morpholinomethyl | —S(O)₂CH₃ | C₂₆H₃₆N₈O₃S | 541.26 | 541.8 |

TABLE 5-continued
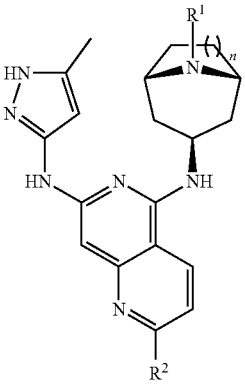
| Ex No. | n | R² | R¹ | Formula | Calc [M + H]⁺ | Found [M + H]⁺ |
|---|---|---|---|---|---|---|
| 5-23 | 2 | 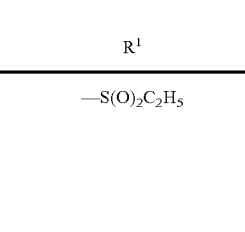 | —S(O)₂C₂H₅ | $C_{27}H_{38}N_8O_3S$ | 555.28 | 555.8 |
| 5-24 | 2 | 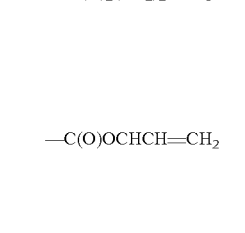 | —S(O)₂(CH₂)₂OCH₃ | $C_{28}H_{40}N_8O_4S$ | 585.29 | 585.8 |
| 5-25 | 2 | 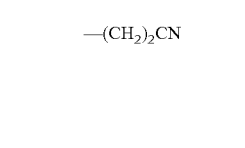 | —C(O)OCHCH=CH₂ | $C_{29}H_{38}N_8O_3$ | 547.31 | 547.8 |
| 5-26 | 2 | 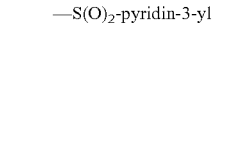 | —(CH₂)₂CN | $C_{28}H_{37}N_9O$ | 516.31 | 516.8 |
| 5-27 | 2 | 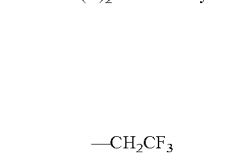 | —S(O)₂-pyridin-3-yl | $C_{30}N_{37}N_9O_3S$ | 604.27 | 604.1 |
| 5-28 | 2 |  | —S(O)₂-azetidin-1-yl | $C_{28}H_{39}N_9O_3S$ | 582.29 | 582.1 |
| 5-29 | 2 | 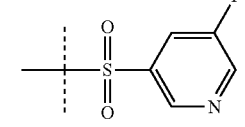 | —CH₂CF₃ | $C_{27}H_{35}F_3N_8O$ | 545.29 | 545.2 |
| 5-30 | 2 | 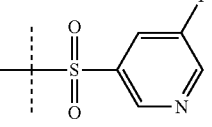 | | $C_{30}H_{36}FN_9O_3S$ | 622.26 | 622.2 |

TABLE 5-continued

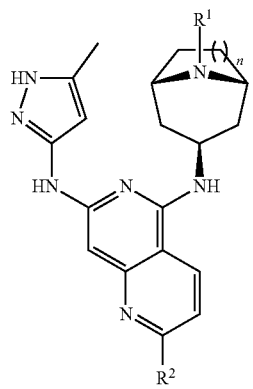

| Ex No. | n | R² | R¹ | Formula | Calc [M + H]⁺ | Found [M + H]⁺ |
|---|---|---|---|---|---|---|
| 5-31 | 1 | 4,4-difluoropiperidinylmethyl | 5-fluoropyridin-3-yl sulfonyl | $C_{30}H_{34}F_3N_9O_2S$ | 642.25 | 642 |
| 5-32 | 1 | 4,4-difluoropiperidinylmethyl | 1-ethylcyclopropyl sulfonyl | $C_{30}H_{40}F_2N_8O_2S$ | 615.30 | 615 |
| 5-33 | 1 | 4,4-difluoropiperidinylmethyl | —CH₂CF₃ | $C_{27}H_{33}F_5N_8$ | 565.28 | 565.2 |
| 5-34 | 1 | 4,4-difluoropiperidinylmethyl | —CH₂—iPr | $C_{29}H_{40}F_2N_8$ | 539.33 | 539.3 |
| 5-35 | 1 | 4-methylpiperazinylmethyl | —CH₂CF₃ | $C_{27}H_{36}F_3N_9$ | 544.30 | 544.3 |
| 5-36 | 1 | 4-methylpiperazinylmethyl | 1-ethylcyclopropyl sulfonyl | $C_{30}H_{43}N_9O_2S$ | 594.33 | 594.3 |
| 5-37 | 1 | 4-methylpiperazinylmethyl | —(CH₂)₂CN | $C_{28}H_{38}N_{10}$ | 515.33 | 515.3 |
| 5-38 | 1 | 4-methylpiperazinylmethyl | —CH₂—iPr | $C_{29}H_{43}N_9$ | 518.36 | 518.3 |
| 5-39 | 1 | 4-methylpiperazinylmethyl | azetidinylsulfonyl | $C_{28}H_{40}N_{10}O_2S$ | 581.31 | 581.3 |

TABLE 5-continued

[Structure: pyrazole-NH linked to naphthyridine core with NH-bicyclic amine bearing R¹, and R² substituent]

| Ex No. | n | R² | R¹ | Formula | Calc [M + H]⁺ | Found [M + H]⁺ |
|---|---|---|---|---|---|---|
| 5-40 | 1 | -CH₂-C(CH₃)(F)-CH₂-(4-methylpiperazin-1-yl) | -S(O)₂-(5-fluoropyridin-3-yl) | $C_{30}H_{37}FN_{10}O_2S$ | 621.28 | 621.2 |
| 5-41 | 1 | —CH₂S(O)₂CH₃ | —CH₂CH₂F | $C_{23}H_{30}FN_7O_2S$ | 488.22 | 488.1 |
| 5-42 | 1 | —CH₂S(O)₂CH₃ | —(CH₂)₂CH₂F | $C_{24}H_{32}FN_7O_2S$ | 502.23 | 502.1 |
| 5-43 | 1 | —CH₂S(O)₂CH₃ | —(CH₂)₂CF₃ | $C_{24}H_{30}F_3N_7O_2S$ | 538.21 | 538.1 |

TABLE 6

[Structure: pyrazole-NH linked to naphthyridine core with NH-bicyclic amine bearing R¹, and R³ substituent]

| Ex No. | n | R³ | R¹ | Formula | Calc [M + H]⁺ | Found [M + H]⁺ |
|---|---|---|---|---|---|---|
| 6-1 | 1 | —CH₃ | —(CH₂)₂CN | $C_{23}H_{28}N_8$ | 417.24 | 417.2 |
| 6-2 | 1 | —CH₃ | —CH₂-pyridin-4-yl | $C_{26}H_{30}N_8$ | 455.26 | 455.2 |
| 6-3 | 1 | —CH₃ | —C(O)OCH₂—iPr | $C_{25}H_{33}N_7O_2$ | 464.27 | 464.2 |
| 6-4 | 1 | —CH₃ | —S(O)₂-N(azetidin-3-carbonitrile) | $C_{24}H_{29}N_9O_2S$ | 508.22 | 508.2 |
| 6-5 | 1 | —CH₃ | —S(O)₂CH₃ | $C_{24}H_{27}N_7O_2S$ | 442.20 | 442.1 |
| 6-5 | 2 | —CH₃ | —(CH₂)₂CN | $C_{24}H_{30}N_8$ | 431.26 | 431.2 |
| 6-7 | 2 | —CH₃ | —C(O)OCH₂—iPr | $C_{26}H_{35}N_7O_2$ | 478.29 | 478.2 |
| 6-8 | 2 | —CH₃ | —S(O)₂CH₃ | $C_{22}H_{29}N_7O_2S$ | 456.21 | 456.2 |
| 6-9 | 2 | —CH₃ | —S(O)₂-N(azetidin-3-carbonitrile) | $C_{25}H_{31}N_9O_2S$ | 522.23 | 522.1 |
| 6-10 | 2 | —CH₃ | —CH₂-pyridin-4-yl | $C_{27}H_{32}N_8$ | 469.28 | 469.3 |

TABLE 6-continued

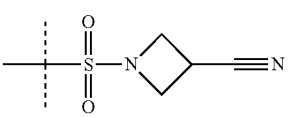

| Ex No. | n | R³ | R¹ | Formula | Calc [M + H]⁺ | Found [M + H]⁺ |
|---|---|---|---|---|---|---|
| 6-11 | 1 | —OCH₃ | —(CH₂)₂CN | C₂₃H₂₈N₈O | 433.24 | 433.1 |
| 6-12 | 1 | —OCH₃ | —(CH₂)₃CN | C₂₄H₃₀N₈O | 447.25 | 447.2 |
| 6-13 | 1 | —OCH₃ | —CH₂CH₂F | C₂₂H₂₈FN₇O | 426.23 | 426.1 |
| 6-14 | 1 | —OCH₃ | —CH₂—iPr | C₂₄H₃₃N₇O | 436.27 | 436.2 |
| 6-15 | 1 | —OCH₃ | —(CH₂)₂CF₃ | C₂₃H₂₈F₃N₇O | 476.23 | 476.1 |
| 6-16 | 1 | —OCH₃ | —(CH₂)₂CH₂F | C₂₃H₃₀FN₇O | 440.25 | 440.2 |
| 6-17 | 1 | —OCH₃ | —CH₂CF₃ | C₂₂H₂₆F₃N₇O | 462.22 | 462.1 |
| 6-18 | 1 | —OCH₃ | —S(O)₂CH₃ | C₂₁H₂₇N₇O₃S | 458.19 | 458.1 |
| 6-19 | 1 | —OCH₃ | —C(O)OCH₂CH=CH₂ | C₂₄H₂₉N₇O₃ | 464.23 | 464.1 |
| 6-20 | 1 | —OCH₃ | 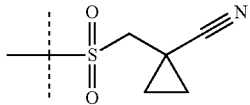 | C₂₄H₂₉N₉O₃S | 524.21 | 524.1 |
| 6-21 | 1 | —OCH₃ | —S(O)₂(CH₂)₃CN | C₂₄H₃₀N₈O₃S | 511.22 | 511.1 |
| 6-22 | 1 | —OCH₃ | —S(O)₂(CH₂)₂CN | C₂₃H₂₈N₈O₃S | 497.20 | 497.2 |
| 6-23 | 1 | —OCH₃ | 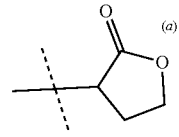 | C₂₅H₃₀N₈O₃S | 523.22 | 523.2 |
| 6-24 | 1 | —OCH₃ | —CH₂-pyridin-4-yl | C₂₆H₃₀N₈O | 471.25 | 471.2 |
| 6-25 | 1 | —OCH₃ | —C(O)OCH₂—iPr | C₂₅H₃₃N₇O₃ | 480.26 | 480.2 |
| 6-26 | 2 | —OCH₃ | —(CH₂)₂CH₂F | C₂₄H₃₂FN₇O | 454.27 | 454.2 |
| 6-27 | 2 | —OCH₃ | —C(O)CH((S)OH)CH₃ | C₂₄H₃₁N₇O₃ | 466.25 | 466.2 |
| 6-28 | 2 | —OCH₃ | —CH₂-pyridin-4-yl | C₂₇H₃₂N₈O | 485.27 | 485.2 |
| 6-29 | 2 | —OCH₃ | —S(O)₂CH₃ | C₂₂H₂₉N₇O₃S | 472.21 | 472.1 |
| 6-30 | 2 | —OCH₃ | —C(O)CH₂N(CH₃)₂ | C₂₅H₃₄N₈O₂ | 479.28 | 479.3 |
| 6-31 | 2 | —OCH₃ | —(CH₂)₂CN | C₂₄H₃₀N₈O | 447.25 | 447.2 |
| 6-32 | 1 | —C(O)OCH₃ | —(CH₂)₂CN | C₂₄H₂₈N₈O₂ | 461.23 | 461.2 |
| 6-33 | 1 | —C(O)OCH₃ | —S(O)₂CH₃ | C₂₂H₂₇N₇O₄S | 486.18 | 468.1 |
| 6-34 | 1 | —C(O)OCH₃ | —S(O)₂C₂H₅ | C₂₃H₂₉N₇O₄S | 500.20 | 500.2 |
| 6-35 | 1 | —C(O)OCH₃ | (a) | C₂₅H₂₉N₇O₄ | 492.23 | 492.1 |
| 6-36 | 1 | —C(O)OCH₃ | —C(O)C₂H₅ | C₂₄H₂₀N₇O₃ | 464.23 | 464.2 |
| 6-37 | 1 | —C(O)OCH₃ | —C(O)CHF₂ | C₂₃H₂₅F₂N₇O₃ | 486.20 | 468.2 |
| 6-38 | 1 | —C(O)OCH₃ | —C(O)CH((S)CH₃)C₂H₅ | C₂₆H₃₃N₇O₃ | 492.26 | 492.2 |
| 6-39 | 1 | —C(O)OCH₃ | —C(O)CH₂N(CH₃)₂ | C₂₅H₃₂N₈O₃ | 493.26 | 493.2 |
| 6-40 | 1 | —C(O)OCH₃ | —C(O)OCH₂CH=CH₂ | C₂₅H₂₉N₇O₄ | 492.23 | 492.2 |
| 6-41 | 1 | —C(O)OCH₃ | —CH₂C(O)O—iPr | C₂₆H₃₃N₇O₄ | 508.26 | 508.2 |
| 6-42 | 1 | —C(O)OCH₃ | —CH₂C(O)NHCH₃ | C₂₄H₃₀N₈O₃ | 479.24 | 479.5 |
| 6-43 | 1 | —C(O)OCH₃ | —CH₂CH₂F | C₂₃H₂₈FN₇O₂ | 454.23 | 454.2 |
| 6-44 | 1 | —C(O)OCH₃ | —(CH₂)₂CH₂F | C₂₄H₃₀FN₇O₂ | 468.24 | 468.2 |
| 6-45 | 1 | —C(O)OCH₃ | —(CH₂)₂CF₃ | C₂₄H₂₈F₃N₇O₂ | 504.23 | 504.2 |

TABLE 6-continued

| Ex No. | n | R³ | R¹ | Formula | Calc [M + H]⁺ | Found [M + H]⁺ |
|---|---|---|---|---|---|---|
| 6-46 | 1 | —C(O)OCH₃ | (R)-γ-butyrolactonyl-CH₂— | C₂₆H₃₁N₇O₄ | 506.24 | 507.2 |
| 6-47 | 2 | —C(O)OCH₃ | —(CH₂)₂CN | C₂₅H₃₀N₈O₂ | 475.25 | 475.2 |
| 6-48 | 2 | —C(O)OCH₃ | δ-valerolactonyl | C₂₇H₃₃N₇O₄ | 520.26 | 520.2 |
| 6-49 | 2 | —C(O)OCH₃ | (R)-γ-butyrolactonyl-CH₂— | C₂₇H₃₃N₇O₄ | 520.26 | 520.2 |
| 6-50 | 1 | —S(O)₂CH₃ | —(CH₂)₂CN | C₂₃H₂₈N₈O₂S | 481.21 | 481.2 |
| 6-51 | 1 | —S(O)₂CH₃ | —C(O)CH₂CN | C₂₃H₂₆N₈O₃S | 495.19 | 495.2 |
| 6-52 | 1 | —S(O)₂CH₃ | —C(O)CHF₂ | C₂₂H₂₅F₂N₇O₃S | 506.17 | 506.2 |
| 6-53 | 1 | —S(O)₂CH₃ | —CH((S)CH₃)C₂H₅ | C₂₅H₃₃N₇O₃S | 512.24 | 512.2 |
| 6-54 | 1 | —S(O)₂CH₃ | —CH₂CH₂F | C₂₂H₂₈FN₇O₂S | 474.20 | 474.2 |
| 6-55 | 1 | —S(O)₂CH₃ | —(CH₂)₂CH₂F | C₂₃H₃₀FN₇O₂S | 488.22 | 488.2 |
| 6-56 | 1 | —S(O)₂CH₃ | —(CH₂)₂CF₃ | C₂₃H₂₈F₃N₇O₂S | 524.20 | 524.2 |
| 6-57 | 1 | —S(O)₂CH₃ | (S)-γ-butyrolactonyl | C₂₄H₂₉N₇O₄S | 512.20 | 512.1 |
| 6-58 | 1 | —S(O)₂CH₃ | (R)-γ-butyrolactonyl | C₂₄H₂₉N₇O₄S | 512.20 | 512.2 |
| 6-59 | 1 | —S(O)₂CH₃ | —CH₂-pyridin-4-yl | C₂₆H₃₀N₈O₂S | 519.22 | 519.1 |
| 6-60 | 2 | —S(O)₂CH₃ | —CH₂-pyridin-4-yl | C₂₇H₃₂N₈O₂S | 533.24 | 533.1 |

(a)Stereoisomers separated but not identified

TABLE 7

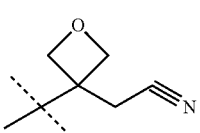

| Ex No. | n | R⁴ | R¹ | Formula | Calc [M + H]⁺ | Found [M + H]⁺ |
|---|---|---|---|---|---|---|
| 7-1 | 1 | —OCH$_3$ | —C(O)OCH$_2$—iPr | C$_{25}$H$_{33}$N$_7$O$_3$ | 480.26 | 480.1 |
| 7-2 | 1 | —OCH$_3$ | —S(O)$_2$C$_2$H$_5$ | C$_{22}$H$_{29}$N$_7$O$_3$S | 472.21 | 472.1 |
| 7-3 | 1 | —OCH$_3$ | —C(O)CH$_2$N(CH$_3$)$_2$ | C$_{24}$H$_{32}$N$_8$O$_2$ | 465.27 | 465.1 |
| 7-4 | 1 | —OCH$_3$ | —C(O)CH(CH$_3$)C$_2$H$_5$ | C$_{25}$H$_{33}$N$_7$O$_2$ | 464.27 | 464.2 |
| 7-5 | 1 | —OCH$_3$ | —C(O)CHF$_2$ | C$_{22}$H$_{25}$F$_2$N$_7$O$_2$ | 458.20 | 458.1 |
| 7-6 | 1 | —OCH$_3$ | —(CH$_2$)$_2$CN | C$_{23}$H$_{28}$N$_8$O | 433.24 | 433.2 |
| 7-7 | 1 | —OCH$_3$ | —CH$_2$CH$_2$F | C$_{22}$H$_{28}$FN$_7$O | 426.23 | 426.2 |
| 7-8 | 1 | —OCH$_3$ | —CH$_2$CHF$_2$ | C$_{22}$H$_{27}$F$_2$N$_7$O | 444.22 | 444.1 |
| 7-9 | 1 | —OCH$_3$ | —CH$_2$CF$_3$ | C$_{22}$H$_{26}$F$_3$$_1$N$_7$O | 462.22 | 462.1 |
| 7-10 | 1 | —OCH$_3$ | ![oxetane-CH2CN group] | C$_{25}$H$_{30}$N$_8$O$_2$ | 475.25 | 475.2 |

TABLE 8

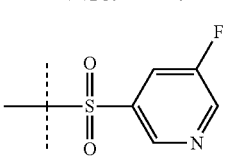

| Ex No. | n | R³ | R¹ | Formula | Calc [M + H]⁺ | Found [M + H]⁺ |
|---|---|---|---|---|---|---|
| 8-1 | 1 | H | —(CH$_2$)$_2$CN | C$_{22}$H$_{25}$FN$_8$ | 421.22 | 421.2 |
| 8-2 | 1 | H | —S(O)$_2$CH$_3$ | C$_{20}$H$_{24}$FN$_7$O$_2$S | 446.17 | 446.1 |
| 8-3 | 1 | H | —S(O)$_2$C$_2$H$_5$ | C$_{24}$H$_{26}$FN$_7$O$_2$S | 460.19 | 460.2 |
| 8-4 | 1 | H | —S(O)$_2$-pyridin-3-yl | C$_{24}$H$_{25}$FN$_8$O$_2$S | 509.18 | 509.2 |
| 8-5 | 1 | H | (5-fluoropyridin-3-yl sulfonyl-C(CH$_3$)) | C$_{24}$H$_{24}$F$_2$N$_8$O$_2$S | 527.17 | 527.1 |
| 8-6 | 1 | H | —CH$_2$-pyridin-4-yl | C$_{25}$H$_{27}$FN$_8$ | 459.23 | 459.2 |
| 8-7 | 1 | H | —C(O)CH$_2$N(CH$_3$)$_2$ | C$_{23}$H$_{29}$FN$_8$O | 453.25 | 453.2 |
| 8-8 | 1 | H | —C(O)CH((S)OH)CH$_3$ | C$_{22}$H$_{26}$FN$_7$O$_2$ | 440.21 | 440.2 |
| 8-9 | 2 | H | —(CH$_2$)$_2$CN | C$_{23}$H$_{27}$FN$_8$ | 435.23 | 435.2 |
| 8-10 | 2 | H | —S(O)$_2$CH$_3$ | C$_{21}$H$_{26}$FN$_7$O$_2$S | 460.19 | 460.6 |
| 8-11 | 2 | H | —S(O)$_2$-phenyl | C$_{26}$H$_{28}$FN$_7$O$_2$S | 522.20 | 522.2 |
| 8-12 | 2 | H | —S(O)$_2$-pyridin-3-yl | C$_{25}$H$_{27}$FN$_8$O$_2$S | 523.20 | 523.1 |

TABLE 8-continued

[Structure: pyrazole-NH and azabicyclic-NH substituted naphthyridine with F and R³ substituents; R¹ on bridgehead N⁺, with n designation]

| Ex No. | n | R³ | R¹ | Formula | Calc [M + H]⁺ | Found [M + H]⁺ |
|---|---|---|---|---|---|---|
| 8-13 | 2 | H | [3-fluoropyridin-5-yl sulfonyl methyl group] | $C_{25}H_{26}F_2N_8O_2S$ | 541.19 | 541.1 |
| 8-14 | 2 | H | —CH₂-pyridin-4-yl | $C_{26}H_{29}FN_8$ | 473.25 | 473.2 |
| 8-15 | 2 | H | —C(O)CH₂N(CH₃)₂ | $C_{24}H_{31}FN_8O$ | 467.26 | 467.2 |
| 8-16 | 2 | H | —C(O)CH((S)OH)CH₃ | $C_{23}H_{28}FN_7O_2$ | 454.23 | 454.2 |
| 8-17 | 1 | —CH₃ | —S(O)₂CH₃ | $C_{21}H_{26}FN_7O_2S$ | 460.19 | 460.1 |
| 8-18 | 1 | —CH₃ | —(CH₂)₂CN | $C_{23}H_{27}FN_8$ | 435.23 | 435.1 |
| 8-19 | 1 | —CH₃ | [—S(O)₂-N-(3-cyanoazetidinyl)] | $C_{24}H_{28}FN_9O_2S$ | 526.21 | 526.1 |
| 8-20 | 1 | —CH₃ | —S(O)₂-pyridin-3-yl | $C_{25}H_{27}FN_8O_2S$ | 523.20 | 523.1 |
| 8-21 | 2 | —CH₃ | —(CH₂)₂CN | $C_{24}H_{29}FN_8$ | 449.25 | 449.2 |
| 8-22 | 2 | —CH₃ | —S(O)₂CH₃ | $C_{22}H_{28}FN_7O_2S$ | 474.20 | 474.1 |
| 8-23 | 2 | —CH₃ | [—S(O)₂-N-(3-cyanoazetidinyl)] | $C_{25}H_{30}FN_9O_2S$ | 540.22 | 540.2 |
| 8-24 | 2 | —CH₃ | —S(O)₂-pyridin-3-yl | $C_{26}H_{29}FN_8O_2S$ | 537.21 | 537.1 |

Example 18: Crystalline Solvate 3-((1R,3s,5S)-3-((7-((5-methyl-1H-pyrazol-3-yl)amino)-1,6-naphthyridin-5-yl)amino)-8-azabicyclo[3.2.1]octan-8-yl) propanenitrile Form II (a) tert-butyl ((1R,3s,5S)-3-((7-chloro-1,6-naphthyridin-5-yl)amino)-8-azabicyclo[3.2.1]octane-8-carboxylate To a 2 L flask was added 5,7-dichloro-1,6-naphthyridine (45.8 g, 230 mmol), tert-butyl (1R,3s,5S)-3-amino-8-azabicyclo[3.2.1]octane-8-carboxylate (54.7 g, 242 mmol), and DMSO (458 mL) followed by DIPEA (64.3 mL, 368 mmol). The reaction mixture was heated at 110° C. for 12 h, cooled to ambient temperature and water (458 mL) was added slowly over 45 min. After 2 h, the reaction mixture was filtered and washed with 1:1 DMSO:water (60 mL) to give a wet solid product (65 g). The solid was washed in four portions with MTBE (500 mL) to give the title intermediate (74 g, 190 mmol, 83% yield) (HPLC Method 3 Retention time 20.20 min) and the filtrate which was concentrated to give a solid (19.5 g), mainly product. Heptane (195 mL) was added to the solid (19.5 g) and the reaction mixture was stirred for 2 h, filtered and washed with heptane to give another portion of the title intermediate (12.3 g, 31.6 mmol, 13.75% yield) HPLC Method 3 Retention time 20.20 min.

(b) tert-butyl ((1R,3s,5S)-3-((7-((5-methyl-1H-pyrazol-3-yl)amino)-1,6-naphthyridin-5-yl)amino)-8-azabicyclo[3.2.1]octane-8-carboxylate A mixture of tert-butyl ((1R,3s,5S)-3-((7-chloro-1,6-naphthyridin-5-yl)amino)-8-azabicyclo[3.2.1]octane-8-carboxylate (30 g, 77 mmol), tert-butyl 3-amino-5-methyl-1H-pyrazole-1-carboxylate (19.78 g, 100 mmol), Cs₂CO₃ (50.3 g, 154 mmol), PdXPhos (1.517 g, 1.93 mmol) and XPhos (0.919 g, 1.93 mmol) was degassed with nitrogen 3 times, and then 1,4-dioxane (300 mL) was added. The reaction mixture was degassed with nitrogen 5 times, heated to reflux, stirred for 16 h, and cooled to 75° C. Water (90 mL) was added and the reaction mixture was heated to reflux and stirred at reflux for 48 h. Water (210 mL) was added slowly and the reaction mixture was stirred at RT fort 1 h, and filtered. The filter cake was washed with 1:1 dioxane:water (50 mL) and dried at 50° C. under vacuum overnight to give crude title intermediate (35.34 g).

The crude product was dissolved in DMF (173 mL). SiliaMetS® thiol functionalized silica (8.65 g) was added and the reaction mixture was stirred for 45 min at 80° C., cooled to RT, filtered, and rinsed with DMF (35 mL). To the filtrate was added water (346 mL) dropwise and seeds from a previous preparation by the same procedure. The reaction mixture stirred at RT for 6 h, filtered, washed with water (35 mL) and dried at 50° C. under vacuum to give the title intermediate (33.6 g, 97% yield). HPLC Method 3 Retention time 16.89 min (c) $N^5$-((1R,3s,5S)-8-azabicyclo[3.2.1]octan-3-yl)-$N^7$-(5-methyl-1H-pyrazol-3-yl)-1,6-naphthyridine-5,7-diamine To a suspension of tert-butyl ((1R,3s,5S)-3-((7-((5-methyl-1H-pyrazol-3-yl)amino)-1,6-naphthyridin-5-yl)amino)-8-azabicyclo[3.2.1]octane-8-carboxylate (15.6 g, 34.7 mmol) in methanol (78 mL) was added 4 M HCl in dioxane (4 M) (87 mL, 347 mmol) at RT. The reaction mixture was stirred for 2 h, and diisopropyl ether (156 mL) was added dropwise. The reaction mixture was stirred for 18 h, filtered, washed with diisopropyl ether (20 mL) and dried at 50° C. under vacuum for 2 h to give the 3wHCl salt of the title intermediate (11.33 g, 71.2% yield). HPLC Method 3 Retention time 9.87 min.

(d) 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile (crude)

To a mixture of the product of the previous step (11.24 g, 24.50 mmol), DMF (56.2 mL), and methanol (5.75 mL) was added DBU (15 mL, 103 mmol) dropwise at RT followed by acrylonitrile (2.4 mL, 36.7 mmol) dropwise. The reaction mixture was stirred at RT for 3 h and then 2:1 methanol:water (225 mL) was added dropwise over 1 h. After 3 h, the reaction mixture was filtered, washed with 1:1 methanol:water (20 mL), and dried at 50° C. under vacuum overnight to provide the title compound (9.42 g, 96% yield).

(e) 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile To a mixture of crude 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile (38.6 g, 96 mmol) was added DMF (232 mL) followed by SiliaMetS® Thiol functionalized silica (1.41 mmol/g, 6.8 g). The mixture was warmed to 75° C. and stirred for 45 min at 75° C. The mixture was cooled to 25° C., filtered, rinsed with DMF (1 mL), and then 2:1 MeOH:water (926 mL) was added to the filtrate dropwise. The mixture was stirred at RT overnight, filtered, washed with 1:1 MeOH:water (40 mL) and dried at 50° C. under vacuum to give the title compound as a crystalline solvate (38 g, 94 mmol, 98% yield) HPLC Method 3 Retention time 10.23 min. Residual solvents by gas chromatography: methanol 6.6%, N,N-dimethylformamide 2.3%, water by Karl Fischer analysis 1.2%.

Example 19: Crystalline 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile Form I (a) $N^5$-((1R,3s,5S)-8-azabicyclo[3.2.1]octan-3-yl)-$N^7$-(5-methyl-1H-pyrazol-3-yl)-1,6-naphthyridine-5,7-diamine To a reactor was added the 3HCl salt of $N^5$-((1R,3s,5S)-8-azabicyclo[3.2.1]octan-3-yl)-$N^7$-(5-methyl-1H-pyrazol-3-yl)-1,6-naphthyridine-5,7-diamine (3.4 kg, 1 equiv), followed by water (34 kg, 10 equiv) and 1N HCl (7 kg, 2.05 equiv) to form a reaction mixture. Activated charcoal (0.22 kg, 0.064 equiv) was added, followed by SiliaMetS® thiol functionalized silica (1.7 kg, 0.5 equiv) and the reaction mixture was agitated at 80° C. for 16 h, cooled to 25° C., and filtered through a pad of Celite to Nalgene containers. The reactor was washed with water (13.6 kg, 4 equiv), which was transferred to wash the cake on the filter and collected in the Nalgene containers.

To the collected wash was added methanol (13.6 kg, 4 equiv). The temperature was adjusted to 20° C. and 30% w/v NaOH (4.4 kg, 1.29 equiv) was added slowly maintaining the temperature below 30° C. The resulting slurry was agitated for 3 h at 25° C., filtered, washed with water (17 kg, 5 equiv), and dried at 50° C. in vacuo for 12 h to provide the title intermediate (2.3 kg, HPLC purity 98.4%) HPLC Method 3 with 32 min gradient (time (min)/% B): 0/2, 10/20, 24/90, 27/90, 27.1/2, 32/2 Retention time 9.4 min (b) 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile (Crude)

To a reactor was added the product of the previous step (2.1 kg, 1 equiv), DMF (19.7 kg, 9.4 equiv), methanol (3.4 kg, 1.6 equiv), THF (9.5 kg, 4.5 equiv), and DBU (0.92 kg, 0.44 equiv) and the reaction mixture was agitated at 30° C. until fully dissolved. The temperature was adjusted to 20° C., acrylonitrile (0.48 kg, 0.23 equiv) was added, the reaction mixture was agitated for 16 h, water (52.5 kg, 25 equiv) was added, and the temperature was adjusted to 20° C. The resulting slurry was agitated for 3 h, filtered, washed with methanol (3.4 kg, 1.5 equiv) which had first washed the reactor, and dried at 50° C. in vacuo for 12 h. Ethanol (21 kg, 10 equiv) was added to the dry cake, and the resulting slurry was agitated at reflux for 4 h, cooled to 25° C., agitated at 25° C. for 1 h, and filtered. The wet cake was washed with ethanol (3.2 kg, 1.5 equiv) and dried at 50° C. in vacuo for 12 h to provide the title intermediate (1.8 kg, HPLC purity 99.8%)

(c) Crystalline solvate 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile Form II To a reactor was added the product of the previous step (1.5 kg, 1 equiv) and DMF (8.4 kg, 5.6 equiv) and the reaction mixture was heated to 25° C. and agitated for 5 min until fully dissolved. Methanol (14.3 kg, 9.5 equiv) and water (9.0 kg, 6 equiv) were added over 1 h. The resulting slurry was agitated for 16 h at 25° C., filtered, and washed with methanol (3.0 kg, 2 equiv) which had first washed the reactor, and dried at 50° C. in vacuo for 12 h to provide the title intermediate (1.4 kg, HPLC purity 99.8%).

(d) Crystalline 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile Form I

[Equivalents measured with respect to step (c).] To a reactor was added the product of the previous step (1.4 kg) followed by acetone (13.8 kg, 9.2 equiv) and the resulting slurry was agitated for 18 h at 45° C., cooled to 25° C., agitated at 25° C. for 30 min, filtered, washed with acetone (3.0 kg, 2 equiv) which had first washed the reactor, and dried at 50° C. in vacuo for 12 h to provide the title compound (1.2 kg, HPLC purity 99.8%) as a yellow crystalline solid. HPLC Column Agilent Poroshell EC C-18 150×4.6 mm, 2.7 μm, 45° C., 2.2 mL/min, 7 μL, 250 nm detection, Mobile Phase A: Water:ACN:TFA (99:1:0.1), Mobile Phase B: Water:ACN:TFA (10:90:0.1) Gradient 37 min (time (min)/% B) 0/4, 25/27, 30/100, 33/100, 33.1/4, 37/4 Retention Time 11.2 min. $^1$H NMR ($d_6$-DMSO, 600 mHz) δ (ppm) 11.75 (s, 1H), 8.76 (s, 1H), 8.57 (d, J=3 Hz, 1H), 8.41 (d, J=3 Hz, 1H), 7.15 (d, J=5 Hz, 1H), 6.96 (dd, J=3 Hz, 5 Hz, 1H), 6.67 (s, 1H), 6.20 (s, 1H), 4.55 (m, 1H), 3.33 (m, 2H), 2.63 (m, 4H), 2.22 (s, 3H), 1.70-1.93 (m, 8H).

Example 20: Crystalline 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile Form I (a) Crystalline solvate 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile Form II To a mixture of $N^5$-((1R,3s,5S)-8-azabicyclo[3.2.1]octan-3-yl)-$N^7$-(5-methyl-1H-pyrazol-3-yl)-1,6-naphthyridine-5,7-diamine (5 g, 14.31 mmol) and DMF (50 mL) was added DBU (5.39 mL, 35.8 mmol) followed by 3-bromopropionitrile (1.78 mL, 21.5 mmol) dropwise. The reaction mixture was stirred at 20-25° C. for 4 h and then 3:1 methanol:water (150 mL) was added dropwise over 60 min. The reaction mixture was stirred for 20 h at 20° C., filtered, washed with 3:1 methanol:water (10 mL), and dried in vacuo at 50° C. for 2 h to provide the title compound (5.07 g, 12.60 mmol, 88% yield) HPLC Method 3 Retention time 10.13 min.

To a mixture of the product of the previous step (1 g, 2.49 mmol) in DMF (6 mL) was added 3:1 methanol:water (18 mL) dropwise. After 3 h, the mixture was filtered, washed with methanol (2 mL), and dried in vacuo at 50° C. for 18 h to provide the title compound (0.94 g, 2.33 mmol, 94% yield) HPLC Method 3 Retention time 10.17 min.

(b) Crystalline 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile Form I A mixture of the product of the previous step (0.6 g, 1.49 mmol) and acetone (7.2 mL) was stirred at RT for 18 h, filtered, and washed with acetone to give the title compound (0.5 g, 1.24 mmol, 83% yield). HPLC Method 3 Retention time 10.03 min.

Example 21: Crystalline 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile Form I A mixture of 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile solvate Form II (100 g, 248 mmol) and 1,4-dioxane (1200 mL) was heated to 95° C., stirred for 10 h, cooled to RT, stirred for 3 h, filtered, washed with dioxane, and dried at 50° C. for 6 h and then at RT for 5 days to provide the title compound (87 g, 86% yield) HPLC Method 3 Retention time 10.21 min.

Example 22: Crystalline 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile Form I A mixture of 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile solvate Form II (5 g, 12.42 mmol) and toluene (75 mL) was heated to reflux for 4 h, cooled to RT over 30 min, stirred at RT for 30 min, filtered, and washed with toluene to provide the title compound (4.6 g, 92% yield).

Example 23: Crystalline 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile Form I A mixture of 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile ethanol solvate (1 g, 2.49 mmol) and butyl acetate (20 mL) was heated to 110° C. for 8 h, cooled to RT, stirred at RT for 65 h, filtered, and washed with water to provide the title compound (0.92 g, 92% yield). HPLC Method 3 Retention time 10.08 min.

Examples 24-27: Properties of the Solid Forms of the Invention

Samples of the Form I crystalline freebase and Form II crystalline solvate of 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile of Examples 19 and 18, respectively, were analyzed by powder X-ray diffraction (PXRD). Crystalline Form I of Example 19 was also analyzed by differential scanning calorimetry (DSC), thermogravimetric analysis (TGA), dynamic moisture sorption (DMS), and by single crystal x-ray diffraction.

Example 24 Powder X-Ray Diffraction

The powder X-ray diffraction patterns of FIGS. 1 and 5 were obtained with a Bruker D8-Advance X-ray diffractometer using Cu-Kα radiation (λ=1.54051 Å) with output voltage of 45 kV and current of 40 mA. The instrument was operated in Bragg-Brentano geometry with incident, divergence, and scattering slits set to maximize the intensity at the sample. For measurement, a small amount of powder (5-25 mg) was gently pressed onto a sample holder to form a smooth surface and subjected to X-ray exposure. The samples were scanned in 2θ-2θ mode from 2° to 400 in 2θ with a step size of 0.02° and a scan speed of 0.30° seconds per step. The data acquisition was controlled by Bruker DiffracSuite measurement software and analyzed by Jade software (version 7.5.1). The instrument was calibrated with a corundum standard, within ±0.020 two-theta angle. Observed PXRD two-theta peak positions and d-spacings are shown in Tables 9 and 10, respectively for crystalline Form I and the crystalline Form II solvate.

TABLE 9

PXRD Data for Crystalline Form I

| 2-Theta | d(Å) | Area | A % |
|---|---|---|---|
| 7.87 | 11.23 | 515.2 | 26.3 |
| 10.80 | 8.18 | 188.7 | 9.6 |
| 12.78 | 6.92 | 731.1 | 37.3 |
| 12.86 | 6.88 | 620.9 | 31.7 |
| 13.47 | 6.57 | 423.0 | 21.6 |
| 13.64 | 6.49 | 274.5 | 14.0 |
| 14.66 | 6.04 | 105.2 | 5.4 |
| 15.11 | 5.86 | 285.6 | 14.6 |
| 15.54 | 5.70 | 541.5 | 27.6 |
| 15.78 | 5.61 | 1959.5 | 100.0 |
| 17.75 | 4.99 | 356.7 | 18.2 |
| 18.00 | 4.92 | 201.7 | 10.3 |
| 20.41 | 4.35 | 944.3 | 48.2 |
| 20.54 | 4.32 | 938.4 | 47.9 |
| 21.00 | 4.23 | 303.1 | 15.5 |
| 22.22 | 4.00 | 502.1 | 25.6 |
| 22.79 | 3.90 | 158.5 | 8.1 |
| 22.93 | 3.88 | 272.8 | 13.9 |
| 23.49 | 3.79 | 639.2 | 32.6 |
| 23.65 | 3.76 | 1685.4 | 86.0 |
| 23.75 | 3.74 | 903.8 | 46.1 |
| 25.23 | 3.53 | 115.0 | 5.9 |
| 25.31 | 3.52 | 101.7 | 5.2 |
| 26.36 | 3.38 | 78.9 | 4.0 |
| 27.26 | 3.27 | 115.7 | 5.9 |
| 27.44 | 3.25 | 134.1 | 6.8 |

TABLE 10

PXRD Data for the Crystalline Form II solvate

| 2-Theta | d(Å) | Area | A % |
|---|---|---|---|
| 6.97 | 12.67 | 941.9 | 16.4 |
| 9.76 | 9.05 | 5759.9 | 100.0 |
| 10.17 | 8.69 | 803.6 | 14.0 |
| 11.56 | 7.65 | 531.9 | 9.2 |
| 12.68 | 6.97 | 1058.9 | 18.4 |
| 13.62 | 6.50 | 441.4 | 7.7 |
| 13.98 | 6.33 | 472.6 | 8.2 |
| 15.06 | 5.88 | 1170.0 | 20.3 |
| 16.61 | 5.33 | 2410.1 | 41.8 |
| 17.27 | 5.13 | 670.0 | 11.6 |
| 19.02 | 4.66 | 786.5 | 13.7 |
| 20.40 | 4.35 | 1472.6 | 25.6 |
| 21.04 | 4.22 | 1062.2 | 18.4 |
| 21.20 | 4.19 | 1578.9 | 27.4 |
| 21.99 | 4.04 | 5002.2 | 86.8 |
| 22.44 | 3.96 | 1663.1 | 28.9 |

Example 25: Thermal Analysis

Differential scanning calorimetry (DSC) was performed using a TA Instruments Model Q-100 module with a Thermal Analyst controller. Data were collected and analyzed using TA Instruments Thermal Analysis software. A sample of each crystalline form was accurately weighed into a covered aluminum pan. After a 5 minute isothermal equilibration period at 5° C., the sample was heated using a linear heating ramp of 10° C./min from 0° C. to 250° C. A representative DSC thermogram of the Form I crystalline freebase of the invention is shown in FIG. 2.

Thermogravimetric analysis (TGA) measurements were performed using a TA Instruments Model Q-50 module equipped with high resolution capability. Data were collected using TA Instruments Thermal Analyst controller and analyzed using TA Instruments Universal Analysis software. A weighed sample was placed onto a platinum pan and scanned with a heating rate of 10° C. from ambient temperature to 300° C. The balance and furnace chambers were purged with nitrogen flow during use. A representative TGA trace of the Form I crystalline freebase of the invention is shown in FIG. 3.

Example 26: Dynamic Moisture Sorption Assessment

Dynamic moisture sorption (DMS) measurement was performed using a VTI atmospheric microbalance, SGA-100 system (VTI Corp., Hialeah, FL 33016). A weighed sample was used and the humidity was lowest possible value (close to 0% RH) at the start of the analysis. The DMS analysis consisted of an initial drying step (0% RH) for 120 minutes, followed by two cycles of sorption and desorption with a scan rate of 5% RH/step over the humidity range of 5% RH to 90% RH. The DMS run was performed isothermally at 25° C. A representative DMS trace for the Form I crystalline freebase of the invention is shown in FIG. 4.

Example 27: Single Crystal X-Ray Diffraction

Intensity data were collected at 293° K, using Cu radiation (l=1.54184 Å), on an Oxford Diffraction Gemini-R Ultra diffractometer operated by the CrysAlis software. [Agilent Technologies (2012), Yarnton, England] (CrysAlis CCD and CrysAlis RED, 2003) The data were corrected for absorption effects by means of comparison of equivalent reflections. The structure was solved with the direct methods procedure implemented in SHELXT and refined by full-matrix least squares on $F^2$ using SHELXL-2014. [Sheldrick, *Acta Cryst.* C71 (2015), 3-8]. Non-hydrogen atoms were located in difference maps and refined anisotropically. Hydrogen atoms bonded to C atoms were fixed in idealized positions. Their thermal displacement parameters were refined freely, except for one of the methyl groups. H atoms bonded to N were refined using distance restraints, N—H=0.86(1) Å, and their thermal displacement parameters were refined freely.

Example 28: Solid State Stability Assessment

Samples of the Form I crystalline freebase of the invention were stored in zip-tie closed double polyethylene bags inside an HDPE bottle with screw cap at 25° C. and 60% relative humidity (RH) and at 40° C. and 75% RH. At specific intervals, the contents of a representative sample was removed and analyzed by HPLC for chemical purity and by Karl Fischer for water content.

TABLE 11

Crystalline Form I Stability Study

| | T = 0 | T = 1 Month 40° C./ 75% RH | T = 3 Month 40° C./ 75% RH | T = 3 Month 25° C./ 60% RH |
|---|---|---|---|---|
| HPLC purity a/a % | 99.76 | 99.79 | 99.75 | 99.77 |
| Assay % w/w | 97.4 | 98.7 | 93.8 | 96.3 |
| Water (KF) % w/w | <0.2 | NT[a] | <0.2 | NT[a] |

TABLE 11-continued

Crystalline Form I Stability Study

|  | T = 0 | T = 1 Month 40° C./ 75% RH | T = 3 Month 40° C./ 75% RH | T = 3 Month 25° C./ 60% RH |
|---|---|---|---|---|
| RRT |  |  |  |  |
| 0.96 | 0.07 | 0.07 | 0.07 | 0.07 |
| 1.84 | 0.08 | 0.08 | 0.05 | 0.05 |

*aNT = not tested*

Biological Assays

The compounds of the invention have been characterized in one or more of the following biological assays.

Assay 1: Biochemical JAK and Off-Target Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM MgCl2, and 1 mM EGTA). Recombinant GST-tagged JAK enzymes and a GFP-tagged STAT1 peptide substrate were obtained from Life Technologies.

Serially diluted compounds were pre-incubated with each of the four JAK enzymes and the substrate in white 384-well microplates (Corning) at ambient temperature for 1 h. ATP was subsequently added to initiate the kinase reactions in 10 µL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 µM, 3 µM, 1.6 µM, and 10 µM; while the substrate concentration is 200 nM for all four assays. Kinase reactions were allowed to proceed for 1 hour at ambient temperature before a 10 µL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and IC50 values were determined from a 4-parameter robust fit model with the Prism software (GraphPad Software). Results were expressed as pIC50 (negative logarithm of IC50) and subsequently converted to pKi (negative logarithm of dissociation constant, Ki) using the Cheng-Prusoff equation.

Test compounds having a higher pKi value in each of the four JAK assays show greater inhibition of JAK activity. Compounds of the invention tested in this assay typically exhibited pKi values between about 7 and about 10.3

A panel of off-target tyrosine kinase assays (Flt3, RET, FGFR2, TrkA, and pDGFRβ) were developed using a similar methodology, with recombinant enzymes obtained from Life Technologies and biotinylated peptide substrates synthesized at AnaSpec. All assays were carried out at ambient temperature with a final ATP concentration of 100 µM. Detection reagents, including Eu-anti-phosphotyrosine (pY20) antibody and SureLight APC-SA, were purchased from Perkin Elmer. Emission ratio signals (665 nm/615 nm) were recorded and utilized for data analysis, and the final results were expressed as $pIC_{50}$.

Assay 2: Cellular JAK Potency Assay

The AlphaScreen JAKI cellular potency assay was carried out by measuring interleukin-13 (IL-13, R&D Systems) induced STAT6 phosphorylation in BEAS-2B human lung epithelial cells (ATCC). The anti-STAT6 antibody (Cell Signaling Technologies) was conjugated to AlphaScreen acceptor beads (Perkin Elmer), while the anti-pSTAT6 (pTyr641) antibody (Cell Signaling Technologies) was biotinylated using EZ-Link Sulfo-NHS-Biotin (Thermo Scientific).

BEAS-2B cells were grown at 37° C. in a 5% $CO_2$ humidified incubator in 50% DMEM/50% F-12 medium (Life Technologies) supplemented with 10% FBS (Hyclone), 100 U/mL penicillin, 100 µg/mL streptomycin (Life Technologies), and 2 mM GlutaMAX (Life Technologies). On day 1 of the assay, cells were seeded at a 7,500 cells/well density in white poly-D-lysine-coated 384-well plates (Corning) with 25 µL medium, and were allowed to adhere overnight in the incubator. On day 2 of the assay, the medium was removed and replaced with 12 µL of assay buffer (Hank's Balanced Salt Solution/HBSS, 25 mM HEPES, and 1 mg/ml bovine serum albumin/BSA) containing dose-responses of test compounds. Compounds were serially diluted in DMSO and then diluted another 1000-fold in media to bring the final DMSO concentration to 0.1%. Cells were incubated with test compounds at 37° C. for 1 h, and followed by the addition of 12 µL of pre-warmed IL-13 (80 ng/ml in assay buffer) for stimulation. After incubating at 37° C. for 30 min, the assay buffer (containing compound and IL-13) was removed, and 10 µL of cell lysis buffer (25 mM HEPES, 0.1% SDS, 1% NP-40, 5 mM MgCl2, 1.3 mM EDTA, 1 mM EGTA, and supplement with Complete Ultra mini protease inhibitors and PhosSTOP from Roche Diagnostics). The plates were shaken at ambient temperature for 30 min before the addition of detection reagents. A mixture of biotin-anti-pSTAT6 and anti-STAT6 conjugated acceptor beads was added first and incubated at ambient temperature for 2 h, followed by the addition of streptavidin conjugated donor beads (Perkin Elmer). After a minimum of 2 h incubation, the assay plates were read on the EnVision plate reader. AlphaScreen luminescence signals were recorded and utilized to calculate the percent inhibition values based on DMSO and background controls.

For dose-response analysis, percent inhibition data were plotted vs. compound concentrations, and IC50 values were determined from a 4-parameter robust fit model with the Prism software. Results were expressed as the negative logarithm of the $IC_{50}$ value, $pIC_{50}$.

Test compounds having a higher $pIC_{50}$ value in this assay show greater inhibition of IL-13 induced STAT6 phosphorylation. Compounds of the invention tested in this assay typically exhibited $pIC_{50}$ values between about 6.8 and about 8.5.

An interleukin-4 (IL-4, R&D Systems) induced STAT6 phosphorylation assay was also developed in THP-1 human monocytic cells (ATCC), using the identical assay format and detection reagents. IL-4 stimulation was carried out for 30 min at a 30 ng/ml final concentration. Data collection and analysis were also conducted in a similar fashion. Compounds of the invention tested in this assay typically exhibited $pIC_{50}$ values between about 6.8 and about 8.5.

Assay 3: Cytotoxicity Assay

A CellTiter-Glo luminescent cell viability/cytotoxicity assay was carried out in BEAS-2B human lung epithelial cells (ATCC) under the normal growth condition.

Cells were grown at 37° C. in a 5% $CO_2$ humidified incubator in 50% DMEM/50% F-12 medium (Life Technologies) supplemented with 10% FBS (Hyclone), 100 U/mL penicillin, 100 µg/mL streptomycin (Life Technologies), and 2 mM GlutaMAX (Life Technologies). On day 1 of the assay, cells were seeded at a 500 cells/well density in white 384-well tissue culture plates (Corning) with 25 μL medium, and were allowed to adhere overnight in the incubator. On day 2 of the assay, 5 μL of medium containing dose-responses of test compounds was added, and incubated at 37° C. for 48 h. 30 μl of CellTiter-Glo detection solution (Promega) was subsequently added, mixed on an orbital shaker for 5 min, and incubated for additional 10 min before being read on the EnVision reader. Luminescence signals were recorded and percent DMSO control values were calculated.

For dose-response analysis, percent DMSO control data were plotted vs. compound concentrations to derive dose-response curves by line connecting each data point. The concentration at which each curve crosses the 15% inhibition threshold is defined as $CC_{15}$. Results were expressed as the negative logarithm of the $CC_{15}$ value, $pCC_{15}$.

It is expected that test compounds exhibiting a lower $pCC_{15}$ value in this assay have less likelihood to cause cytotoxicity. Compounds of the invention tested in this assay typically exhibited $pCC_{15}$ values between less than 5 and about 6.

In Vitro Assay Results

All of the compounds of Examples 1 to 17 and Tables 1 to 8 were tested in one or more of the assays described above. In the following tables, for the JAK1, JAK 2, JAK3, and TYK2 enzyme assays, A represents a $pK_i$ value ≥10 ($K_i$≤0.1 nM), B represents a $pK_i$ value between 9 and 10 ($K_i$ between 1 nM and 0.1 nM), C represents a $pK_i$ value between 7 and 9 ($K_i$ between 100 nM and 1 nM), and D represents a $pK_i$ value between 6.5 and 7 ($K_i$ between 316 nM and 100 nM). For the THP-1 and BEAS-2B cell potency assays, A represents a $pEC_{50}$ value ≥7.5 ($EC_{50}$≤32 nM), B represents a $pEC_{50}$ value between 6.7 and 7.5 ($EC_{50}$ between 200 nM and 32 nM), and C represents a $pEC_{50}$ value <6.7 ($EC_{50}$>200 nM).

| Example Number | JAK 1 (pKi) | JAK 2 (pKi) | JAK 3 (pKi) | Tyk 2 (pKi) | THP-1 IL4 pIC50 | BEAS2B pIC50 |
|---|---|---|---|---|---|---|
| 1 | A | A | C | B | B | B |
| 2 | B | B | C | C | B | B |
| 3 | B | B | C | C | B | A |
| 4 | B | B | C | C | B | |
| 5 | B | C | C | C | A | A |
| 6 | B | B | C | C | B | B |
| 7 | A | B | C | B | A | A |
| 8 | A | A | B | B | A | A |
| 9 | B | B | C | B | A | A |
| 10 | A | A | B | B | A | A |
| 11 | A | A | B | A | B | A |
| 12 | B | B | C | C | B | B |
| 13 | A | A | C | B | B | B |
| 14 | A | A | C | B | A | A |
| 15 | B | A | B | B | A | A |
| 16 | B | C | C | C | B | |
| 17 | B | A | B | B | B | B |

TABLE 1

| Example Number | JAK 1 (pKi) | JAK 2 (pKi) | JAK 3 (pKi) | Tyk 2 (pKi) | THP-1 IL4 pIC50 | BEAS2B pIC50 |
|---|---|---|---|---|---|---|
| 1-1 | B | B | C | C | C | |
| 1-2 | C | C | C | C | C | |
| 1-3 | C | C | C | C | C | |
| 1-4 | B | B | C | C | B | |
| 1-5 | B | B | C | C | B | |
| 1-6 | B | B | C | C | C | |
| 1-7 | B | B | C | C | C | |
| 1-8 | B | C | C | C | C | |
| 1-9 | B | C | C | C | C | |
| 1-10 | B | B | C | C | C | |
| 1-11 | B | B | C | C | C | |
| 1-12 | B | B | B | C | C | |
| 1-13 | B | C | C | C | A | |
| 1-14 | B | B | C | B | A | A |
| 1-15 | C | C | D | C | C | |
| 1-16 | B | B | C | C | B | |
| 1-17 | B | B | C | C | B | B |
| 1-18 | B | B | C | C | C | |
| 1-19 | A | B | B | C | B | |
| 1-20 | B | B | C | C | B | |
| 1-21 | B | B | C | C | A | B |
| 1-22 | B | B | C | B | B | A |
| 1-23 | A | A | B | B | A | A |
| 1-24 | B | A | C | B | B | A |
| 1-25 | B | A | C | B | A | A |
| 1-26 | B | B | C | C | B | |
| 1-27 | B | B | C | C | B | |
| 1-28 | B | C | B | C | C | |
| 1-29 | C | C | C | C | C | |
| 1-30 | B | A | B | B | B | |
| 1-31 | A | A | B | B | A | A |
| 1-32 | B | A | B | B | C | |
| 1-33 | B | B | C | C | C | |
| 1-34 | B | C | C | C | C | |
| 1-35 | B | B | B | B | A | |
| 1-36 | B | B | C | C | B | |
| 1-37 | B | A | B | C | B | |
| 1-38 | B | B | C | C | B | |
| 1-39 | B | B | C | C | A | A |
| 1-40 | B | B | C | C | A | A |
| 1-41 | B | A | B | B | C | |
| 1-42 | B | A | B | C | C | |
| 1-43 | B | B | C | C | A | A |
| 1-44 | B | B | C | C | A | A |
| 1-45 | B | B | C | B | B | |
| 1-46 | B | C | C | C | B | |
| 1-47 | B | A | B | B | A | A |
| 1-48 | A | A | B | B | B | |
| 1-49 | A | A | B | B | A | |
| 1-50 | A | A | C | B | B | |
| 1-51 | B | A | B | B | B | |
| 1-52 | B | B | C | B | B | |
| 1-53 | B | B | C | C | B | |
| 1-54 | B | A | B | B | | B |
| 1-55 | B | B | C | C | | B |
| 1-56 | B | B | C | B | A | A |
| 1-57 | B | B | C | C | B | |
| 1-58 | A | A | B | B | B | |

TABLE 2

| Example Number | JAK 1 (pKi) | JAK 2 (pKi) | JAK 3 (pKi) | Tyk 2 (pKi) | THP-1 IL4 pIC50 | BEAS2B pIC50 |
|---|---|---|---|---|---|---|
| 2-1 | B | C | C | C | B | B |
| 2-2 | B | C | C | C | B | B |
| 2-3 | B | B | C | C | B | A |
| 2-4 | C | C | C | C | C | |
| 2-5 | B | C | C | C | C | |
| 2-6 | B | B | C | C | B | A |
| 2-7 | B | B | C | C | B | |
| 2-8 | B | B | C | C | B | |
| 2-9 | C | C | C | C | C | |
| 2-10 | B | B | C | C | B | |
| 2-11 | B | B | C | C | B | |
| 2-12 | B | B | C | C | B | |
| 2-13 | B | B | C | C | B | |
| 2-14 | B | B | C | C | C | |
| 2-15 | B | B | C | C | A | |
| 2-16 | B | B | C | B | B | B |

TABLE 2-continued

| Example Number | JAK 1 (pKi) | JAK 2 (pKi) | JAK 3 (pKi) | Tyk 2 (pKi) | THP-1 IL4 pIC50 | BEAS2B pIC50 |
|---|---|---|---|---|---|---|
| 2-17 | B | B | C | C | B | A |
| 2-18 | B | B | C | B | A | |
| 2-19 | B | B | C | B | A | |
| 2-20 | B | B | C | C | A | A |
| 2-21 | B | B | C | C | B | |
| 2-22 | B | B | C | B | B | A |
| 2-23 | B | B | C | C | B | |
| 2-24 | B | B | C | C | A | A |
| 2-25 | B | A | B | B | A | A |
| 2-26 | B | B | C | C | | C |
| 2-27 | B | B | C | B | | B |
| 2-28 | B | A | C | B | | C |
| 2-29 | B | B | C | B | | B |
| 2-30 | B | B | C | C | | C |
| 2-31 | B | B | C | C | | B |

TABLE 3

| | | | | | | |
|---|---|---|---|---|---|---|
| 3-1 | B | B | C | C | A | |
| 3-2 | B | B | C | C | A | |
| 3-3 | B | C | C | C | A | |
| 3-4 | B | B | C | C | A | |
| 3-5 | B | C | C | C | B | |
| 3-6 | B | A | C | B | A | |
| 3-7 | B | B | C | C | B | |
| 3-8 | B | B | C | C | A | |
| 3-9 | B | B | C | C | A | |
| 3-10 | B | B | C | B | | B |
| 3-11 | B | B | C | C | | A |
| 3-12 | B | B | C | C | | B |
| 3-13 | B | B | C | C | B | B |
| 3-14 | B | B | C | C | B | A |

TABLE 4

| Example Number | JAK 1 (pKi) | JAK 2 (pKi) | JAK 3 (pKi) | Tyk 2 (pKi) | THP-1 IL4 pIC50 | BEAS2B pIC50 |
|---|---|---|---|---|---|---|
| 4-1 | A | B | C | B | A | |
| 4-2 | B | B | C | C | A | A |
| 4-3 | B | B | C | B | A | A |
| 4-4 | B | B | C | C | A | A |
| 4-5 | B | B | C | C | A | |
| 4-6 | B | B | C | C | A | |
| 4-7 | B | B | C | B | A | |
| 4-8 | B | B | C | B | A | |
| 4-9 | B | B | C | C | C | |
| 4-10 | B | B | C | C | B | B |
| 4-11 | B | C | C | C | C | |
| 4-12 | B | C | C | C | B | |
| 4-13 | B | C | C | C | B | A |
| 4-14 | C | C | C | C | B | |
| 4-15 | B | B | C | C | A | A |
| 4-16 | A | A | B | B | A | |
| 4-17 | B | B | C | B | A | |
| 4-18 | A | A | B | B | A | A |
| 4-19 | A | A | C | B | A | A |
| 4-20 | B | A | B | B | A | A |
| 4-21 | B | B | B | B | C | |
| 4-22 | B | A | B | B | A | |
| 4-23 | B | A | B | B | A | A |
| 4-24 | B | B | C | C | B | |
| 4-25 | B | B | C | C | B | |
| 4-26 | B | B | C | C | B | B |
| 4-27 | B | A | B | B | A | A |
| 4-28 | B | B | C | B | A | |
| 4-29 | A | A | B | B | A | A |

TABLE 5

| Example Number | JAK 1 (pKi) | JAK 2 (pKi) | JAK 3 (pKi) | Tyk 2 (pKi) | THP-1 IL4 pIC50 | BEAS2B pIC50 |
|---|---|---|---|---|---|---|
| 5-1 | B | B | C | B | A | A |
| 5-2 | B | C | C | C | B | |
| 5-3 | B | C | C | C | B | |
| 5-4 | B | C | C | C | A | A |
| 5-5 | B | C | C | C | B | |
| 5-6 | B | B | C | C | A | A |
| 5-7 | B | C | C | C | B | A |
| 5-8 | B | B | C | B | A | A |
| 5-9 | B | B | C | B | A | A |
| 5-10 | A | A | B | B | A | A |
| 5-11 | B | A | B | B | A | B |
| 5-12 | A | A | C | B | B | |
| 5-13 | A | A | C | B | B | |
| 5-14 | B | B | C | C | B | B |
| 5-15 | B | A | B | B | B | |
| 5-16 | B | A | B | B | B | B |
| 5-17 | B | B | B | B | B | A |
| 5-18 | B | A | B | B | B | |
| 5-19 | B | C | C | C | B | |
| 5-20 | B | B | C | B | A | B |
| 5-21 | B | A | B | B | A | A |
| 5-22 | A | A | B | B | A | A |
| 5-23 | A | A | B | B | A | |
| 5-24 | B | B | B | B | B | |
| 5-25 | B | B | B | B | B | |
| 5-26 | A | A | A | B | A | |
| 5-27 | B | B | B | B | A | A |
| 5-28 | B | B | B | B | B | |
| 5-29 | B | A | B | B | B | |
| 5-30 | B | A | B | B | A | A |
| 5-31 | B | B | C | C | B | |
| 5-32 | B | B | B | B | B | |
| 5-33 | B | B | B | B | B | |
| 5-34 | B | B | C | B | B | |
| 5-35 | B | B | B | B | A | |
| 5-36 | B | A | B | B | A | A |
| 5-37 | B | B | B | B | B | |
| 5-38 | C | C | C | C | | |
| 5-39 | B | B | C | B | B | |
| 5-40 | B | B | C | C | B | |
| 5-41 | B | B | C | C | C | |
| 5-42 | B | B | C | C | C | |
| 5-43 | B | B | C | B | B | |

TABLE 6

| Example Number | JAK 1 (pKi) | JAK 2 (pKi) | JAK 3 (pKi) | Tyk 2 (pKi) | THP-1 IL4 pIC50 | BEAS2B pIC50 |
|---|---|---|---|---|---|---|
| 6-1 | B | B | C | B | A | A |
| 6-2 | B | B | C | C | A | B |
| 6-3 | B | B | C | C | B | B |
| 6-4 | B | A | C | B | A | A |
| 6-5 | B | A | C | B | A | A |
| 6-6 | B | A | B | B | A | A |
| 6-7 | C | B | C | C | B | |
| 6-8 | B | A | B | B | A | A |
| 6-9 | B | A | B | B | A | A |
| 6-10 | B | B | C | B | B | |
| 6-11 | B | B | C | B | A | |
| 6-12 | B | B | C | C | B | |
| 6-13 | B | C | C | C | B | |
| 6-14 | B | C | C | C | A | A |
| 6-15 | B | B | C | C | A | A |
| 6-16 | B | C | C | C | B | B |
| 6-17 | B | C | C | C | A | A |
| 6-18 | A | A | C | B | A | A |
| 6-19 | B | C | C | C | B | |
| 6-20 | B | B | C | B | | B |
| 6-21 | B | B | C | B | | B |
| 6-22 | B | B | C | B | | B |
| 6-23 | B | A | C | B | | B |
| 6-24 | B | B | C | C | B | B |
| 6-25 | C | C | C | C | B | A |

TABLE 6-continued

| Example Number | JAK 1 (pKi) | JAK 2 (pKi) | JAK 3 (pKi) | Tyk 2 (pKi) | THP-1 IL4 pIC50 | BEAS2B pIC50 |
|---|---|---|---|---|---|---|
| 6-26 | B | C | C | C | B | |
| 6-27 | B | B | C | C | B | |
| 6-28 | B | B | C | C | A | A |
| 6-29 | B | B | C | B | A | A |
| 6-30 | B | B | C | B | C | |
| 6-31 | B | B | C | B | A | A |
| 6-32 | A | A | C | B | A | |
| 6-33 | A | A | C | B | B | |
| 6-34 | A | A | C | B | A | |
| 6-35 | B | A | C | B | B | |
| 6-36 | B | B | C | C | B | |
| 6-37 | B | B | C | C | B | |
| 6-38 | B | B | C | C | B | |
| 6-39 | B | C | C | C | C | |
| 6-40 | B | B | C | C | A | |
| 6-41 | A | B | C | C | A | B |
| 6-42 | B | B | C | C | C | |
| 6-43 | B | B | C | C | B | |
| 6-44 | B | C | C | C | B | |
| 6-45 | B | B | C | C | B | |
| 6-46 | B | B | C | C | C | |
| 6-47 | A | A | B | B | A | A |
| 6-48 | B | B | C | C | B | |
| 6-49 | B | B | C | C | B | |
| 6-50 | A | A | B | B | C | |
| 6-51 | B | B | C | C | C | |
| 6-52 | B | B | C | C | C | |
| 6-53 | B | B | C | C | C | |
| 6-54 | B | B | C | C | C | |
| 6-55 | C | C | C | C | C | |
| 6-56 | B | A | C | B | B | B |
| 6-57 | B | A | C | C | C | |
| 6-58 | B | A | B | C | C | |
| 6-59 | B | A | B | B | | C |
| 6-60 | A | A | B | B | | B |

TABLE 7

| | | | | | | |
|---|---|---|---|---|---|---|
| 7-1 | B | C | C | C | B | |
| 7-2 | B | C | C | C | A | A |
| 7-3 | C | C | C | C | C | |
| 7-4 | B | C | C | C | B | B |
| 7-5 | B | C | C | C | B | B |
| 7-6 | B | B | C | C | A | B |
| 7-7 | C | C | C | C | B | |
| 7-8 | B | B | C | C | B | |
| 7-9 | B | B | C | C | A | A |
| 7-10 | B | B | C | B | A | B |

TABLE 8

| Example Number | JAK 1 (pKi) | JAK 2 (pKi) | JAK 3 (pKi) | Tyk 2 (pKi) | THP-1 IL4 pIC50 | BEAS2B pIC50 |
|---|---|---|---|---|---|---|
| 8-1 | B | B | C | C | B | |
| 8-2 | B | B | C | C | A | C |
| 8-3 | B | B | C | C | A | |
| 8-4 | B | C | C | C | B | B |
| 8-5 | B | B | C | C | B | A |
| 8-6 | B | B | C | C | B | B |
| 8-7 | C | C | C | C | C | |
| 8-8 | C | C | C | C | C | |
| 8-9 | B | B | C | C | B | |
| 8-10 | A | A | C | B | A | A |
| 8-11 | B | B | C | C | B | A |
| 8-12 | B | B | C | B | A | A |
| 8-13 | B | B | C | C | B | A |
| 8-14 | B | B | C | C | A | A |
| 8-15 | B | C | C | C | C | |
| 8-16 | B | B | C | C | B | |
| 8-17 | A | A | C | C | B | |
| 8-18 | B | B | C | C | B | |
| 8-19 | B | B | C | C | C | |
| 8-20 | B | C | D | C | C | |
| 8-21 | B | B | C | C | B | |
| 8-22 | B | B | C | C | B | B |
| 8-23 | B | A | C | B | B | B |
| 8-24 | B | B | C | C | B | B |

Assay 4: Determination of Absorption in Cannulated Rats

Oral bioavailability (F %), fraction absorbed ($F_a$ %) and fraction escaping hepatic clearance ($F_h$ %) were determined in Sprague Dawley rats from the following two studies:

(1) Pharmacokinetics in rats following an IV dose of test compound: Following IV dosing, plasma samples were typically collected from 0-6 hr. Drug levels were determined using an LC-MS-MS method. The resulting drug levels were used to compute the IV pharmacokinetic parameters: AUC IV and Dose IV.

(2) Rats that have been cannulated in their portal vein (PV) and also in their jugular vein (JV) were dosed orally with test compound. Following oral dosing, plasma samples were typically collected from 0-6 hr from both the portal vein and the jugular vein. Drug levels were determined using an LC-MS-MS method. The resulting drug levels were used to compute the following pharmacokinetic parameters: AUC PO PV, AUC PO JV, and Dose PO.

Using data derived from the above studies, the oral bioavailability F %, and the quantities $F_a$ % and $F_h$ % were calculated from the following formulas:

$$F\% = (\text{AUC } PO\ JV/\text{AUC } IV)*(\text{Dose } IV/\text{Dose } PO)*100$$

$$F_a\% = (\text{AUC } PO\ PV/\text{AUC } IV)*(\text{Dose } IV/\text{Dose } PO)*100$$

$$F_h\% = \text{AUC } PO\ JV/\text{AUC } PO\ PV$$

where:
AUC PO JV=Area under the curve following oral dose and plasma collected from the jugular vein
AUC PO PV=Area under the curve following oral dose and plasma collected from the portal vein
AUC IV=Area under the curve following an intravenous dose
Dose IV=Intravenous Dose in mg/kg
Dose PO=Oral Dose in mg/kg Compounds of the invention typically exhibited oral bioavailability (F %) less than about 10% and absorption at the portal vein ($F_a$ %) less than about 20% including less than about 10%. For example the compounds of Examples 1-6, 8, and 12 all exhibited F % values less than about 5% and $F_a$ % values less than about 10%.

Assay 5: Colon Pharmacokinetics in Rats

Test compounds were individually formulated in 0.5% methyl-cellulose in water and dosed via oral gavage at 5 mg/kg to Sprague Dawley rats. At various time points (typically 1, 2, 4, 6, 24 hr) post dosing, blood samples were removed via cardiac puncture and intact colons were excised from the rats. Blood samples were centrifuged at 1500×g for 15 min to collect plasma. Colons were washed with ice cold phosphate buffered saline (PBS), weighed, and homogenized at a dilution of 1:10 in PBS. Plasma and colon levels of test compound were determined by LC-MS analysis against analytical standards constructed into a standard curve in the test matrix. A colon to plasma ratio was determined as the ratio of the colon AUC to the plasma AUC in µg hr/g. For example, the compounds of examples 1, 2, and 5 exhibited a colon to plasma ratio in excess of about 450.

Assay 6: Pharmacokinetics in Plasma and the GI Tract in Rats and Dogs

A test compound was dosed to male Sprague Dawley rats (n=3) as described in Assay 5. At each time point (0.5, 1, 3, 6, and 24 hr) plasma samples were taken by cardiac puncture and immediately afterward the GI tract was removed and the following segments excised: duodenum, proximal colon, and distal colon. Plasma and segment levels of test compound were determined as described in Assay 5. At all time points, the plasma concentration was below the limit of quantitation of 0.001 µg/mL. For the compound of example 1, for each segment, the tissue to plasma ratio was in excess of about 14000.

An analogous experiment was performed in dogs. Male beagle dogs (n=2) were dosed via oral gavage with 5 mg/kg of test compound, formulated as above. In dog number 1, plasma samples were taken at 0.25, 1, 2, 4, 6, and 24 hr post dosing. In dog number 2, plasma samples were taken to 6 hr. In both dog number 1 (at 24 hr) and dog number 2 (at 6 hr) the GI tract was removed and segmented as follows: duodenum, ileum, cecum and the colon segmented into equal thirds (proximal, middle, and distal colon). For each of the GI segments, an approximately 2 cm piece was excised in the middle of the segment. Each was washed thoroughly in ice cold PBS buffer and then homogenized in 5 volumes of PBS buffer and analyzed as above. For the compound of example 1, the ratio of concentration of compound in GI tissue to compound in plasma for collections conducted at 6 hours post oral dose ranged from about 9 to about 165 where the colon concentration was taken as the sum of the three colon segments. The GI tissue to plasma ratio ranged from about 7 to about 30 for collections conducted at 24 hours post oral dose.

Assay 7: Mouse Model of Oxazolone-Induced Colitis

Oxazolone-induced colitis is an experimental model that has a histological resemblance to human ulcerative colitis (Heller et al. Immunology, 2002, 17, 629-638). Adult BALB/C mice from Harlan were used in the assay. On day 1, animals were lightly anesthetized with isoflurane and the hairs between the shoulder were carefully removed before oxazolone (4%, 150 µL, 4:1 acetone: olive oil formulation) or vehicle solution was slowly applied for skin sensitization. Seven days after skin sensitization, the mice were fasted overnight, anesthetized with isoflurane inhalation, and a 1 mL syringe equipped with a 3.5-F catheter, filled with oxazolone solution, was inserted carefully about 4 cm into the colon of the mouse. Following insertion, 50 µL of the oxazolone solution (1%, 1:1 ethanol:water formulation) was injected very slowly (over 30 sec using an injection pump) into the colon. The catheter was removed and the mice were held vertically (head down) for 2 min to ensure that the entire oxazolone solution remained inside the colon. Drug treatment (PO, BID or TID) or vehicle was initiated a day prior to the oxazolone intrarectal (IR) challenge. Two-day post oxazolone intrarectal challenge, the Disease Activity Index (DAI) was assessed by treatment-blinded experimenters for each mouse according to the criteria score: stool consistency score (0, normal; 2, loose; 4, diarrhea), gross bleeding score (0, absence; 2, blood tinged; 4, presence), and weight loss score (0, none; 1, 1%-5%; 2, 5%-10%; 3, 10%-20%; 4, more than 20%); DAI=average of (stool consistency score+gross bleeding score+weight loss score).

Selected compounds of the invention were tested in the assay. Efficacy in the model is evidenced by a decrease in DAI score as compared with the score from vehicle treated animals. The compounds of examples 1, 2, 3, 4, 5, 6, 8, 12, and 1-38, exhibited a statistically significant decrease in DAI score as compared with vehicle treated animals in the oxazolone model at a dose of 1, 3, and/or 10 mg/kg BID, while the compounds of examples 7, 9, 11, 13, 2-1, 2-6, 2-16, 2-17, 2-22, 2-24, 4-3, 4-4, 4-13, 4-18, 4-19, 4-23, and 5-11 did not exhibit a statistically significant decrease at the doses up to 10 mg/kg BID tested in the assay.

Assay 8: Immunosuppression Effects in Mouse Splenic Natural Killer (NK) Cells

Depletion of mouse splenic cells is an experimental model of immunosuppression (Kudlacz et al., *Am. J. of Transplantation,* 2004, 4, 51-57). The compound of Example 1 was assessed in the mouse splenic cell model following the same treatment paradigm as that used in the oxazolone-induced colitis model (Assay 7).

Adult male Balb/C mice (12-14 weeks of age) from Harlan were used for the study. The compound (1, 10 and 100 mg/kg, BID) and tofacitinib (30 mg/kg, BID) as a positive control were dosed orally for three days to naïve mice. Spleens were harvested 1 or 2 h post last dose and crushed immediately for cell subtype staining. Prior to fixation, fluorophore-labelled antibodies for CD19 (FITC; B cells), CD3e (PE; pan T cells) and DX5 (APC; NK cells) were incubated with splenocyte samples from each animal to allow for simultaneous, multiple subtype % analysis on the flow cytometer. The number of total spleen cells for each animal was measured by Scepter™ 2.0 Handheld Automated Cell Counter.

The absolute number of lymphocyte subtype population (e.g., splenic B, T and NK cells) was calculated from the percentage of each subtype times total spleen cells for each animal. A one way ANOVA, with Dunnett's post hoc test, was used to compare the splenic lymphocytes number of the vehicle and test compound groups. The a level was set at p<0.05. Data were presented as the mean±SEM for each group.

The positive control, tofacitinib (30 mg/kg; PO, BID), dose-dependently and significantly decreased splenic NK cell counts. In the same study, splenic NK cell counts were unaffected by the compound of Example 1 at PO (BID) doses up to 100 mg/kg (the maximum dose tested). No treatment effect was observed for the B and T cell populations with either compound.

This data, in conjunction with the 1 mg/kg minimal dose that caused a significant anti-colitic effect in the mouse model of oxazolone-induced colitis (Assay 7), allow a functional therapeutic index of >100 to be computed for the compound of Example 1.

Assay 9: First in Human Study to Evaluate the Safety, Tolerability and Pharmacokinetics in Healthy Subjects The compound of Example 1 was evaluated in a double-blinded, randomized, placebo-controlled, single ascending dose (SAD) and multiple ascending dose (MAD) study of safety, tolerability, and pharmacokinetics in healthy subjects. Pharmacokinetic samples were collected up to 72 hours post the final dose in both the SAD study (after the first dose) and MAD study (after 14 days of once-daily dosing). The SAD study enrolled 5 cohorts and the MAD study enrolled 4 cohorts totaling 72 subjects, of which 71 completed the dosing period.

Plasma pharmacokinetic (PK) parameters were determined by non-compartmental analysis using WinNonLin Version 6.4.0 (Pharsight, St Louis, MO). The plasma PK parameter presented here is:

$C_{max}$: maximum concentration in plasma

Following a single dose up to 1000 mg, average $C_{max}$ plasma concentrations of the compound were less than 50 ng/mL with no individual subject achieving a $C_{max}$ of greater than 100 ng/mL. Following 14 days of compound administration up to 300 mg, average $C_{max}$ plasma compound concentrations were less than 15 ng/mL with no individual subject achieving a $C_{max}$ of greater than 30 ng/mL. Comparison of these data to other orally administered compounds, suggests that the compound of Example 1 has a very low oral bioavailability. Also, high drug concentration was observed in stool samples suggesting significant exposure in the gastrointestinal tract.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula:

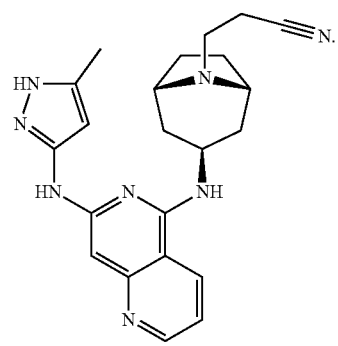 [SMILES: Cc1cc(Nc2cc3ncccc3c(N[C@@H]3C[C@H]4CC[C@@H](C3)N4CCC#N)n2)n[nH]1]

2. A method for inhibiting a Janus kinase enzyme in a mammal, wherein the method comprises administering to the mammal in need thereof a therapeutically effective amount of the compound of claim 1.

3. The method of claim 2, wherein the mammal has ulcerative colitis or Crohn's disease.

4. The method of claim 2, wherein the mammal is a human.

5. The method of claim 2, wherein the method further comprises administering to the mammal in need thereof one or more additional therapeutic agents.

* * * * *